US010188633B2

(12) United States Patent
Nelson et al.

(10) Patent No.: US 10,188,633 B2
(45) Date of Patent: Jan. 29, 2019

(54) IDENTIFICATION OF SMALL MOLECULES THAT FACILITATE THERAPEUTIC EXON SKIPPING

(71) Applicant: The Regents of the University of California, Oakland, CA (US)

(72) Inventors: Stanley F. Nelson, Los Angeles, CA (US); M. Carrie Miceli, Los Angeles, CA (US); Miriana Moran, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/085,801

(22) Filed: Mar. 30, 2016

(65) Prior Publication Data

US 2016/0220538 A1    Aug. 4, 2016

Related U.S. Application Data

(60) Division of application No. 14/026,699, filed on Sep. 13, 2013, now abandoned, which is a continuation-in-part of application No. PCT/US2012/053157, filed on Aug. 30, 2012.

(60) Provisional application No. 61/700,661, filed on Sep. 13, 2012, provisional application No. 61/529,041, filed on Aug. 30, 2011.

(51) Int. Cl.

| A61K 48/00 | (2006.01) |
|---|---|
| C12N 15/113 | (2010.01) |
| C12Q 1/68 | (2018.01) |
| A61K 31/4178 | (2006.01) |
| A61K 31/7105 | (2006.01) |
| C12Q 1/6897 | (2018.01) |
| A61K 45/06 | (2006.01) |
| A61K 31/475 | (2006.01) |
| A61K 31/5415 | (2006.01) |
| A61K 31/609 | (2006.01) |
| A61K 31/713 | (2006.01) |
| A61K 31/122 | (2006.01) |
| A61K 31/138 | (2006.01) |
| A61K 31/166 | (2006.01) |
| A61K 31/277 | (2006.01) |
| A61K 31/4025 | (2006.01) |
| A61K 31/404 | (2006.01) |
| A61K 31/407 | (2006.01) |
| A61K 31/4184 | (2006.01) |
| A61K 31/454 | (2006.01) |
| A61K 31/5377 | (2006.01) |
| A61K 31/549 | (2006.01) |
| A61K 31/554 | (2006.01) |
| A61K 31/7064 | (2006.01) |
| A61K 31/7088 | (2006.01) |
| C12Q 1/6806 | (2018.01) |

(52) U.S. Cl.
CPC ........ *A61K 31/4178* (2013.01); *A61K 31/122* (2013.01); *A61K 31/138* (2013.01); *A61K 31/166* (2013.01); *A61K 31/277* (2013.01); *A61K 31/404* (2013.01); *A61K 31/407* (2013.01); *A61K 31/4025* (2013.01); *A61K 31/4184* (2013.01); *A61K 31/454* (2013.01); *A61K 31/475* (2013.01); *A61K 31/5377* (2013.01); *A61K 31/549* (2013.01); *A61K 31/5415* (2013.01); *A61K 31/554* (2013.01); *A61K 31/609* (2013.01); *A61K 31/7064* (2013.01); *A61K 31/7088* (2013.01); *A61K 31/713* (2013.01); *A61K 31/7105* (2013.01); *A61K 45/06* (2013.01); *C12N 15/113* (2013.01); *C12Q 1/6806* (2013.01); *C12Q 1/6897* (2013.01); *C12N 2310/113* (2013.01); *C12N 2310/3233* (2013.01); *C12N 2320/31* (2013.01); *C12N 2320/33* (2013.01)

(58) Field of Classification Search
CPC .. A61K 45/06; A61K 2300/00; C12N 15/113; C12N 2310/11; C12N 2320/33
USPC .............. 424/9.1; 435/6.11, 6.12, 6.13, 91.1, 435/91.31, 196, 320.1, 455, 6.1; 506/10; 530/388.22; 514/1, 2, 44, 171, 406; 536/23.1, 23.5, 23.31, 24.3, 24.5
See application file for complete search history.

(56) References Cited

U.S. PATENT DOCUMENTS

| 2010/0130591 A1* | 5/2010 | Sazani | ................... C12N 15/111 514/44 A |
|---|---|---|---|
| 2014/0011782 A1* | 1/2014 | Wynne | ................... A61K 45/06 514/171 |

OTHER PUBLICATIONS

O'Leary et al, PLoS One, vol. 4, No. 12, e8348, pp. 1-15 (2009).*
Bellinger et al, Nature Med., vol. 15, No. 3, pp. 325-330 (2009).*
Hu et al, Molecular Therapy, vol. 18, No. 4, pp. 812-818 (2010).*
Bertorini et al, Muscle & Nerve, vol. 14, pp. 503-507 (1991).*
Nishida et al, Nature Communications, vol. 2, No. 308, pp. 1-8 (2011).*

(Continued)

*Primary Examiner* — Jane J Zara
(74) *Attorney, Agent, or Firm* — Norton Rose Fulbright US LLP

(57) ABSTRACT

This invention relates, e.g., to a method for enhancing exon skipping in a pre-mRNA of interest, comprising contacting the pre-mRNA with an effective amount of a small molecule selected from the compounds shown in Table 1, or a pharmaceutically acceptable salt, hydrate, solvate, or isomer thereof, and, optionally, with an antisense oligonucleotide that is specific for a splicing sequence in the pre-mRNA Methods for treating Duchenne muscular dystrophy (DMD) are disclosed.

16 Claims, 21 Drawing Sheets
Specification includes a Sequence Listing.

(56) References Cited

OTHER PUBLICATIONS

Stollov et al., "A High-Throughput Screening Strategy Identifies Cardiotonic Steroids as Alternative Splicing Modulators", PNAS, 2008 vol. 105, Issue 32, pp. 11218-11223.
Hu et al., "Guanine Analogues Enhance Antisense Oligunocleotide-Induce Exon Skpping in Dystrophin Gene In Vitro and In Vivo", Molecular Therapy, 2010, vol. 18, Issue 4, pp. 812-818.
Yin et al., "Pip5 Transduction Peptides Direct High Efficiency Oligonucleotide-Mediated Dystrophin Exon Skipping in Heart Phenotypic Correction in mdx Mice", Molecular Therapy, Jul. 2011, vol. 19, Issue 7, pp. 1295-1303.
O'Leary et al., "Identification of Srnall Molecule and Genetic Modulators of AON-induced Dystrophin Exon Skipping by High-Throughput Screening", PLoS One, 2009, vol. 4, Issue 12, Article No. e8348.
Nishida et al., "Chemical treatment enhances skipping of a mutated exon in the dystrophin gene", Nature Communications, May 2011 (Epub), vol. 2, No. 5, Article No. 308.
Eleazer et al., "Furaltadone hydrochloride in treatment of avian vibrionic hepatitis and chronic respiratory disease complex in chickens," *Poultry Science*, 1967; 46(4): 819-822.
Office Action issued in European Application No. 12826896.8, dated Apr. 10, 2017.

\* cited by examiner

IDENTIFICATION OF SMALL MOLECULES THAT FACILITATE THERAPEUTIC EXON SKIPPING

CROSS-REFERENCE TO RELATED APPLICATIONS

This application is a divisional of U.S. patent application Ser. No. 14/026,699, filed Nov. 13, 2013, which claims the benefit of the filing date of U.S. Provisional Application No. 61/700,661, filed Sep. 13, 2012, and is a CIP of PCT Application No. PCT/US2012/053157 filed Aug. 30, 2012, which claims the benefit of the filing date of U.S. Provisional Application No. 61/529,041, filed Aug. 30, 2011, all of which are incorporated by reference herein in their entireties.

This invention was made with government support under grant number AR058333 awarded by the National Institutes of Health and grant number W81XWH-05-1-0616 and W81XWH-09-0599 awarded by the U.S. Army, Medical Research and Materiel Command. The government has certain rights in the invention.

SEQUENCE LISTING

The instant application contains a Sequence Listing which has been submitted in ASCII format via EFS-Web and is hereby incorporated by reference in its entirety.

BACKGROUND INFORMATION

Duchenne muscular dystrophy (DMD) is a lethal X-linked recessive disease characterized by progressive muscle weakness over a patient's lifetime [1]. It is the most common childhood form of muscular dystrophy affecting about 1 out of 3500 live male births worldwide [2]. DMD is primarily caused by out of frame multi-exon deletions in the DMD gene that ablate dystrophin protein production [3]. Dystrophin is an essential component of the dystrophin glycoprotein complex (DGC), which functions in linking the actin cytoskeleton to extracellular matrix to provide sarcolemmal stability in the context of muscle contraction. The DGC also plays a role recruiting and organizing signal transducers at the sarcolemmal membrane. Both of these activities are required for muscle cell health, and thus the absence of dystrophin leads to progressive loss of muscle function. Dystrophin binds to actin via N-terminal sequences and to b dystroglycan within the DGC via carboxyl terminal domains, whereas the central portion of the protein consists of a rod domain containing multiple spectrin repeats. Deletions within the central rod domain that preserve the reading frame can produce an internally deleted dystrophin protein that retains some functionality and localizes to the membrane within the DGC [4]. Typically, the more mild allelic disorder, Becker muscular dystrophy, results from DMD mutations in the rod domain which remain in—frame 3' of the deletion and produce a functional dystrophin protein [5]. There are no curative therapies for DMD, and the only demonstrated pharmacological treatment is corticosteroids, which may prolong ambulation for up to 3 years, but with substantial side effects [6]. An emerging therapy, exon skipping, targets individual exons with antisense oligos (AOs) for exclusion from mRNA based on an individual's known genomic DNA mutation with the goal to change out-of-frame mutations into in-frame DMD deletions that restore the reading frame in dystrophin mRNA and allow translation of dystrophin protein. FIG. 14 is a schematic illustration of antisense-mediated therapeutic exon skipping. AOs have been successfully demonstrated to promote DMD exon skipping and restore dystrophin protein expression in mice, dogs and humans in recent clinical trials [7-12]. High dose, chronic administration of an exon 23 directed AO in the mdx mouse demonstrated substantial disease reduction highlighting the tremendous promise of this therapy for DMD in humans [13]. A series of AOs are under development for human use and about half of all DMD patients could be treated with the targeting of 6 different exons (51, 45, 53, 44, 52, 50) in the most frequently deleted portion of the gene between exons 45-53 [14]. For instance, DMD exon 51 skipping will be appropriate for about 13% of all DMD patients, and is the first in clinical trials with two different backbone chemistries, 2'-O-methyl phosphorothioate and morpholino phosphorodiamidate (PMO), both of which have shown promising results [8-10]. These studies are paving the way in personalized genetic medicine.

Recent phase 1-2a clinical trial results utilizing systemic 2'-O-methyl modified AO directed against DMD exon 51 (Pro051) rescued dystrophin protein at levels ranging from 1.8-15.6% of normal [8]. A modest improvement in the 6 minute walk test at 48 weeks was observed with weekly subcutaneous dosing of 6 mg/kg in a non-placebo controlled extension trail, but it remains to be determined if the levels of dystophin produced are sufficient to impart substantial functional utility or longterm protection of muscle [15]. Morpholino AO directed against exon 51 (AVI-4658) resulted in dystrophin rescue with up to 55% of myofibers induced to be dystrophin positive after 12 weeks of therapy in humans. However, the total amount of dystrophin induced was generally low, at 0-27% of normal [16]. Further, DMD exon skipping efficacy and dystrophin expression varies across patients, and muscle types.

There is a need for an improvement in exon skipping therapy that would result in more total dystrophin expression and broader effect in multiple muscle groups. For example, synergistic treatments that would permit equal efficacy with reduced AO dose, accompanied by lower toxicity, could substantially impact the practicality of the chronic administration of expensive to produce oligonucleotides [17].

Arrays were scanned with the DNA Microarray Scanner with Surescan High-Resolution Technology (Agilent) and data was extracted with Feature Extraction Software version 10.5.1.1. The values were extracted from the software and analyzed in R. The log ratio of the Cy3/Cy5 intensity for all probes is given in Panel B. Probes 4409 to 5615 demonstrated lower Cy3 signal and are consistent with a deletion from intron 44 to intron 50, which includes exons 45-50 of DMD.

Figure 7:
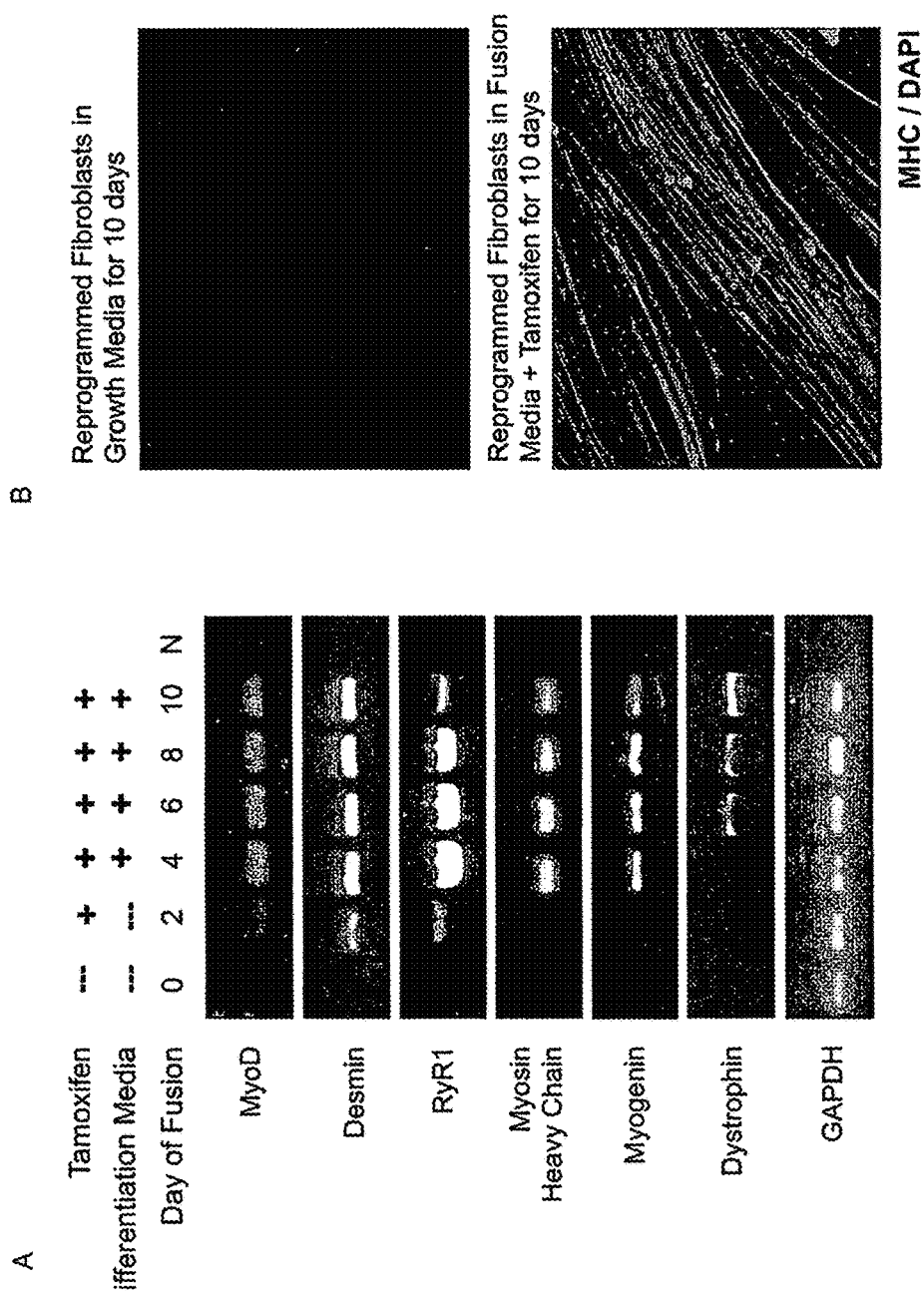

FIG. 7 shows that reprogrammed fibroblasts temporally express muscle markers at the RNA and protein level during the fusion process. Reprogrammed GM05017 patient fibroblasts were seeded onto laminin coated dishes in growth media (DMEM with 15% FBS, 1% nonessential amino acids, 1% pen/strep). The following day MyoD was induced with 5 uM tamoxifen in growth media for 24 hours. On day 3 the growth media was removed and replaced with fusion media (2% horse serum, 2% insulin-transferrin-selenium (Sigma), 1:1 serum free DMEM to Ham's F-10) that contained 1 uM tamoxifen. The cells were incubated in fusion media with 1 uM tamoxifen remained on the cells until harvesting at day 10. (A) During the fusion process cells temporally expressed indicated genes as detected by RT-PCR. (B) Myosin heavy chain (MHC) is expressed in multinucleated elongated cells consistent with differentiation into myotubes (lower panel). Cells remaining in growth media without tamoxifen failed to express myosin heavy chain (upper panel).

Figure 8:
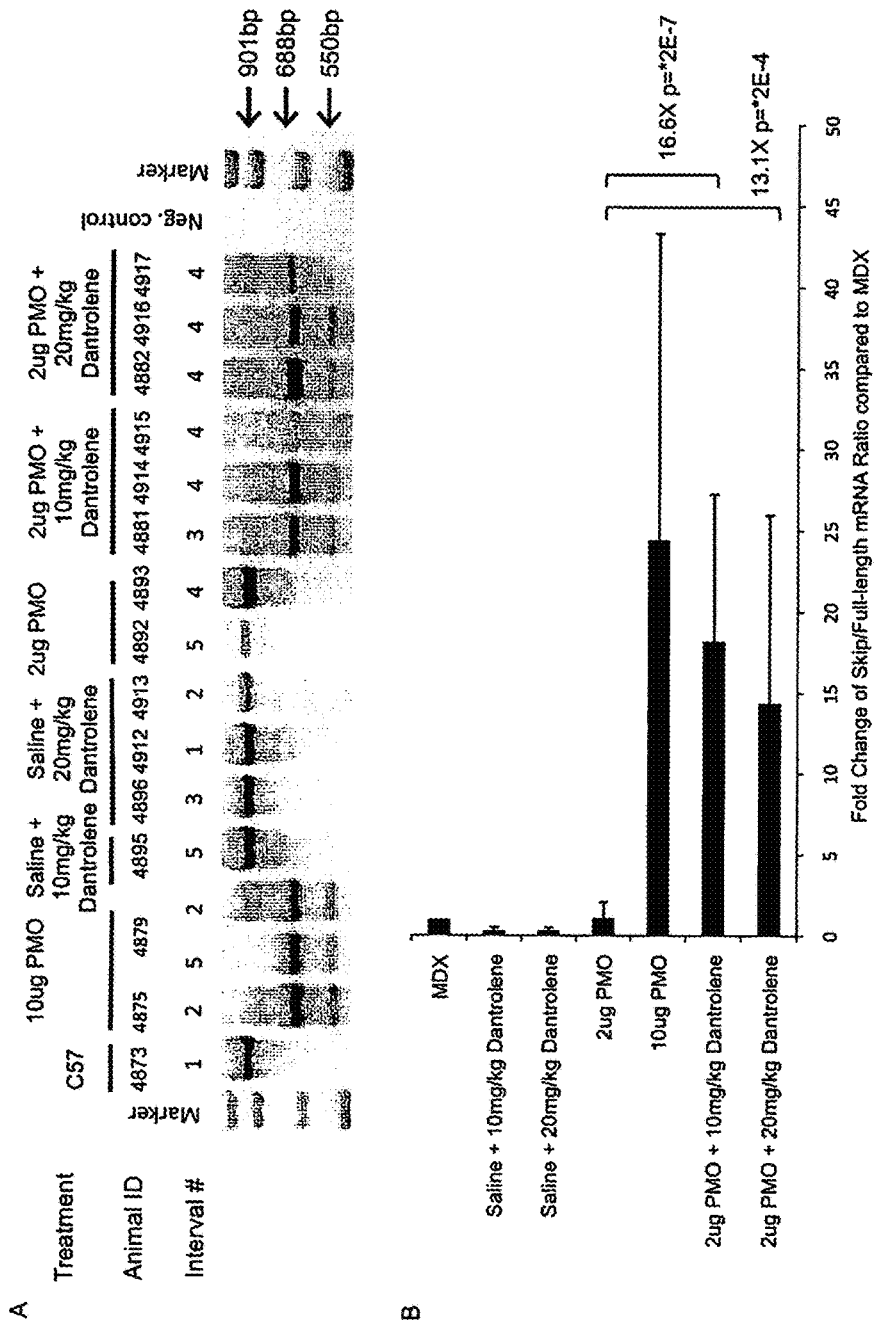

FIG. 8 shows that Dantrolene enhances Dmd exon 23 skipping with intramuscular PMOE23. (A) Exon 23 skipping was determined using a nested RT-PCR of RNA isolated from the tibialis anterior muscle, between Dmd exons 20-26. The 901 bp product is the unskipped mRNA species whereas the 688 bp product represents the exclusion of exon 23, and the 550 bp product is skipping both exons 22 and 23 [Mann et al 2001]. (B) Quantitative taqman assay to assess Dmd exon 23 skipping. The ratio of mRNA species (exon 23 skipped vs. full length) from total RNA, derived from two central intervals spanning 400 microns within the tibialis anterior muscle, was compared for 3 mice per treatment group. The skip to full-length mRNA ratios are represented as their fold change with respect to mdx untreated controls, with error bars indicating the standard deviation of measurements from 3 mice per group.

Figure 9:
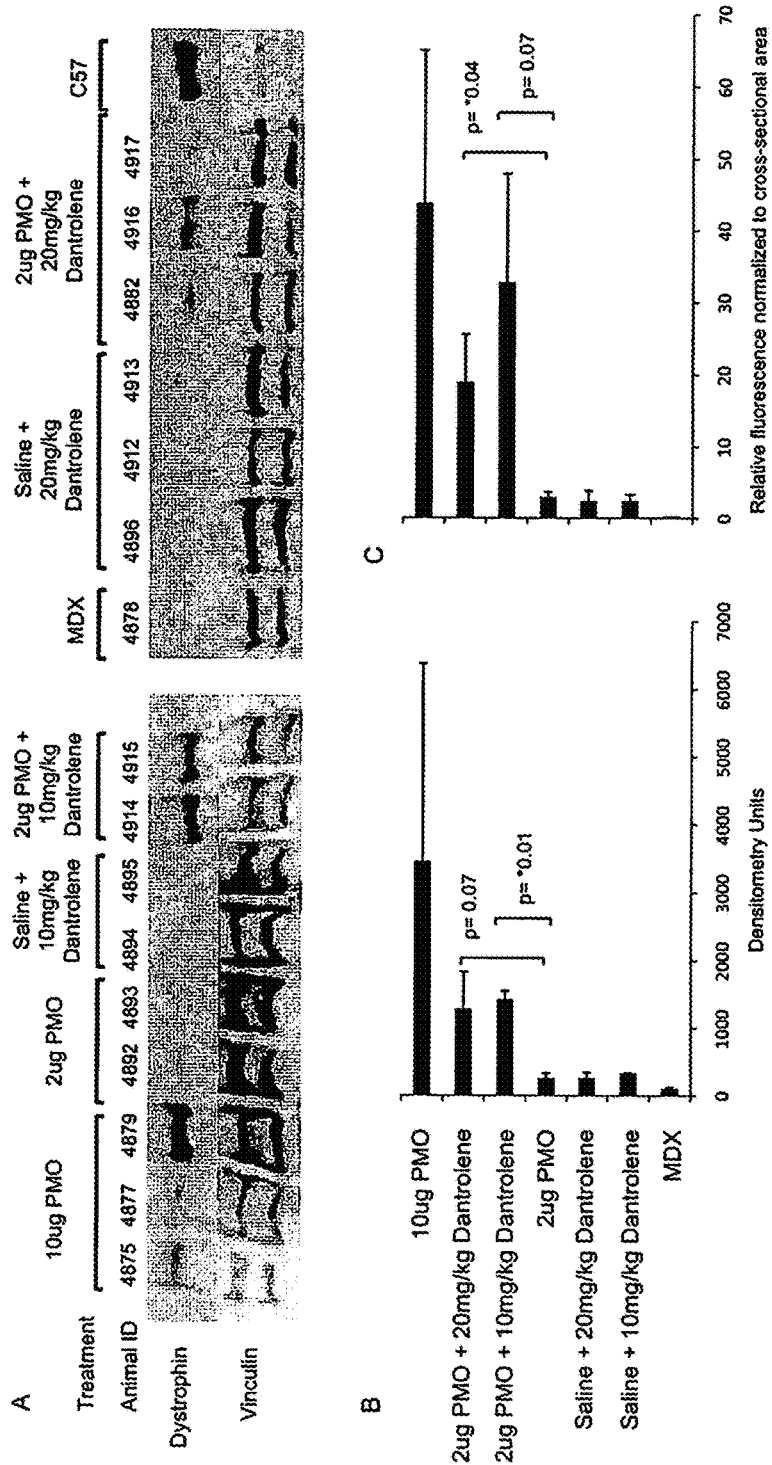

FIG. 9 shows that Dantrolene rescues dystrophin protein in the tibialis anterior muscle after intramuscular injection of PMOE23. (A) Western blot showing dystrophin expression (MANDYS8) in isolated muscle samples from the tibialis anterior muscle. Vinculin is shown as a relative loading control. Protein isolates from C57 mice were loaded at one-tenth the levels of samples from mdx mice. (B) Quantitation of dystrophin expression in the tibialis anterior as determined by densitometry analysis of western blot bands. (C) Quantitative fluorescence of dystrophin expression from muscle cross-sections as described in FIG. 3d.

Figure 10:
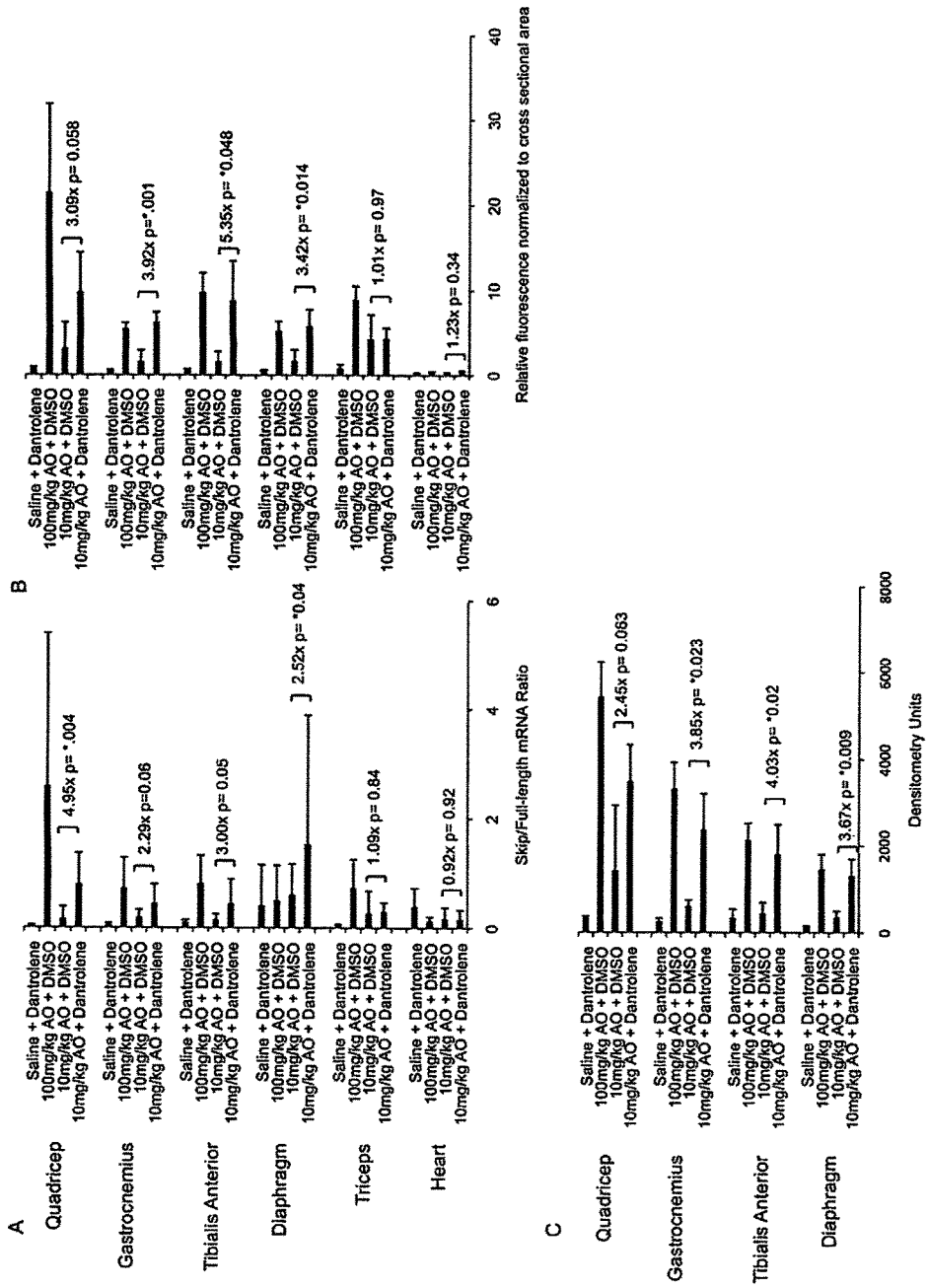

FIG. 10 shows that Dantrolene enhances systemic PMOE23 directed Dmd exon 23 skipping and dystrophin protein rescue in the mdx mouse. (A) Quantitative qRT-PCR for the detection of Dmd exon 23 skipping represented as the Dmd exon 23 skip/full-length mRNA ratio. The increase in the proportion of exon 23 skipped mRNA species in the 10 mg/kg AO+Dantrolene as compared to the carrier control is given followed by the p value for each skeletal muscle. (B) Quantitative fluorescence as described in FIG. 3d for each skeletal muscle. The increase in the proportion of dystrophin protein in the 10 mg/kg AO+Dantrolene as compared to the carrier control is given followed by the p value for each skeletal muscle. (C) Densitometry analysis of Dystrophin protein detected for each treatment group from the quadriceps, gastrocnemius, tibialis anterior, and diaphragm. Dystrophin signal was normalized to the vinculin loading control before comparisons across treatment groups.

Figure 11:
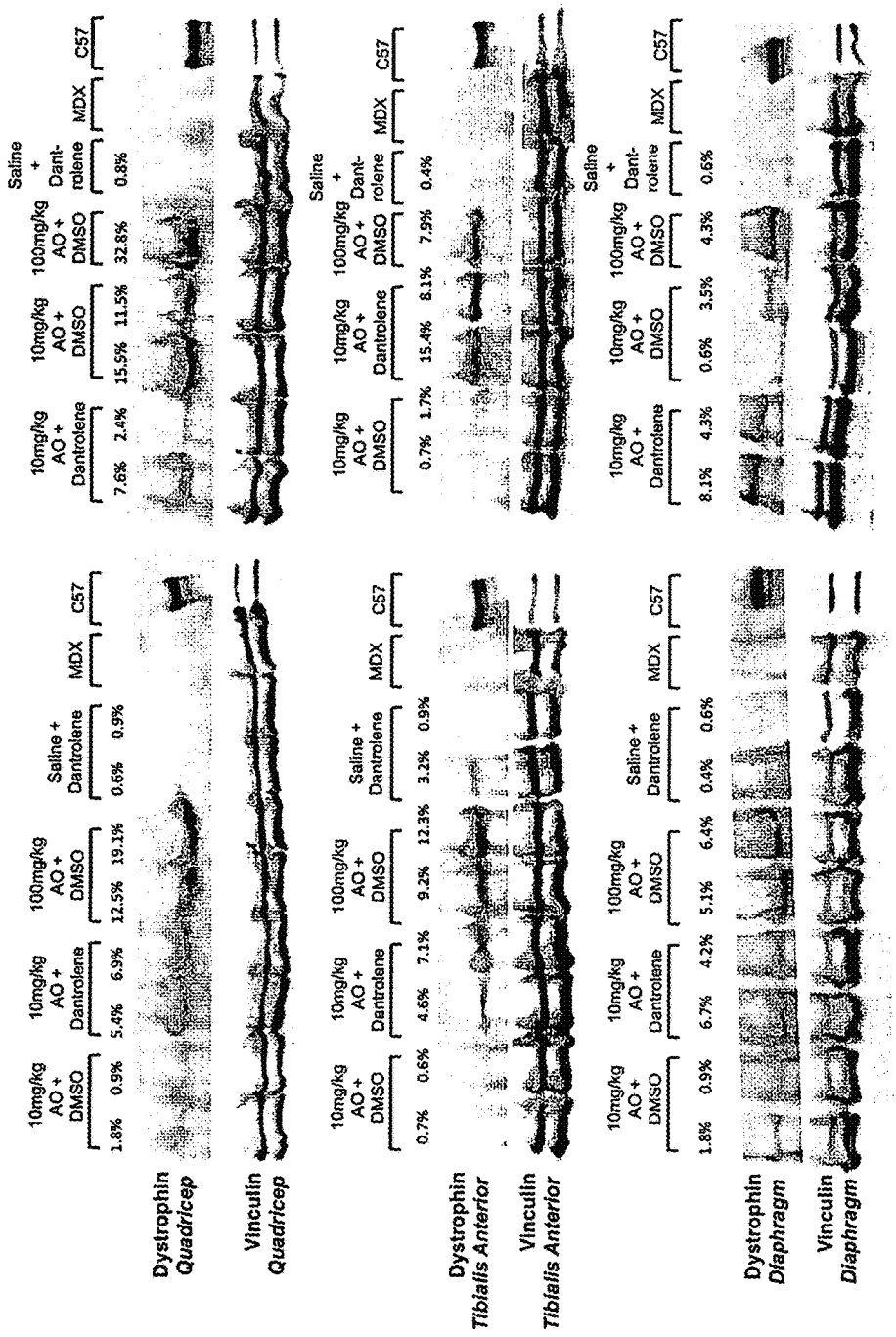

FIG. 11 shows individual Western blots for dystrophin in the quadriceps, tibialis anterior, and diaphragm. Dystrophin expression in the muscles of treated mice is shown as detected using the Mandys8 antibody. 40 ug of protein was loaded for each muscle for the mdx mice and 4 ug of protein was loaded for the C57 control. The percentage above each lane depicts the relative dystrophin expression when comparing to a wildtype (C57) control, as determined by optical density measurements of the indicated bands.

Figure 12:
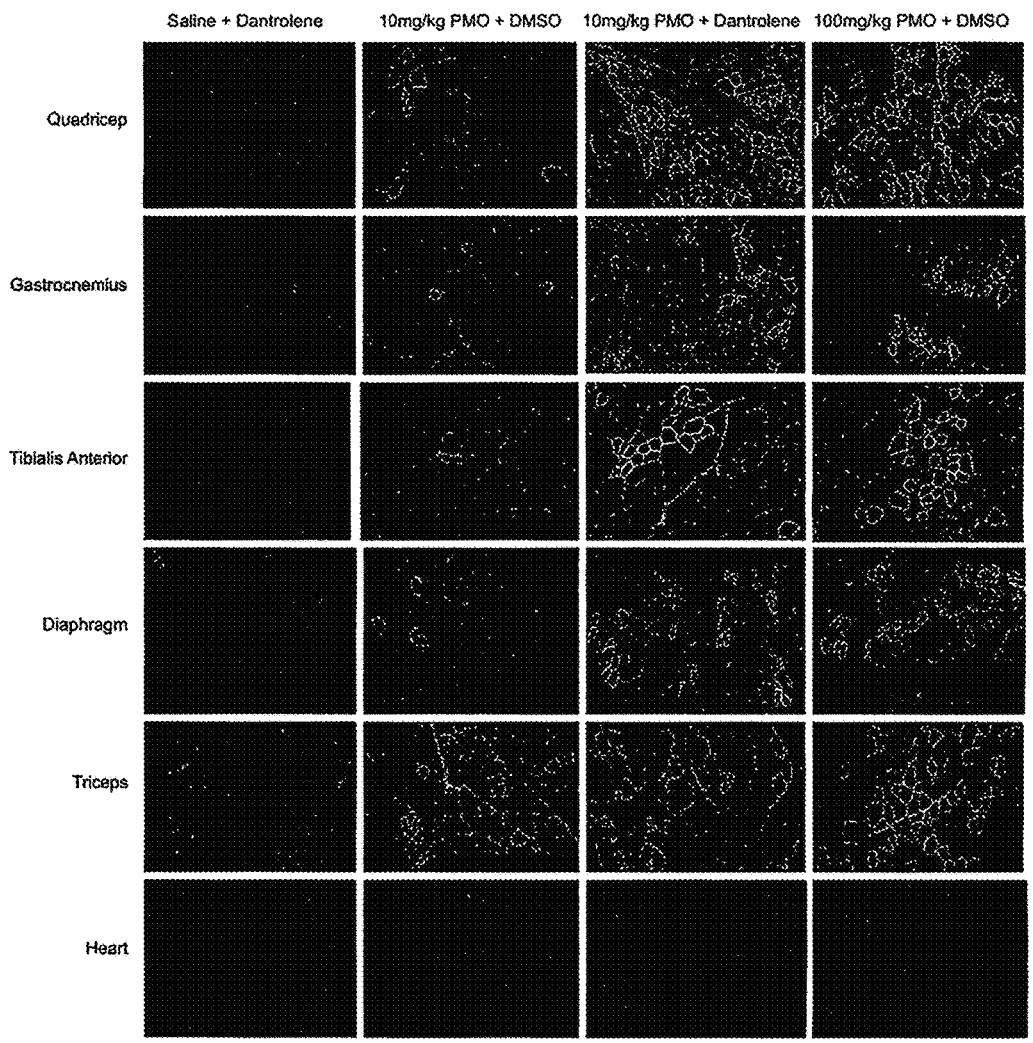

FIG. 12 shows individual micrographs from all skeletal muscles depicting dystrophin protein and DNA. Whole muscle cross sections from mice are shown with cell nuclei labeled using DAPI (light stain) and dystrophin expression detected using the Mandys8 antibody (more intense (whiter) stain).

Figure 13:
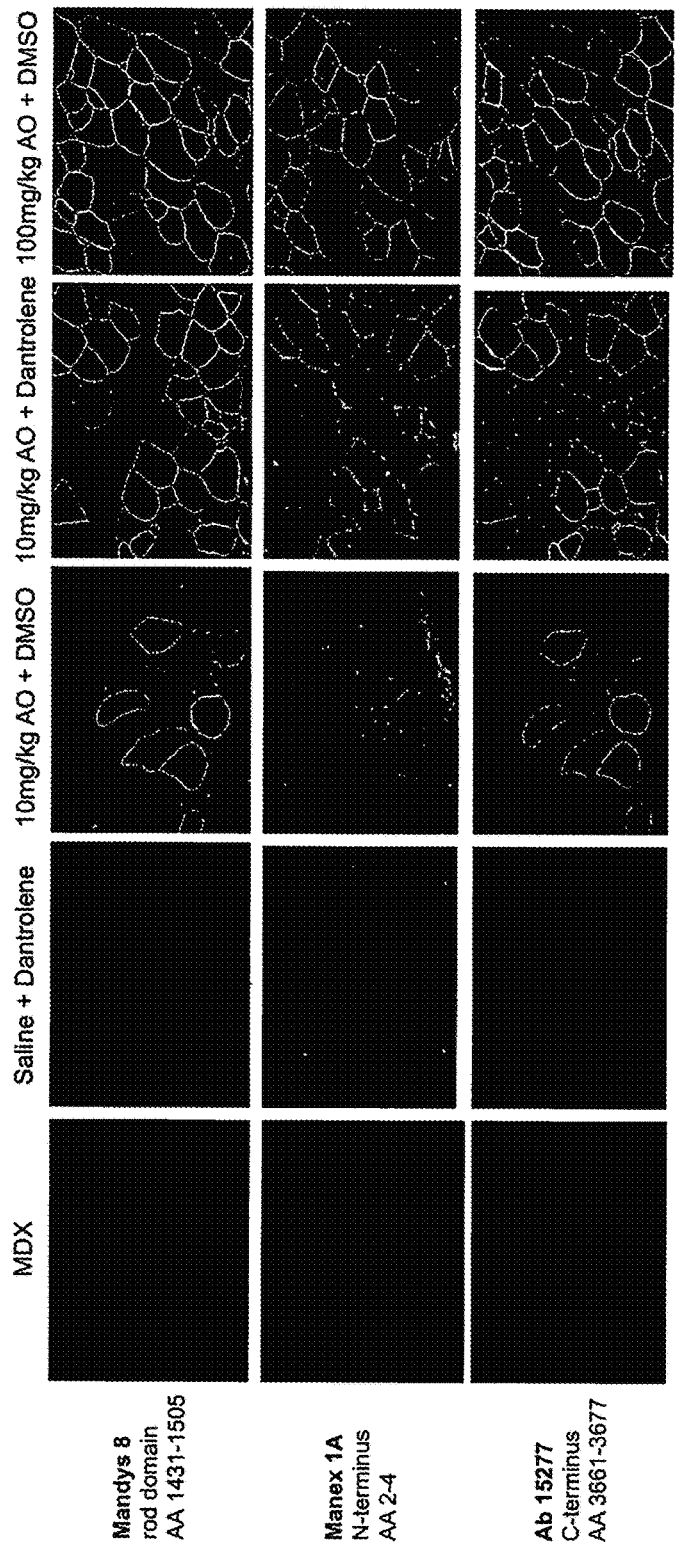

FIG. 13 shows that Dantrolene rescues full-length dystrophin protein in combination with AO that is correctly localized to the sarcolemma. Serial sections of the quadriceps muscle from 1 mouse per treatment group were stained for dystrophin with antibodies corresponding to 3 different protein domains; the rod domain, N terminus, and C terminus. Dystrophin is detected and correctly localized to the sarcolemma with all 3 antibodies.

Figure 14:
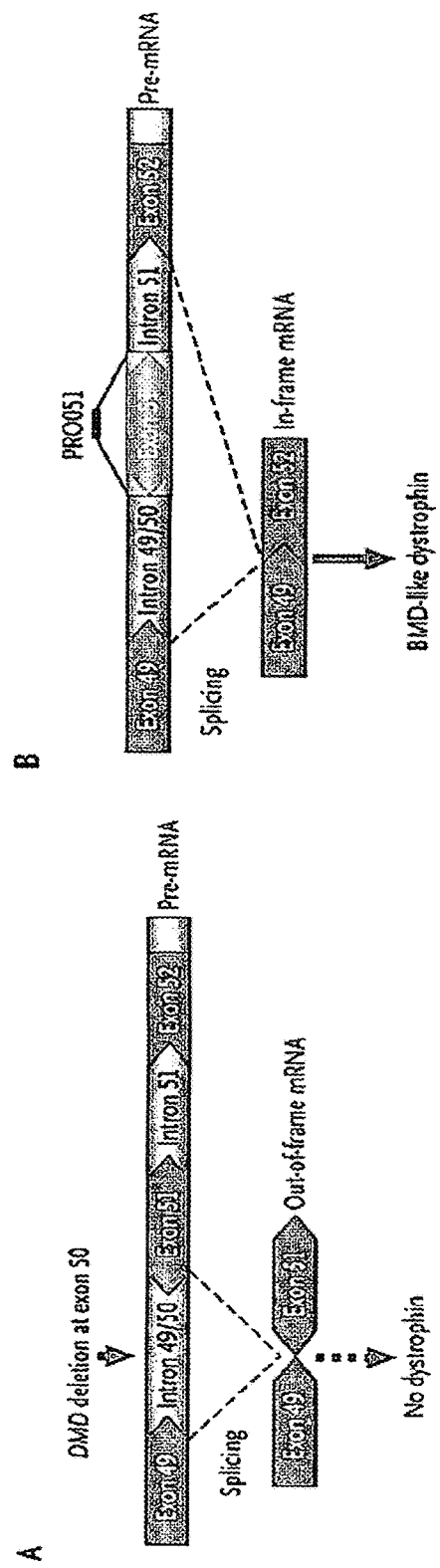

FIG. 14 illustrates the general concept of antisense mediated therapeutic exon skipping for DMD. Shown is Exon 51 skipping (with the antisense oligo PRO051).

Figure 15:
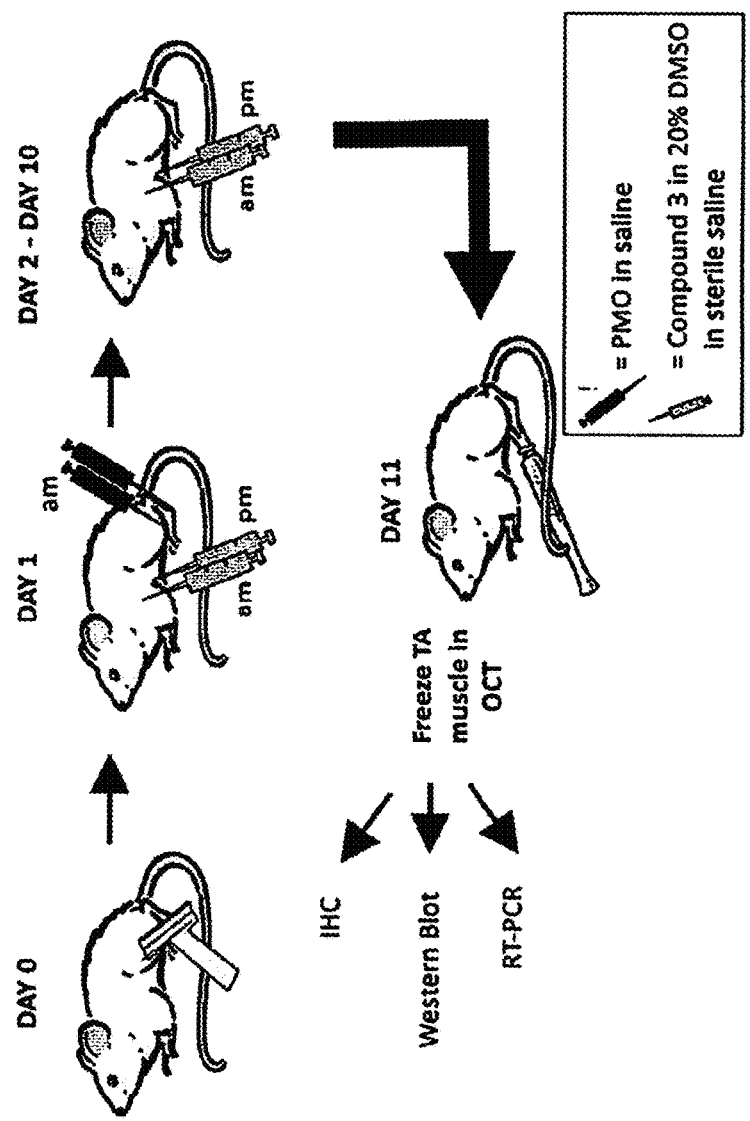

FIG. 15 shows a schematic of enhancing PMO exon skipping in the mdx mouse protocol. At day 11, the effect of the small molecule compound being tested is assessed at the RNA, protein and subcellular levels.

Figure 16:
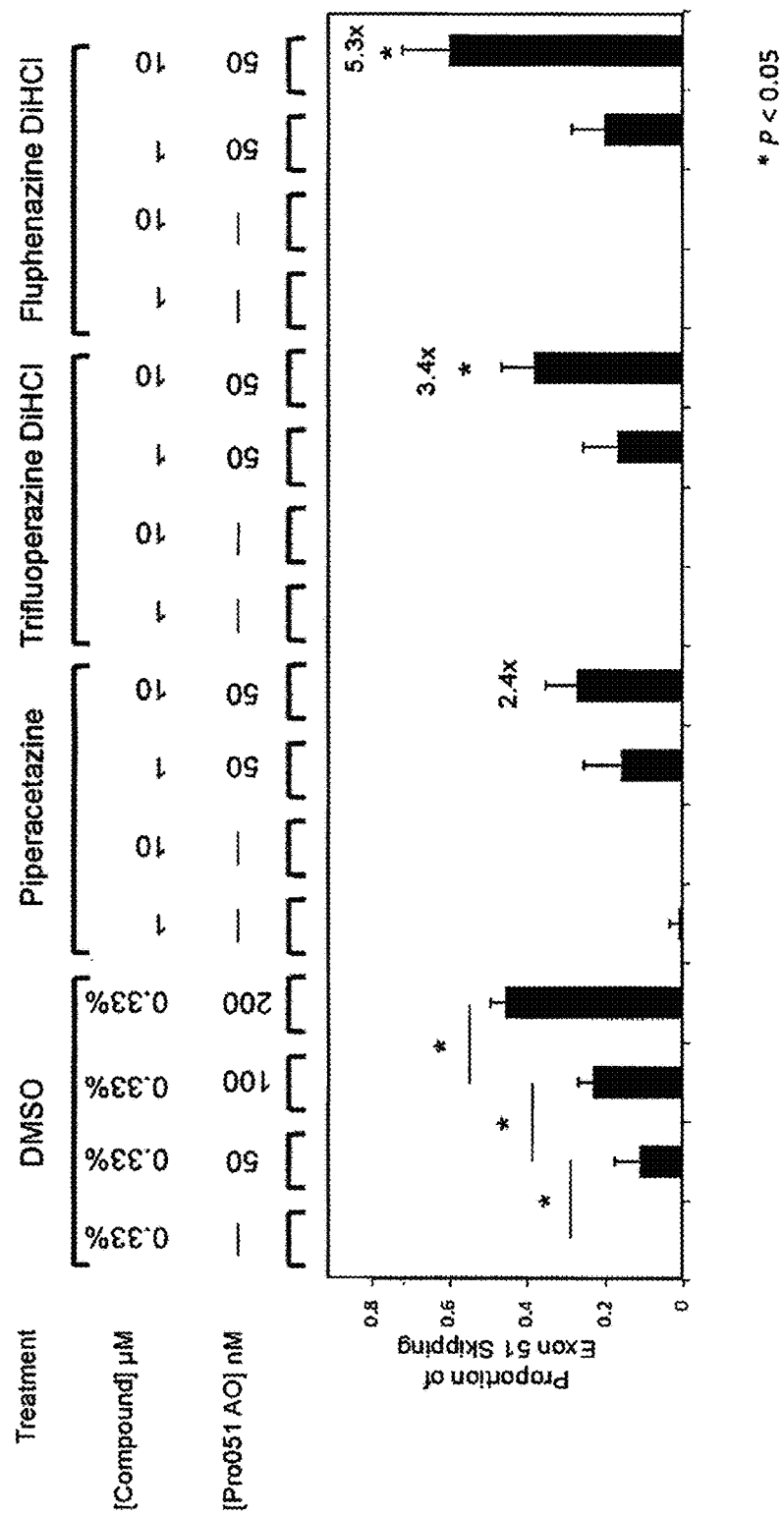

FIG. 16 shows that structurally similar phenothiazines enhance AO directed DMD exon 51 skipping. Patient fibroblasts with a DMD exon 45-50 deletion were immortalized and transduced with a lenti-viral vector expressing inducible MyoD to create iDRMs (inducibly directly reprogrammable myotubes, specifically iDRM05017s). iDRM05017s were induced for MyoD activity and then cultured for 10 days in fusion media. On Day 7, AO was added for twenty-four hours then removed and Piperacetazine, Trifluoperazine Dihydrochloride, Fluphenazine Dihydrochloride or vehicle (Dimethyl sulfoxide; DMSO) were added in fresh media. After two days total RNA was harvested, cDNA reverse transcribed with a DMD specific primer in exon 54, and exon 51 skipping was detected by nested RT-PCR spanning exons 43-52. Quantitation of exon 51 skipping was performed using the Agilent Bioanalyzer and is represented as the proportion of exon 51 skipping. Error bars represent the standard deviation (SD) of 3 independent wells.

Figure 17:
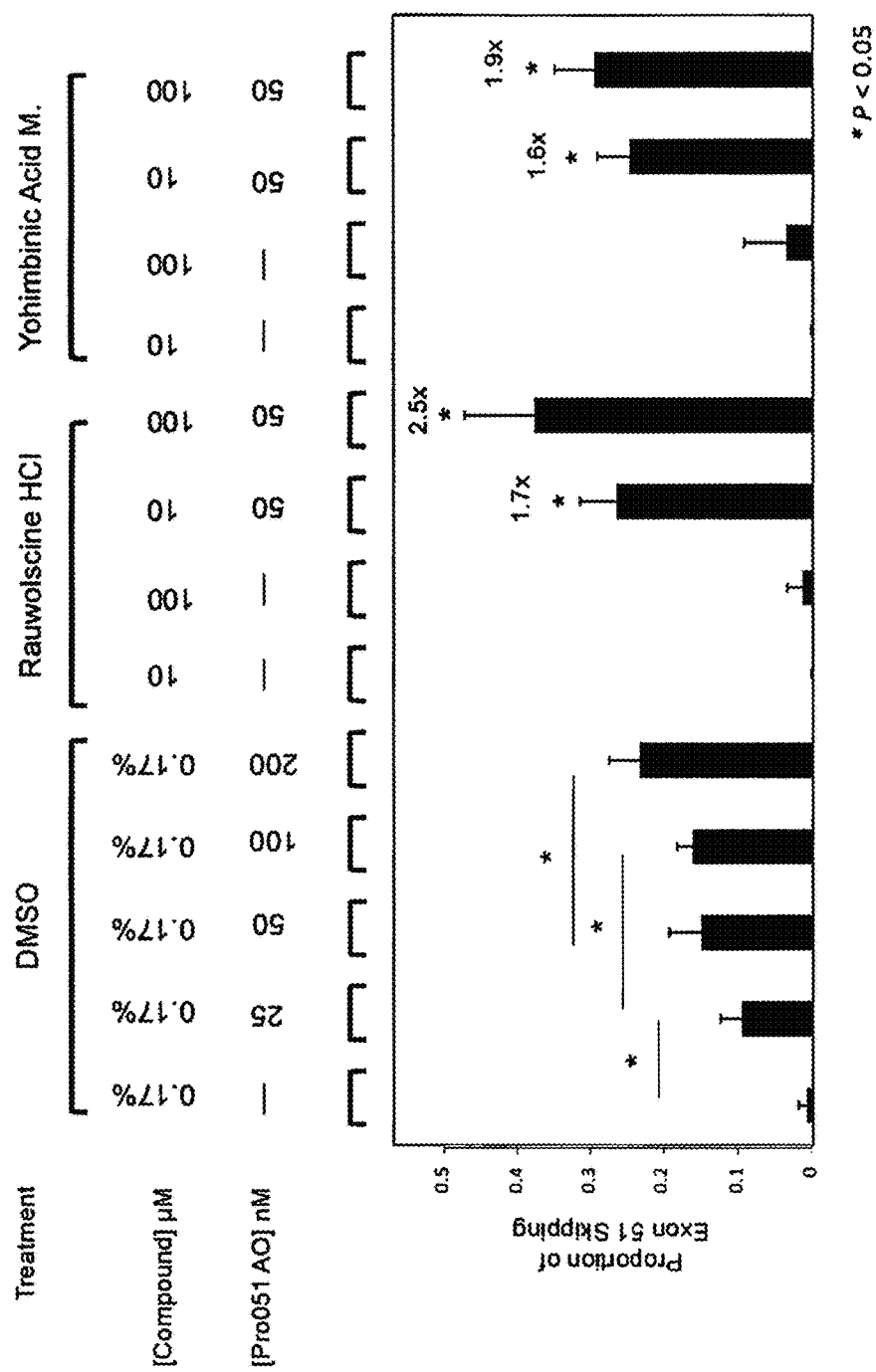

FIG. 17 shows that rauwolscine hydrochloride and yohimbinic acid monohydrate enhance AO directed DMD exon 51 skipping. As in FIG. 16, on day 7 of fusion, AO was added to iDRM05017s followed by the addition of Rauwolscine HCl, Yohimbinic acid monohydrate or vehicle (Dimethyl sulfoxide; DMSO) on Day 8. After two days total RNA was harvested, cDNA reverse transcribed and exon 51 skipping was detected by nested RT-PCR spanning exons 43-52. Quantitation of exon 51 skipping was performed using the Agilent Bioanalyzer and is represented as the proportion of exon 51 skipping. Error bars represent the SD of 3 independent wells.

Figure 18:
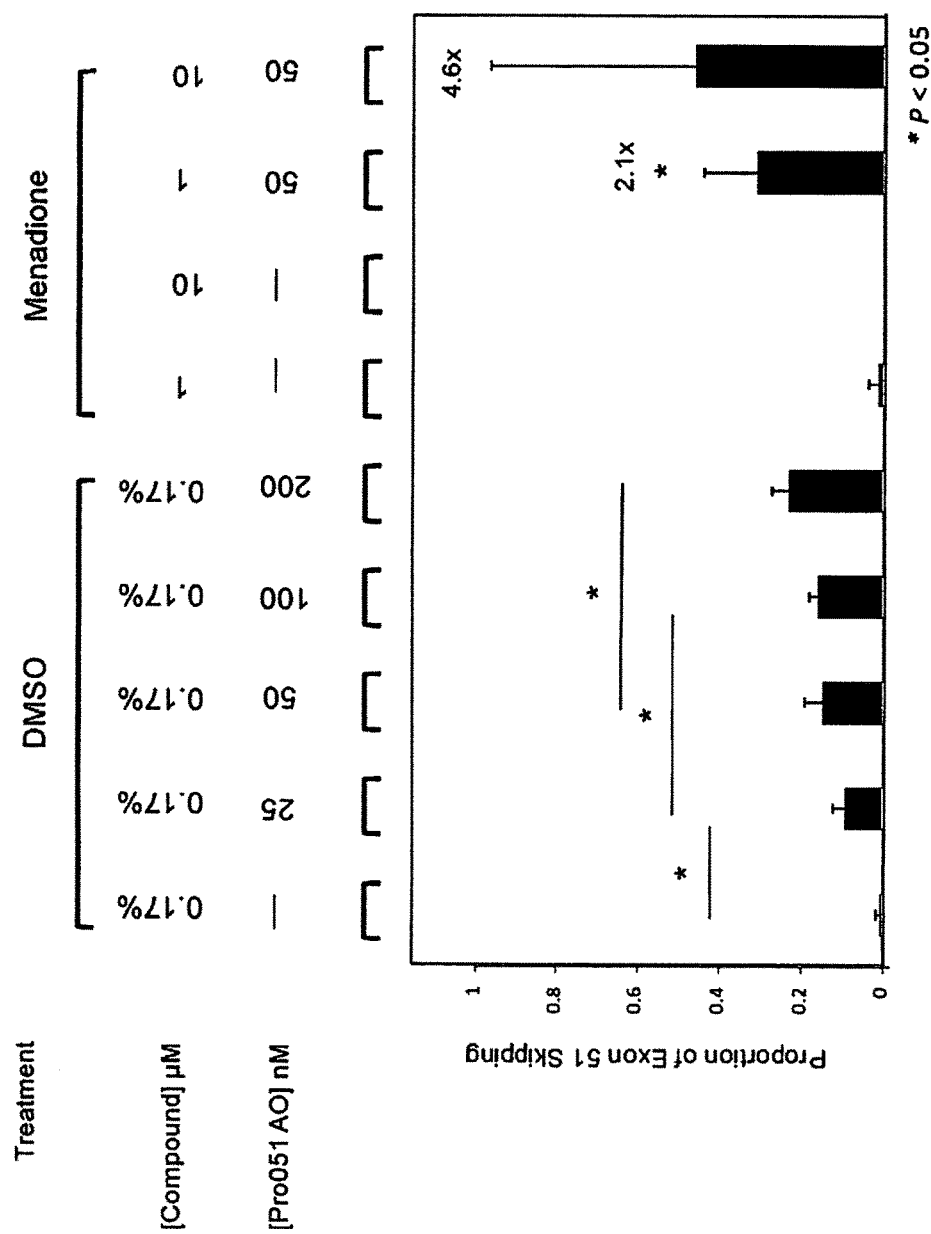

FIG. 18 shows that menadione enhances AO directed DMD exon 51 skipping. On day 7 of fusion, AO was added to iDRM05017s and twenty-four hours later removed and Menadione or vehicle (Dimethyl sulfoxide; DMSO) were added in fresh media. After two days total RNA was harvested, cDNA reverse transcribed with a DMD specific primer in exon 54, and exon 51 skipping was detected by nested RT-PCR spanning exons 43-52. Quantitation of exon 51 skipping was performed using the Agilent Bioanalyzer and is represented as the proportion of exon 51 skipping. Error bars represent the SD of 3 independent wells.

Figure 19:
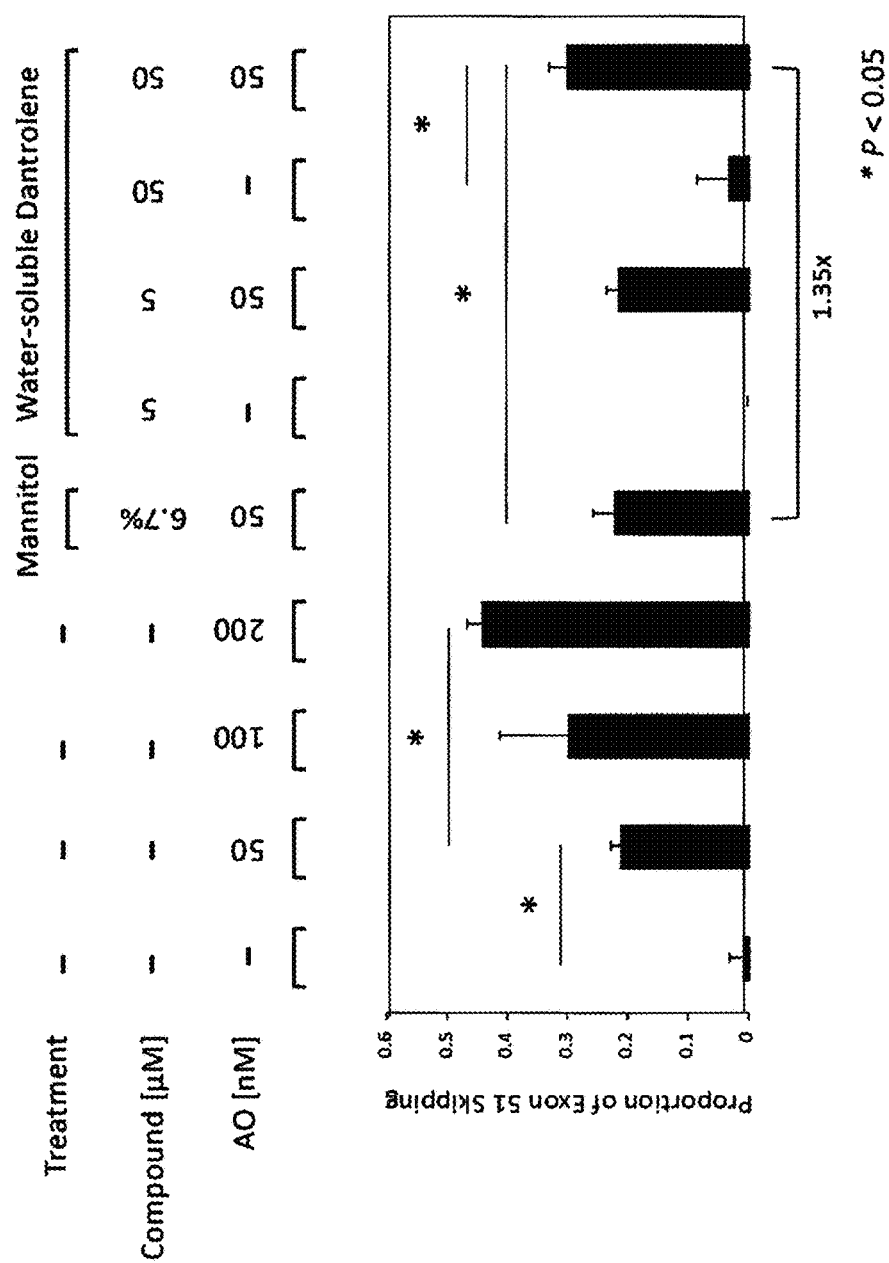

FIG. 19 shows that water-soluble dantrolene enhances AO directed DMD exon 51 skipping. On day 7 of fusion, AO was added to iDRM05017s and twenty-four hours later removed and water-soluble dantrolene (Revonto) or vehicle (6.7% Mannitol) were added in fresh media. After two days total RNA was harvested, cDNA reverse transcribed with a DMD specific primer in exon 54, and exon 51 skipping was detected by nested RT-PCR spanning exons 43-52. Quantitation of exon 51 skipping was performed using the Agilent Bioanalyzer and is represented as the proportion of exon 51 skipping. Error bars represent the SD of 3 independent wells.

Figure 20:
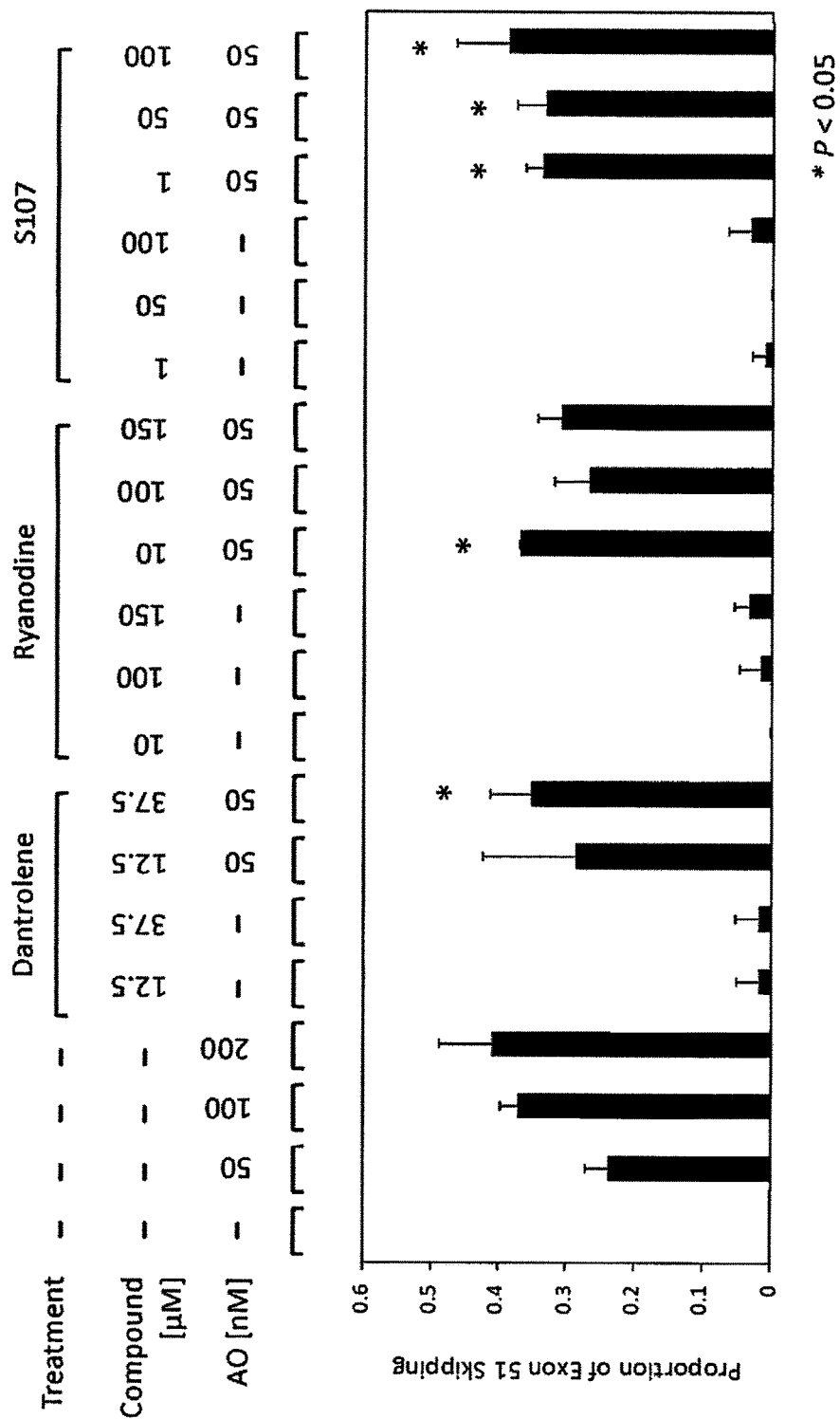

FIG. 20 shows that ryanodine receptor antagonists enhance AO directed DMD exon 51 skipping in a reprogrammed patient cell line. On day 7 of fusion, AO was added to iDRM05017s and twenty-four hours later removed and Dantrolene, Ryanodine, S107 or vehicle (Dimethyl sulfoxide; DMSO) were added in fresh media. After two days total RNA was harvested, cDNA reverse transcribed with a DMD specific primer in exon 54, and exon 51 skipping was detected by nested RT-PCR spanning exons 43-52. Quantitation of exon 51 skipping was performed using the Agilent Bioanalyzer and is represented as the proportion of exon 51 skipping. Error bars represent the SD of 3 independent wells.

Figure 21:
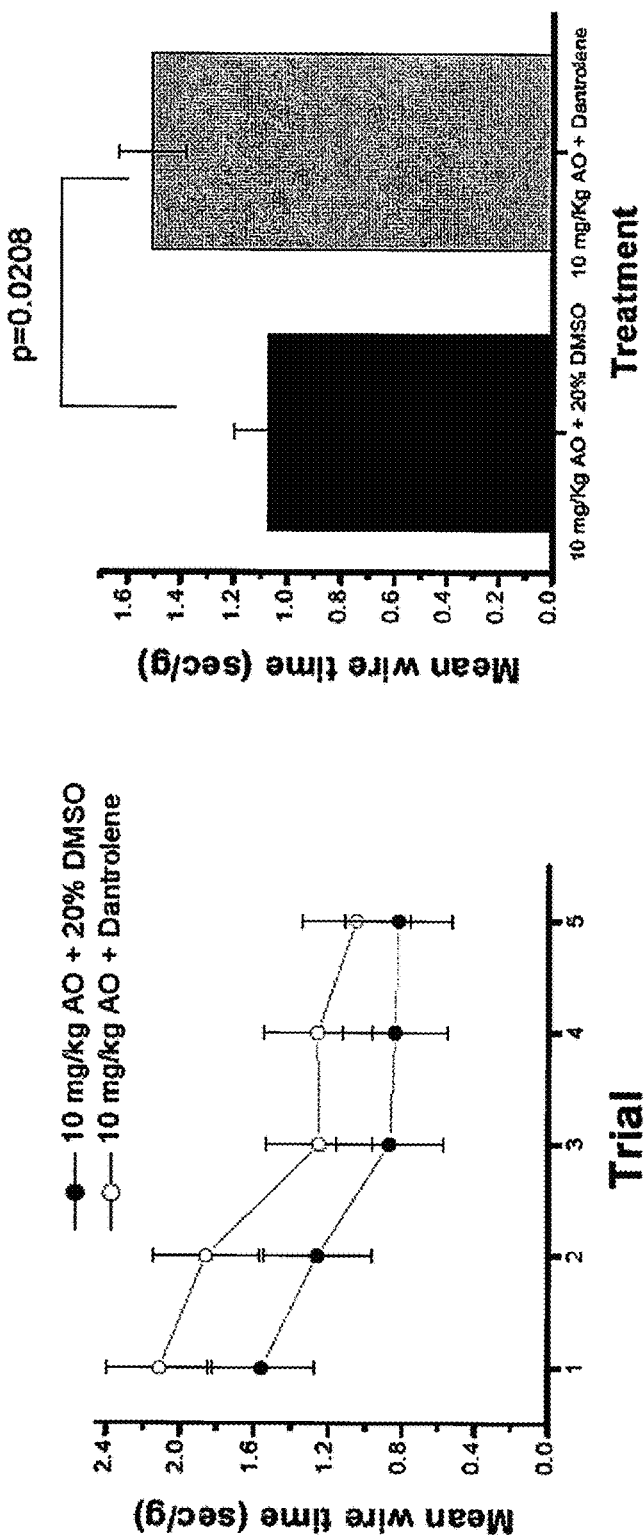

FIG. 21 shows that dantrolene synergizes with intravascularly delivered AO to increase muscle strength in mdx mice. Weekly systemic doses of saline, 10 mg/kg of morpholino M23D (+07-18) was administered intravascularly on Day 1, 8, and 15. Dantrolene or carrier (20% DMSO in saline) was administered intraperitoneally at a dose of 10 mg/kg/day in two divided doses daily. On Day 18 functional improvement was blindly assessed by using the taut wire test. Latency to fall (in seconds) was recorded for five consecutive trials, with a one minute break occurring in between each trial. Plotted is first the average across five trials, and then the normalized average (seconds/grams) across experimental groups. Error bars represent the s.e.m. There was a significantly increased ability of mdx mice to hang on wire (p=0.022).

DESCRIPTION OF EMBODIMENTS OF THE INVENTION

The present inventors identify herein low molecular weight compounds (sometimes referred to herein as "small molecules" or "small molecule compounds" or "compounds" of the invention) which block some forms of mRNA splicing and/or enhance (facilitate, augment) other forms of mRNA splicing. The types of splicing that can be regulated by a method of the invention include alternative splicing, in particular exon skipping. Depending on factors such as the splicing sequence and the gene or exon involved, this modulation of splicing can be accomplished in the presence of, or in the absence of, antisense oligonucleotides (AOs) that are specific for splicing sequences of interest. In embodiments of the invention, a small molecule and an AO of the invention act synergistically. The antisense molecules used in a method of the invention are sometimes referred to herein as antisense "splice switching oligonucleotides (SSO's)." Table 1 lists 27 representative small molecules which can be used in a method of the invention. It is to be understood that references herein to the 27 small molecules in Table 1 include pharmaceutically acceptable salts, hydrates, solvates or isomers thereof.

As shown in the Examples herein, the inventors performed a small molecule cell based screen using a human exon 50 (of the DMD gene) reporter cell line, which is activated when exon 50 is skipped. The cell line, which was adapted to allow the screening of thousands of compounds in multiple replicates, was obtained from Dr. Qi Lu. The compounds which were screened were selected from FDA approved libraries or known biologically active molecule libraries. Lead hits (shown in Table 1) were further validated using assessment of RNA sequence and with various dose titrations in mouse cells, and demonstrate synergy with antisense oligonucleotide. Each of the compounds was validated in counterscreens to rule out toxicity and autofluorescence, and demonstrated to have activity in 16 point titrations of the compound, either alone or in synergy with anti-sense oligonucleotide. The aggregate group of compounds defines new classes of drugs which induce (enhance) exon skipping. Some of the compounds are shown to increase the amount of skipped exon 50 dystrophin mRNA when applied externally to cells growing in culture either alone or in synergy with anti-sense oligonucleotide. One of the tested compounds, dantrolene, was demonstrated to affect mdx mice in vivo with systemic administration. Other studies presented herein also demonstate exon skipping of, e.g., exon 23 and exon 50 of DMD. It is expected that at least some of the compounds will induce (enhance) exon skipping and create alternate splice forms of proteins that are relevant to a variety of disease states.

Compounds that were identified in the counter screens include, e.g., Furaltadone hydrochloride, 5-iodotubericidin, bendroflumethiazide, cyclopiazonic acid, GW 5074, indirubin, rescinnamin, U-0126, acetopromazine maleate salt, Ro 31-8220. Additional compounds showing efficacy in counter screen and on mdx mouse myotubes include, e.g., dantrolene, dichlorobenzamil, ellipticine, fenbendazole, GF 109203X, halofantrine, niclosamide, pimozide, reserpine, syringospine. Other compounds shown or expected to show exon skipping activity include, e.g., Ryanodine, RyCal S107, piperacetazine, fluphenazine dihydrochloride, trifluorperazine dihydrochloride, yohimbinic acid, and menadione. Pharmaceutically acceptable salts, hydrates, solvates or isomers of these or other compounds of the invention are also included. For example, sodium ions in the formulas can be substituted with any of a variety of other pharmaceutically acceptable cations. Suitable such salts, hydrates, solvates or isomers will be evident to a skilled worker. See, e.g., Remington's Pharmaceutical Sciences, 18$^{th}$ edition (1990, Mack Publishing Co., Easton, Pa.).

TABLE 1

| Compound Name | FDA Approved | Molecular Weight | General Chemical Type | Known Activity | Routes of Admission | Linear Chemical Structure | Chemical Structure |
|---|---|---|---|---|---|---|---|
| Furaltadone hydrochloride | N (as of 1991) but is in the FDA library | 324.29 | Antibiotic | Characterized by the Nitrofuran ring. Effective antibiotic when all others fail against extremely drug resistant bacterial infections but has many side effects. | PO only | $C_{13}H_{16}N_4O_6$ | 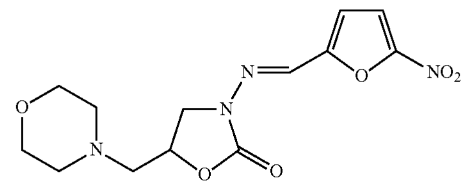 [SMILES: O=C1OC(CN2CCOCC2)CN1/N=C/c1ccc([N+](=O)[O-])o1] |
| 5-IODO-TUBERCIDIN | N | 392.15 | Kinase Inhibitor | Inhibits ERK2 (Ki = 525 nm) also inhibits adenosine kinase (Ki = 30 nM) CK1 and CK2 and insulin receptor kinase2. | — | $C_{11}H_{13}IN_4O_4$ | 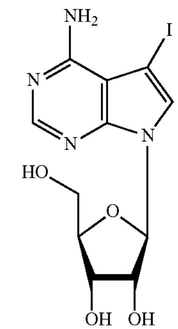 |
| Bendroflume-thiazide | Y | 421.41 | Antihypertensive Agents, Diurectics, Sodium Chloride Symporter Inhibitors | Inhibits active chloride reabsorption at the early distal tubule via the Na—Cl cotransporter, resulting in an increase in the excretion of sodium, chloride, and water. Also inhibits sodium ion transport across the renal tubular epithelium through binding to the thiazide sensitive sodium-chloride transporter. The antihypertensive mechanism of bendroflumethiazide is less well understood although it may be mediated through its action on carbonic anhydrases in the smooth muscle or through its action on the large-conductance calcium-activated potassium (KCa) channel. | PO | $C_{15}H_{14}F_3N_3O_4S_2$ | 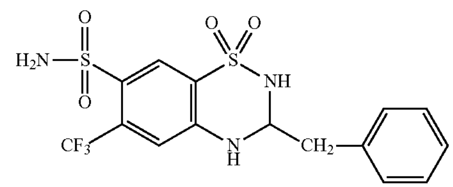 [SMILES: NS(=O)(=O)c1cc2c(cc1C(F)(F)F)NC(Cc1ccccc1)NS2(=O)=O] |

TABLE 1-continued

| Compound Name | FDA Approved | Molecular Weight | General Chemical Type | Known Activity | Routes of Admission | Linear Chemical Structure | Chemical Structure |
|---|---|---|---|---|---|---|---|
| CYCLO-PIAZONIC ACID | N | 336.38 | Fungal secondary metabolite | Induces the release of intracellular stored Ca2+, without increasing IP3 levels, via inhibition of endoplasmic reticulum Ca2+−ATPase. It is a highly specific inhibitor of the Ca2+−ATPase of sarcoplasmic reticulum, completely inhibiting the enzyme at 6-8 nmol/mg protein (at 0.5-2 μM ATP). | — | $C_{20}H_{20}N_2O_3$ | 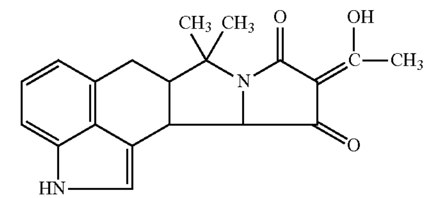 [SMILES: C/C(O)=C1\C(=O)C2C3c4c[nH]c5cccc(c45)CC3C(C)(C)N2C1=O] |
| GW 5074 | N | 520.94 | Enzyme Inhibitor | Potent and selective cell permeable inhibitor of cRAF1 kinase (IC50 = 9 nM) with 100-fold selectivity over CDK1, CDK2, c-src, ERK2, MEK, p38, Tie2, VEGFR2 and c-fm. | — | $C_{15}H_8Br_2INO_2$ | 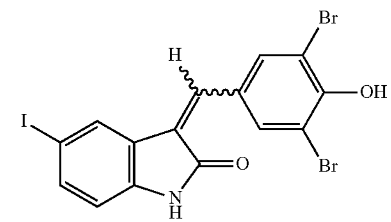 |
| INDIRUBIN | Y | 277.28 | Kinase Inhibitor | Cyclin-dependent kinase inhibitor which functions by competing with ATP for binding to the catalytic subunit. Inhibits CDK1, CDK2, CDK4, and CDK5. | IV, IP | $C_{16}H_{11}N_3O_2$ | 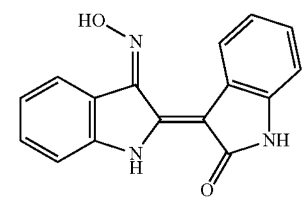 [SMILES: O=C1Nc2ccccc2/C1=C1/Nc2ccccc2/C1=N\O] |
| Rescinnamin | Y | 634.72 | Antihypertensive agent | Angiotensin-converting enzyme inhibitor used as an antihypertensive drug. Also is a reserpine analog. | PO | $C_{35}H_{42}N_2O_9$ | 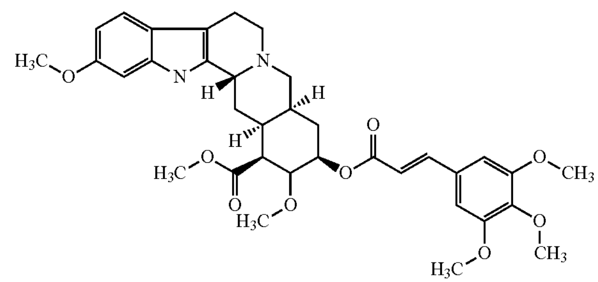 |

TABLE 1-continued

| Compound Name | FDA Approved | Molecular Weight | General Chemical Type | Known Activity | Routes of Admission | Linear Chemical Structure | Chemical Structure |
|---|---|---|---|---|---|---|---|
| U-0126 | N (in pre-clinical trials currently) | 426.56 | Enzyme Inhibitor | A novel, potent and selective MEK inhibitor, MEK1 IC50 = 72 nM, MEK2 IC50 = 58 nM. Also inhibits MAPKK. In pre clinical trials for cancer treatments. | IV | $C_{18}H_{16}N_6S_2 \cdot C_2H_5OH$ | 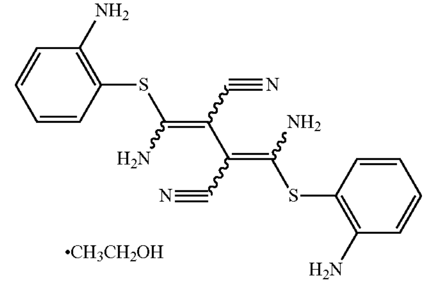 [SMILES: N#CC(=C(N)Sc1ccccc1N)C(C#N)=C(N)Sc1ccccc1N ; "·CH3CH2OH"] |
| Acetopromazine maleate salt | Y | 442.53 | Antipsychotic Agents | Dopamine antagonist. | IM, SC | $C_{19}H_{22}N_2OS \cdot C_4H_4O_4$ | 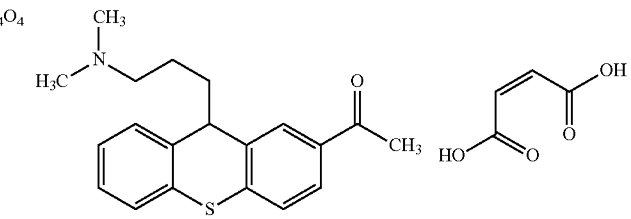 |
| Ro 31-8220 | N | 553.65 | Enzyme Inhibitor | Inhibitor of GRK-5 (G protein-coupled receptor kinase); PKC (protein kinase C); MAPKAP kinase 1β and p70 kinase. | PO | $C_{25}H_{23}N_5O_2S \cdot CH_3SO_3H$ | 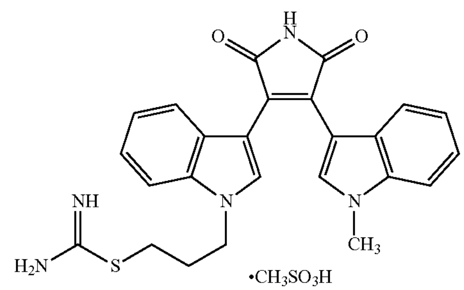 |
| DANTROLENE | Y | 336.23 | Muscle relaxant, Intracellular calcium channel modulator | Inhibitor of $Ca^{2+}$ release from sarcoplasmic reticulum; muscle relaxant. Dantrolene depresses excitation-contraction coupling in skeletal muscle by binding the ryanodine receptor and decreasing intracellular calcium concentration. | PO, IV, IM | $C_{14}H_9N_4NaO_5$ | 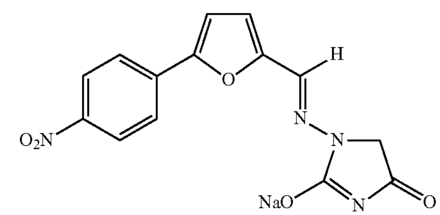 |

TABLE 1-continued

| Compound Name | FDA Approved | Molecular Weight | General Chemical Type | Known Activity | Routes of Admission | Linear Chemical Structure | Chemical Structure |
|---|---|---|---|---|---|---|---|
| DICHLORO-BENZAMIL | N | 425.1 | Calcium Channel Modulator | Inhibits cyclic nucleotide-gated Ca+2 channels (IC50 = 38-50 μM). Inhibits plasmalemmal Na+/Ca+2 and Na+/H+ exchange (IC50 = 10 μM). Blocks caffeine-induced current (by blocking Na+/Ca+2 exchange) at 50-100 μM). Nonselective cation channel blocker (25 μM) | — | $C_{13}H_{12}N_7OCl_3 \cdot HCl$ | 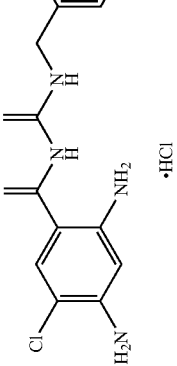 |
| Ellipticine | Y | 246.31 | Antineoplastic Agent, Uncoupling Agent | Antitumor alkaloid isolated from *Ochrosia* sp. It inhibits cytochrome P450 (CYP1A1) and DNA topoisomerase II activites. | PO, IP | $C_{17}H_{14}N_2$ | 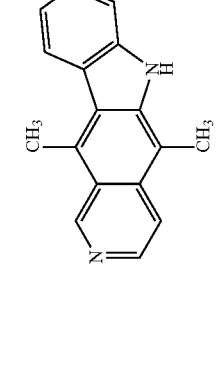 |
| Fenbendazole | Y | 299.35 | Antinematodal agent | Inhibits cytoplasmic microtubules in the intestinal or absorptive cells of worms, thus inhibiting glucose uptake and glycogen storage depletion, leading to death of the worms within days. | PO, IV | $C_{15}H_{13}N_3O_2S$ | 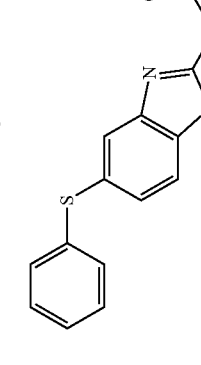 |
| GF 109203X | N | 412.48 | Kinase Inhibitor | Inhibitor or protein kinase C; potent inhibitor of GSK-3. | — | $C_{25}H_{24}N_4O_2$ | 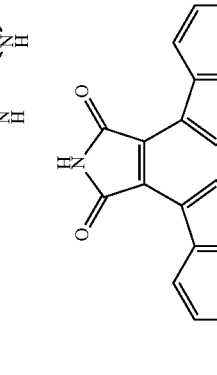 |

TABLE 1-continued

| Compound Name | FDA Approved | Molecular Weight | General Chemical Type | Known Activity | Routes of Admission | Linear Chemical Structure | Chemical Structure |
|---|---|---|---|---|---|---|---|
| Halofantrine hydrochloride | Y | 536.88 | Antimalarial agent | Halofantrine is a blocker of delayed rectifier potassium current via the inhibition of hERG channel. It is a blood schizontocide that is active against chloroquine-resistant falciparum and vivax malaria. It can destroy asexual blood forms and inhibit the proton pump. | PO | $C_{26}H_{30}Cl_2F_3NO \cdot HCl$ | 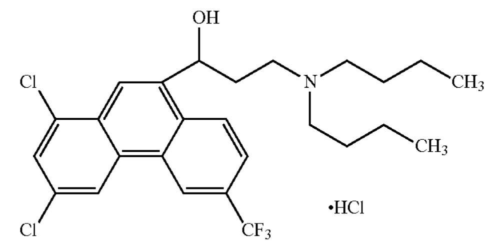 [SMILES: CCCCN(CCCC)CCC(O)c1cc2c(Cl)cc(Cl)cc2c2cc(C(F)(F)F)ccc12 ; Cl] |
| Niclosamide | Y | 327.12 | Anticestodal, Antinematodal, Molluscacidades | Niclosamide uncouples oxidative phosphorylation in mitochondria of the tapeworm. It belongs to the class of alicyclic acid derivatives agents used as anticestodals. | PO | $C_{13}H_8Cl_2N_2O_4$ | 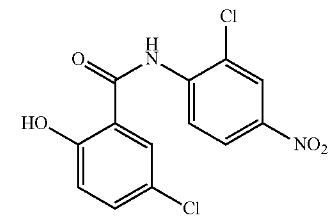 [SMILES: O=C(Nc1ccc([N+](=O)[O-])cc1Cl)c1cc(Cl)ccc1O] |
| PIMOZIDE | Y | 461.55 | Antipsychotic | $D_2$ dopamine receptor antagonist; binds with high affinity to the cloned 5-$HT_7$ receptor; $Ca^{2+}$ channel antagonist; antipsychotic. | PO | $C_{28}H_{29}F_2N_3O$ | 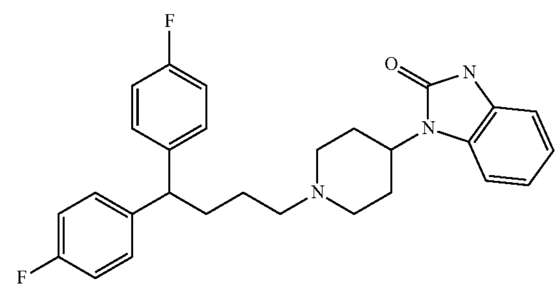 [SMILES: O=c1[nH]c2ccccc2n1C1CCN(CCCC(c2ccc(F)cc2)c2ccc(F)cc2)CC1] |

TABLE 1-continued

| Compound Name | FDA Approved | Molecular Weight | General Chemical Type | Known Activity | Routes of Admission | Linear Chemical Structure | Chemical Structure |
|---|---|---|---|---|---|---|---|
| Reserpine | Y | 608.58 | Antihypertensive, Antypsychotic | Reserpine is an antihypertensive drug that causes depletion of nonradrenaline, catechlamine and serotonin stores resulting in a reduction in BP, bradycardia and CNS depression. It belongs to the class of rauwolfia alkaloids, centrally-acting antiadrenergic agents. Used in the treatment of hypertention. Reserpine can also be utilized in the relief of symptoms in agitated psychotic states (e.g. schizophrenia). | PO, or injectable | $C_{33}H_{40}N_2O_9$ | 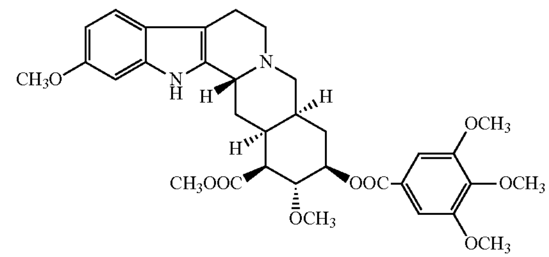 |
| Syrosingopine | Y | 666.71 | Antihypertensive agent | Syrosingopine is prepared from reserpine by hydrolysis and reesterification; an antihypertensive agent with actions similar to those of reserpine | PO, or injectable | $C_{35}H_{42}N_2O_{11}$ | 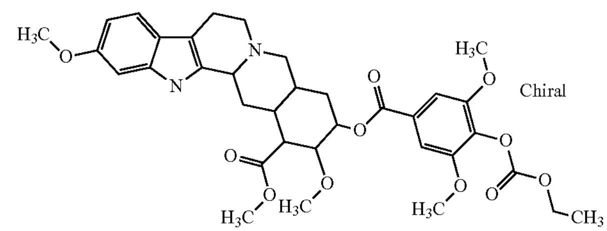 [SMILES: CCOC(=O)Oc1c(OC)cc(C(=O)OC2CC3CN4CCc5c([nH]c6cc(OC)ccc56)C4CC3C(C(=O)OC)C2OC)cc1OC] |
| Ryanodine | | | | | | | 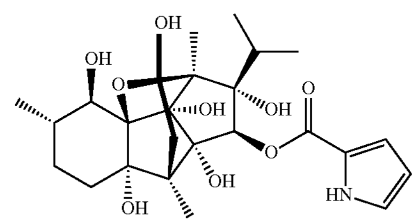 |
| RyCal S107 | | | | | | | 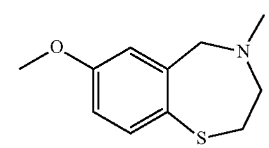 |

TABLE 1-continued
| Compound Name | FDA Approved | Molecular Weight | General Chemical Type | Known Activity | Routes of Admission | Linear Chemical Structure | Chemical Structure |
|---|---|---|---|---|---|---|---|
| piperacetazine | | | | | | | 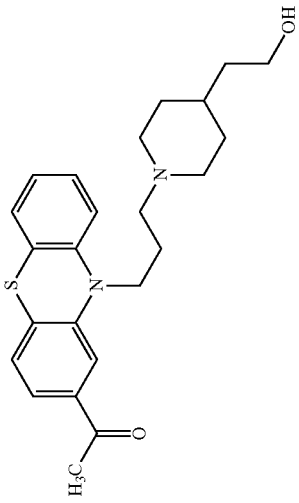 |
| Fluphenazine dihydrochloride | | | | | | | 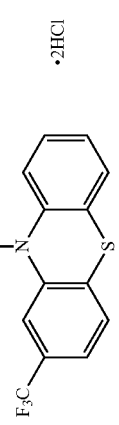 |
| Trifluoperazine dihydrochloride | | | | | | | 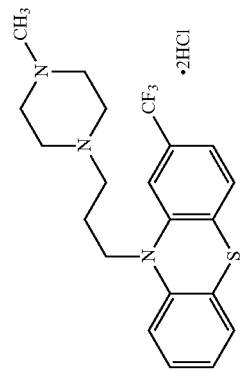 |

TABLE 1-continued
| Compound Name | FDA Approved | Molecular Weight | General Chemical Type | Known Activity | Routes of Admission | Linear Chemical Structure | Chemical Structure |
|---|---|---|---|---|---|---|---|
| Yohimbinic acid | | | | | | | 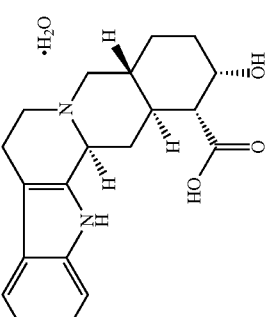 |
| Menadione | | | | | | | 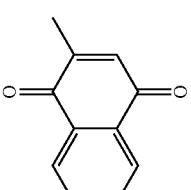 |

Each of the identified compounds has a different known effect on cells and has been used for different therapeutic purposes. How each of the compounds affects the RNA splicing machinery to alter the efficiency of exclusion of targeted exons is not known at this time. While the detailed molecular mechanisms are not yet established, several of the compounds identified, for instance Dantrolene, have well-characterized effects in cells and in humans. Dantrolene's known effect is to block the ryanodine receptor which prevents release of calcium that is needed for muscle cell contraction when excited. This drug is used clinically to mitigate the effects of malignant hyperthermia. The use of Dantrolene in combination with antisense oligonucleotide to induce an inframe transcript is a novel use for this compound. Dantrolene has been tried as a single agent to treat Duchenne muscular dystrophy without significant beneficial effect and without significant deleterious effects. None of the identified compounds has been used in order to alter exon splicing therapeutically. For example, some of these compounds are known vermicidal s, anti-hypertensive, anti-malarial, anti-psychotic or anti-cancer agents.

It is expected that endogenously generated antisense oligonucleotides (for instance from gene delivery) will augment exon skipping in a similar manner as exogenously administered AOs. For example, endogenously generated small nuclear RNA (sRNA) carrying appropriate antisense sequences and transcribed from, e.g., a U7 snRNA-based gene construct can be used in a method of the invention.

Advantages of methods and combinations of the invention include that they augment the efficiency of exon skipping (e.g., when performed in the presence of AO) and thus allow a sufficient amount of skipping to be therapeutically relevant and/or reduce the cost resulting from high doses and repeated administration of expensive AOs.

"Antisense-mediated exon skipping," as used herein, refers to an approach that uses antisense oligonucleotides (AOs) to modulate splicing by blocking (hiding) specific sequence motifs in the pre-mRNA (sometimes referred to herein as "splicing sequences") essential for exon inclusion from the splicing machinery. AOs that block aberrant splice sites can restore normal splicing. Alternatively, AOs targeting certain splicing sequences can switch splicing patterns from detrimental to beneficial isoforms or can convert at least partially non-functional mRNAs into functional mRNA. An example of the latter approach is the restoration of a disrupted reading frame, thereby generating semi-functional proteins instead of non-functional proteins.

A compound of the invention can be used to block splicing at a site of interest by specifically interacting with (e.g., binding to) a splicing sequence at that site, either directly or indirectly. By a "splicing sequence" is meant a sequence that regulates and/or is required for splicing out of a particular intron and/or the retention of a particular exon. The splicing sequence can be, for example, a splice donor site, a splice acceptor site, a branch site, an intronic splicing enhancer (ISE), an exonic splicing enhancer (ESE), an intronic splicing silencer or an exonic splicing silencer.

An AO used in a method of the invention can bind directly and specifically to a target splicing sequence of interest. By "specific binding" is meant that the AO binds preferentially to the target sequence of interest, but not to non-target sequences under conditions in which specific binding is desired. The conditions can be, e.g., physiological conditions in the case of in vivo assays or theraprutic treatment, and for in vitro assays, conditions in which the assays are performed. Because the mechanism by which small molecule compounds of the invention block splicing (e.g., enhance exon skipping) is not known for all of the compounds, it is not known whether the compound binds directly to a splice site or acts indirectly (e.g., by binding to another RNA or protein element of a spliceosome). Regardless of the mechanism, a compound of the invention that "specifically" blocks a splicing event of interest is one that preferentially blocks the particular splicing event but does not block non-targeted splicing events, under conditions in which specific blocking is desired.

As used herein, the term "antisense oligonucleotide (AO)" refers to a single-stranded oligonucleotide that is specific for, and complementary to, a splicing sequence of interest, and accordingly is capable of hydrogen bonding to the sequence. One of skill in the art can readily design AOs to be specific for suitable target sequences, many of which are well-known in the art. For example, one can access pre-mRNA sequences comprising suitable splicing sequences in publications or in annotated, publically available databases, such as the GenBank database operated by the NCBI. A skilled worker will be able to design, make and use suitable antisense oligonucleotides, based on these or other sequences, without undue experimentation. A number of AO's have been designed for enhancing exon skipping and some are currently in preclinical or clinical trials. Any of these AOs is suitable for use in a method of the invention.

An antisense nucleic acid may be, e.g., an oligonucleotide, or a nucleic acid comprising an antisense sequence that is operably linked to an expression control sequence and that is expressed in a cell.

Antisense oligonucleotides may have a variety of different backbone chemistries, such as morpholino phosphorodiamidate (PMO) or 2'-O-methyl' or peptide nucleic acids, etc., which stabilize them. For example, it can be DNA, RNA, PNA or LNA, or chimeric mixtures or derivatives or modified versions thereof. The nucleic acid can be modified at the base moiety, sugar moiety, or phosphate backbone, using conventional procedures and modifications. Modifications of the bases include, e.g., methylated versions of purines or pyrimidines. Modifications may include other appending groups that will be evident to a skilled worker.

Antisense oligonucleotides can be constructed using chemical synthesis procedures known in the art. An AO can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. For guidance in methods of synthesizing AOs used in methods of the present invention, see, e.g.:

For guidance in methods of synthesizing morpholino AO's for use in the present invention, see, e.g., US patent application 2009/0131624 ("Synthesis of morpholino oligomers using double protecte guanine morpholino subunits").

For guidance in synthesizing oligonucleotides, see, e.g., Gough et al. (1979) *Nucleic Acids Research* 7, 1955-1964; Hata et al. (1983) *Tetrahedron Lett.* 24, 2775-2778; Jones et al. (1982A *Tetrahedron Lett.* 23, 2253-2256; Jones et al. (1982) *Tetrahedron Lett.* 23, 2257-2260; O. Mitsunobu (1981) *Synthesis* 1, 1-28; Reese et al. (1981) *Tetrahedron Lett.* 22, 4755-4758; Reese et al. (1984) *J. Chem. Soc., Perkin Trans.* 11263-1270; Summerton et al. (1993) U.S. Pat. No. 5,185,444; Summerton et al. (1997) *Antisense Nucl. Acid Drug Dev.* 7(3), 187-195.

For guidance in synthesizing 2-O-methyl' oligos, see e.g. Verma et al. (1998) MODIFIED OLIGONUCLEOTIDES: Synthesis and Strategy for Users, *Annu. Rev. Biochem.* 67, 99-134

For guidance in synthesizing dantrolene, see e.g. Oleinik et al. (1984) *Pharmaceutical Chemistry Journal* 18 (5), 310-312.

To enhance exon skipping in cells in culture, AO's can be added to cells in culture media. Typically, synthetic oligonucleotides are added to a final concentration of about 10 nM to about 10 microM, e.g., about 50 nM to about 1000 nM (e.g., at increments of 10 nM within the indicated ranges). The term "about" a particular value, as used herein, means plus or minus 10% of the indicated value.

Effective doses of AOs for in vivo administration can be determined, e.g., on the basis of the amounts used for exon skipping in the absence of a small molecule of the present invention. Many AO's have been administered to subjects in the absence of small molecule compounds of the invention, and doses have been established which are at least partially effective and are non-toxic to the subjects. In general, doses of AOs ranging from about 5-100 mg/kg/wk IV (intravenous) (or comparable amounts for other modes of admin) are effective for inducing at least a detectable amount of dystrophin expression with targeted removeal of a given exon.

Alternatively, an antisense oligonucleotide can be produced biologically using an expression vector into which a nucleic acid has been subcloned in an antisense orientation (i.e., nucleic acid transcribed from the inserted nucleic acid will be of an antisense orientation to a target sequence of interest). Expression control sequences (e.g., regulatory sequences) operatively linked to a nucleic acid cloned in the antisense orientation can be chosen which direct the expression of the antisense RNA molecule in a cell of interest. For instance, promoters and/or enhancers or other regulatory sequences can be chosen which direct constitutive, tissue specific or inducible expression of an AO. Inducible expression of antisense RNA, regulated by an inducible eukaryotic regulatory system, such as the Tet system (e.g., as described in Gossen et al. (1992) *Proc. Natl. Acad. Sci. USA* 89, 5547-5551; Gossen et al. (1995) *Science* 268, 1766-1769; PCT Publication No. WO 94/29442; and PCT Publication No. WO 96/01313) can be used. The antisense expression vector can be in the form of, for example, a recombinant plasmid, phagemid or attenuated virus. Suitable viral vectors include, e.g., adeno-associated virus (AAV) or lentivirus vectors. The antisense expression vector can be introduced into cells using standard techniques well known in the art. For guidance in using AAV vectors for introducing antisense molecules into mdx mice, see e.g. Denti et al. (2008) *Hum Gene Ther* 19, 601-608 or Incitti et al. (2010) *Mol. Ther.* 18, 1675-1682.

In one embodiment of the invention, an RNA molecule that comprises the sequence antisense to a splicing sequence in, e.g., the dystrophin pre-mRNA, is produced biologically by using an expression vector into which a nucleic acid has been subcloned. Expression control sequences (e.g. regulatory sequences) operably linked to the cloned nucleic acid can be chosen which direct the expression of the antisense RNA molecule comprising the sequence antisense to a splicing sequence in, e.g., dystrophin pre-mRNA, in a cell of interest. The RNA molecule may comprise, e.g., a U1 snRNA, U2 snRNA, U6 snRNA or U7 snRNA. Without wishing to be limited by any particular mechanism, it is suggested that expression of the snRNA generates an snRNP particle which then binds to the target sequence in dystrophin pre-mRNA via the complementary fragment of snRNA.

Any of the types of expression control sequences described in the previous paragraph can be used to direct the expression of the desired RNA in this embodiment.

In one embodiment of the invention, an AO comprises a strand that is completely complementary (100% identical in sequence) to a splicing sequence that it is designed to inhibit. That is, every contiguous nucleotide in the AO is hybridized to every nucleotide in a splicing sequence. However, 100% sequence identity between the AO and the target splicing sequence is not required to practice the present invention. Thus, the invention has the advantage of being able to tolerate naturally occurring sequence variations that might be expected due to genetic mutation, strain polymorphism, or evolutionary divergence. Alternatively, the variants may be artificially generated. Nucleic acid sequences with, e.g., small insertions, deletions, and single point mutations relative to the target sequence can be effective for inhibition. The degree of sequence identity can be, e.g., 95%, 98%, 99%, or 100%. Such a variant AO must, of course, retain the relevant activity of the AO from which it is derived. (e.g., the ability to suppress splicing at a site of interest). Such variants are sometimes referred to herein as "active variants."

The length of an AO may vary, provided that it is capable of binding selectively to the intended splicing sequence within the pre-mRNA molecule. A skilled worker can readily determine a satisfactory length. Generally, an AO is from about 10 nt in length to about 50 nt in length. Any length of nucleotides within this range, including the endpoints, can be used in a method of the invention. In one embodiment, the length of the AO is about 17-30 nt in length.

For further guidance for designing suitable antisense molecules that are complementary to a region of a pre-mRNA involved in splicing (thereby blocking splicing), and for methods for making and delivering such molecules to a cell or a subject, see, e.g., US 2008/0200409 or U.S. Pat. Nos. 7,973,015, 7,960,541, 7,902,160, 7,888,012, 7,879,992 or 7,737,110.

A method of the invention can be carried out in vitro (e.g., to elucidate the mechanism by which splicing occurs, such as to reveal novel molecular interactions in the processing of mRNA; or to screen for compounds that can block a splicing event and thus, for example, enhance exon skipping).

In another embodiment of the invention, the method is carried out in a subject, in vivo. A "subject," as used herein, can refer to any animal which is subject to a disease or condition that can be treated by a method of the invention. Suitable subjects include, e.g., a mammal, such as an experimental animal or disease model, a farm animal, pet, or the like. In some embodiments, the animal is a primate, for example a human.

In some embodiments of the invention, a subject is treated with an effective amount of a compound of the invention, or with a combination of a compound of the invention and a suitable AO, each of which is designed to block a splicing event of interest. An "effective amount" of a compound (or combination) of the invention is an amount that is effective to elicit a measurable amount of biological activity, e.g. a measurable amount of enhancement of exon skipping (in some embodiments in the absence of AOs, and in some embodiments in the presence of a suitable AO). Preferably, an effective amount of a compound or combination of the invention does not elicit substantial amounts of undesirable (e.g., toxic) effects. The enhancement can occur prophylactically (e.g. preventively, to inhibit the development of the disorder), or in a subject who already has the condition. For example, treatment by a method of the invention can ameliorate one or more symptoms of the condition.

A skilled worker will recognize a variety of conditions that can be treated by a method of the invention. A probabilistic analysis indicated that over 60% of human disease-causing mutations affect splicing rather than directly affecting coding sequences (Lopez-Bigas et al. (2005) *FEBS Letters* 579, 1900-3). See also Wang et al. (2007), Splicing in disease: disruption of the splicing code and the decoding machinery, *Nature Reviews Genetics* 8, 749-761 and Singh et al. (2012), Pre-mRNA splicing in disease and therapeutics, *Trends in Molecular Medicine* 18, (8), 472-482. Diseases associated with aberrant splicing or missplicing that can be inhibited by a method of the invention include e.g. beta-thalassemia and certain forms of cancers. Alternatively, exon skipping by a method of the invention can remove exons that contain mutations which are associated with diseases, such as mutations that alter the reading frame of the protein encoded by an mRNA. These conditions include, e.g., DMD, as described above (changing DMD dystrophin to a more functional form of dystrophin, in effect converting Duchenne MD into Becker MD). One embodiment of the invention is a method for treating a subject that has Duchenne muscular dystrophy (DMD), or is a non-human model of DMD, comprising administering to the subject an effective amount of small molecule selected from the compounds shown in Table 1, in conjunction with an AO specific for modulating splicing of dystrophin pre-mRNA, such as one for exon 23, 44, 45, 50, 51, 52, or 53 of the DMD gene. The exon skipping can be either single or multi-exon skipping (e.g., skipping of many possible 2-10 exon combinations that will be evident to a skilled worker).

Some suitable exons that can be skipped by a method of the invention are summarized in Table 6 below. Listed are human DMD coding sequences with 50 intronic nucleotides at the exon boundaries. mRNA sequences are in upper case, and intronic sequences in lower case. On the basis of these sequences, a skilled worker can readily design AO's specific for blocking the relevant splice sites.

TABLE 6

```
    Exon 1 (SEQ ID NO: 18)
  1 ATGCTTTGGT GGGAAGAAGT AGAGGACTGT Tgtaagtaca aagtaactaa aaatatattt
    tactgtggca taacgtttag t Exon 2 (SEQ ID NO: 19)
  1 ttatatttaa agttgcttcc taacttttat tttttttattt tgcattttag ATGAAAGAGA
    AGATGTTCAA AAGAAAACAT TCACAAAATG GGTAAATGCA 101 CAATTTTCTA AGgtaagaat ggtttgttac tttactttta agatctaagt tgtgaaattt
    tc Exon 3 (SEQ ID NO: 20)
  1 atcattggaa gtgtgctttg ttaaattgag tgtatttttt ttaatttcag TTTGGGAAGC
    AGCATATTGA GAACCTCTTC AGTGACCTAC AGGATGGGAG 101 GCGCCTCCTA GACCTCCTCG AAGGCCTGAC AGGGCAAAAA CTGgtatgtg acttattttt
    aagaaagtta actttaaact tagtagaatt tca Exon 4 (SEQ ID NO: 21)
  1 attgtcggtc tctctgctgg tcagtgaaca ctcttttgtt ttgttctcag CCAAAAGAAA
    AAGGATCCAC AAGAGTTCAT GCCCTGAACA ATGTCAACAA 101 GGCACTGCGG GTTTTGCAGA ACAATAATgt aagtagtacc ctggacaagg tctggatgct
    gtgacacagc atgcttca Exon 5 (SEQ ID NO: 22)
  1 ctaggcattt ggtctcttac cttcaaatgt tttaccccctt tctttaacag GTTGATTTAG
    TGAATATTGG AAGTACTGAC ATCGTAGATG GAAATCATAA 101 ACTGACTCTT GGTTTGATTT GGAATATAAT CCTCCACTGG CAGgtaagaa tcctgatgaa
    tggtttcctt ttgggtaaca ttaatcttgt ttt Exon 6 (SEQ ID NO: 23)
  1 ttcttgctca aggaatgcat tttcttatga aaatttattt ccacatgtag GTCAAAAATG
    TAATGAAAAA TATCATGGCT GGATTGCAAC AAACCAACAG 101 TGAAAAGATT CTCCTGAGCT GGGTCCGACA ATCAACTCGT AATTATCCAC AGGTTAATGT
    AATCAACTTC ACCACCAGCT GGTCTGATGG CCTGGCTTTG 201 AATGCTCTCA TCCATAGTCA TAGgtaagaa gattactgag acattaaata acttgtaaaa
    gtggtgattt aga Exon 7 (SEQ ID NO: 24)
  1 gattgattta tatttgtctt tgtgtatgtg tgtatgtgta tgtgttttag GCCAGACCTA
    TTTGACTGGA ATAGTGTGGT TTGCCAGCAG TCAGCCACAC 101 AACGACTGGA ACATGCATTC AACATCGCCA GATATCAATT AGGCATAGAG AAACTACTCG
    ATCCTGAAGg ttggtaaatt tctggactac cactgctttt 201 agtatggtag agtttaatg Exon 8 (SEQ ID NO: 25)
  1 tctcaaatat agaaaccaaa aattgatgtg tagtgttaat gtgcttacag ATGTTGATAC
    CACCTATCCA GATAAGAAGT CCATCTTAAT GTACATCACA
```

TABLE 6-continued

```
101 TCACTCTTCC AAGTTTTGCC TCAACAAGTG AGCATTGAAG CCATCCAGGA AGTGGAAATG
    TTGCCAAGGC CACCTAAAGT GACTAAAGAA GAACATTTTC

201 AGTTACATCA TCAAATGCAC TATTCTCAAC AGgtaaagtg tgtaaaggac agctactatt
    caagatgttt tctgttttat at Exon 9 (SEQ ID NO: 26)
  1 atggttttc cccctcctct ctatccactc ccccaaaccc ttctctgcag ATCACGGTCA
    GTCTAGCACA GGGATATGAG AGAACTTCTT CCCCTAAGCC 101 TCGATTCAAG AGCTATGCCT ACACACAGGC TGCTTATGTC ACCACCTCTG ACCCTACACG
    GAGCCCATTT CCTTCACAGg tctgtcaaca tttactctct 201 gttgtacaaa ccagagaact gcttccaag Exon 10 (SEQ ID NO: 27)
  1 aatctgcaaa gacattaatt gtgtaacacc caatttattt tattgtgcag CATTTGGAAG
    CTCCTGAAGA CAAGTCATTT GGCAGTTCAT TGATGGAGAG 101 TGAAGTAAAC CTGGACCGTT ATCAAACAGC TTTAGAAGAA GTATTATCGT GGCTTCTTTC
    TGCTGAGGAC ACATTGCAAG CACAAGGAGA GATTTCTAAT 201 GATGTGGAAG TGGTGAAAGA CCAGTTTCAT ACTCATGAGg taaactaaaa cgttaattta
    caaaacaaaa catatgactt gttataatg Exon 11 (SEQ ID NO: 28)
  1 ccgatttacc tagagttcta attacaattg ttaacttcct tctttgtcag GGGTACATGA
    TGGATTTGAC AGCCCATCAG GGCCGGGTTG GTAATATTCT 101 ACAATTGGGA GTAAGCTGA TTGGAACAGG AAAATTATCA GAAGATGAAG AAACTGAAGT
    ACAAGAGCAG ATGAATCTCC TAAATTCAAG ATGGGAATGC 201 CTCAGGGTAG CTAGCATGGA AAAACAAAGC AAgtaagtcc ttatttgttt ttaattaaga
    agactaacaa gttttggaag ct Exon 12 (SEQ ID NO: 29)
  1 taataagttg ctttcaaaga ggtcataata ggcttctttc aaattttcag TTTACATAGA
    GTTTTAATGG ATCTCCAGAA TCAGAAACTG AAAGAGTTGA 101 ATGACTGGCT AACAAAAACA GAAGAAAGAA CAAGGAAAAT GGAGGAAGAG CCTCTTGGAC
    CTGATCTTGA AGACCTAAAA CGCCAAGTAC AACAACATAA 201 Ggtaggtgta tcttatgttg cgtgctttct actagaaagc aaactctgtg t Exon 13 (SEQ ID NO: 30)
  1 cacatgtaag aatatcattt taatttcctt taaaacattt tatctttcag GTGCTTCAAG
    AAGATCTAGA ACAAGAACAA GTCAGGGTCA ATTCTCTCAC 101 TCACATGGTG GTGGTAGTTG ATGAATCTAG TGGAGATCAC GCAACTGCTG CTTTGGAAGA
    ACAACTTAAG gtcagattat tttgcttagt aaactaaata 201 tgtcctttaa aagaactata Exon 14 (SEQ ID NO: 31)
  1 cgtagttacc aattgtttgc tgatgctgtg cttgattgtc tcttctccag GTATTGGGAG
    ATCGATGGGC AAACATCTGT AGATGGACAG AAGACCGCTG 101 GGTTCTTTTA CAAGACATCC TTCTCAAATG GCAACGTCTT ACTGAAGAAC AGgtgtgtca
    tgtgtgagaa actagctgta aaagacacgg ggggatatta 201 Aa Exon 15 (SEQ ID NO: 32)
  1 agtaaagatt tatgtttatt tattccttgg aattcttttaa tgtcttgcag TGCCTTTTTA
    GTGCATGGCT TTCAGAAAAA GAAGATGCAG TGAACAAGAT 101 TCACACAACT GGCTTTAAAG ATCAAAATGA AATGTTATCA AGTCTTCAAA AACTGGCCgt
    atgtactttc tagctttcaa tggtcttata aaaacccagt 201 Actgtata Exon 16 (SEQ ID NO: 33)
  1 tgtatggaat gcaacccagg cttattctgt gatctttctt gttttaacag GTTTTAAAAG
    CGGATCTAGA AAAGAAAAAG CAATCCATGG GCAAACTGTA 101 TTCACTCAAA CAAGATCTTC TTTCAACACT GAAGAATAAG TCAGTGACCC AGAAGACGGA
    AGCATGGCTG GATAACTTTG CCCGGTGTTG GGATAATTTA
```

TABLE 6-continued

```
201 GTCCAAAAAC TTGAAAAGAG TACAGCACAG gttagtgata ccaattatca tgctacagac
    tatctcagag atttttttaaa Exon 17 (SEQ ID NO: 34)
  1 actgaagtct ttctagcaat gtctgacctc tgtttcaata cttctcacag ATTTCACAGG
    CTGTCACCAC CACTCAGCCA TCACTAACAC AGACAACTGT 101 AATGGAAACA GTAACTACGG TGACCACAAG GGAACAGATC CTGGTAAAGC ATGCTCAAGA
    GGAACTTCCA CCACCACCTC CCCAAAAGAA GAGGCAGATT 201 ACTGTGGATT CTGAAATTAG GAAAAGgtga gagcatctta agcttttatc tgcaaatgaa
    gtggagaaaa ctcatt Exon 18 (SEQ ID NO: 35)
  1 gaagaaagag ataatcaaga aataatgact tttatttttt gctgtcttag GTTGGATGTT
    GATATAACTG AACTTCACAG CTGGATTACT CGCTCAGAAG 101 CTGTGTTGCA GAGTCCTGAA TTTGCAATCT TTCGGAAGGA AGGCAACTTC TCAGACTTAA
    AAGAAAAAGT CAATgtaggt tatgcattaa ttttttatatc 201 tgtactcatt ttgtgctgct tgta Exon 19 (SEQ ID NO: 36)
  1 agattcacag tccttgtatt gaattactca tctttgctct catgctgcag GCCATAGAGC
    GAGAAAAAGC TGAGAAGTTC AGAAAACTGC AAGATGCCAG 101 CAGATCAGCT CAGGCCCTGG TGGAACAGAT GGTGAATGgt aattacacga gttgatttag
    ataatcttct tagggatttg ataaacac Exon 20 (SEQ ID NO: 37)
  1 tttcagtctg tgggttcagg ggatatattt aattattttt ttctttctag AGGGTGTTAA
    TGCAGATAGC ATCAAACAAG CCTCAGAACA ACTGAACAGC 101 CGGTGGATCG AATTCTGCCA GTTGCTAAGT GAGAGACTTA ACTGGCTGGA GTATCAGAAC
    AACATCATCG CTTTCTATAA TCAGCTACAA CAATTGGAGC 201 AGATGACAAC TACTGCTGAA AACTGGTTGA AAATCCAACC CACCACCCCA TCAGAGCCAA
    CAGCAATTAA AAGTCAGTTA AAAATTTGTA AGgtaagaat 301 ctcttctcct tccatttgga gcataatcaa taggtatttc tt Exon 21 (SEQ ID NO: 38)
  1 aatgtatgca aagtaaacgt gttacttact ttccatactc tatggcacag GATGAAGTCA
    ACCGGCTATC AGATCTTCAA CCTCAAATTG AACGATTAAA 101 AATTCAAAGC ATAGCCCTGA AAGAGAAAGG ACAAGGACCC ATGTTCCTGG ATGCAGACTT
    TGTGGCCTTT ACAAATCATT TTAAGCAAGT CTTTTCTGAT 201 GTGCAGGCCA GAGAGAAAGA GCTACAGACA Agtaagtaaa aagcctaaaa tggctaactt
    gacattttcc aaaatggtta t Exon 22 (SEQ ID NO: 39)
  1 aagtgtgaaa caattaagtg attctcattc ttttttccct tttgataaag TTTTTGACAC
    TTTGCCACCA ATGCGCTATC AGGAGACCAT GAGTGCCATC 101 AGGACATGGG TCCAGCAGTC AGAAACCAAA CTCTCCATAC CTCAACTTAG TGTCACCGAC
    TATGAAATCA TGGAGCAGAG ACTCGGGGAA TTGCAGgtct 201 gtgaatattt gaatgtcaaa acaataaagc acgcttatca agcatt Exon 23 (SEQ ID NO: 40)
  1 aattattatt catcaattag ggtaaatgta tttaaaaaat tgttttttag GCTTTACAAA
    GTTCTCTGCA AGAGCAACAA AGTGGCCTAT ACTATCTCAG 101 CACCACTGTG AAAGAGATGT CGAAGAAAGC GCCCTCTGAA ATTAGCCGGA AATATCAATC
    AGAATTTGAA GAAATTGAGG GACGCTGGAA GAAGCTCTCC 201 TCCCAGCTGG TTGAGCATTG TCAAAAGCTA GAGGAGCAAA TGAATAAACT CCGAAAAATT
    CAGgtaattc aagatttttac tttctaccct catttttatt 301 tacttgtttt ttc Exon 24 (SEQ ID NO: 41)
  1 ttaaaagtaa tcagcacacc agtaatgcct tataacgggt ctcgtttcag AATCACATAC
    AAACCCTGAA GAAATGGATG GCTGAAGTTG ATGTTTTTCT 101 GAAGGAGGAA TGGCCTGCCC TTGGGGATTC AGAAATTCTA AAAAAGCAGC TGAAACAGTG
    CAGAgtaaga ttttatatg atgcctttaa tatgaataat 201 tttgtatgaa tatt
```

TABLE 6-continued

Exon 25 (SEQ ID NO: 42)
```
  1 tatgtggcag taattttttt cagctggctt aaattgattt attttcttag CTTTTAGTCA
    GTGATATTCA GACAATTCAG CCCAGTCTAA ACAGTGTCAA 101 TGAAGGTGGG CAGAAGATAA AGAATGAAGC AGAGCCAGAG TTTGCTTCGA GACTTGAGAC
    AGAACTCAAA GAACTTAACA CTCAGTGGGA TCACATGTGC 201 CAACAGgtat agacaatctc tttcactgtg gcttgcctca acgtacttaa ctaaga
```

Exon 26 (SEQ ID NO: 43)
```
  1 atgtttcatc actgtcaata atcgtgtttt gtttgtttgt tttgtggaag GTCTATGCCA
    GAAAGGAGGC CTTGAAGGGA GGTTTGGAGA AAACTGTAAG 101 CCTCCAGAAA GATCTATCAG AGATGCACGA ATGGATGACA CAAGCTGAAG AAGAGTATCT
    TGAGAGAGAT TTTGAATATA AAACTCCAGA TGAATTACAG 201 AAAGCAGTTG AAGAGATGAA Ggtaaaaaaa aaaaaagaaa aactaagtaa aacaaaggaa
    ataaatggaa a
```

Exon 27 (SEQ ID NO: 44)
```
  1 ggatgtaaag ttattttcat gctattaaga gagcattctt tatttttcag AGAGCTAAAG
    AAGAGGCCCA ACAAAAAGAA GCGAAAGTGA AACTCCTTAC 101 TGAGTCTGTA AATAGTGTCA TAGCTCAAGC TCCACCTGTA GCACAAGAGG CCTTAAAAAA
    GGAACTTGAA ACTCTAACCA CCAACTACCA GTGGCTCTGC 201 ACTAGGCTGA ATGGGAAATG CAAGACTTTG GAAgtcagtt gcttttcttg gtctttgtca
    atgatatgtc aatacatggt cat
```

Exon 28 (SEQ ID NO: 45)
```
  1 tttactttc taccataata tttaatctgt gatatatatt tctttcttag GAAGTTTGGG
    CATGTTGGCA TGAGTTATTG TCATACTTGG AGAAAGCAAA 101 CAAGTGGCTA ATGAAGTAG AATTTAAACT TAAAACCACT GAAAACATTC CTGGCGGAGC
    TGAGGAAATC TCTGAGGTGC TAGATgtaag ttgtaaatta 201 agccaaatga tgataattta tatgcagtat taaaa
```

Exon 29 (SEQ ID NO: 46)
```
  1 tgtatttaga aaaaaaagga gaaatagtaa ttattgcaaa tgtgtttcag TCACTTGAAA
    ATTTGATGCG ACATTCAGAG GATAACCCAA ATCAGATTCG 101 CATATTGGCA CAGACCCTAA CAGATGGCGG AGTCATGGAT GAGCTAATCA ATGAGGAACT
    TGAGACATTT AATTCTCGTT GGAGGGAACT ACATGAAGAG 201 gtatgaagat aagtgaaaaa tctctttaat ctaatttgca ttaatgtata
```

Exon 30 (SEQ ID NO: 47)
```
  1 gctatcaaga gtaaacattt aactgataca ctcttattcc ttcttttag GCTGTAAGGA
    GGCAAAAGTT GCTTGAACAG AGCATCCAGT CTGCCCAGGA 101 GACTGAAAAA TCCTTACACT TAATCCAGGA GTCCCTCACA TTCATTGACA AGCAGTTGGC
    AGCTTATATT GCAGACAAGG TGGACGCAGC TCAAATGCCT 201 CAGGAAGCCC AGgcaagtac atctgggaat cagcttccat tcttttgttt ttattacttc
    aa
```

Exon 31 (SEQ ID NO: 48)
```
  1 tagttgttct ttgtagagca tgctgactaa taatgctatc ctcccaacag AAAATCCAAT
    CTGATTTGAC AAGTCATGAG ATCAGTTTAG AAGAAATGAA 101 GAAACATAAT CAGGGGAAGG AGGCTGCCCA AAGAGTCCTG TCTCAGATTG ATGTTGCACA
    Ggtatatgtt atttcagaaa ctaaggaacg tgttttcgtt 201 gggcattata c
```

Exon 32 (SEQ ID NO: 49)
```
  1 ttgtttgaaa ggcaaaatta aatcagtgcc ttttacact gtccttacag AAAAAATTAC
    AAGATGTCTC CATGAAGTTT CGATTATTCC AGAAACCAGC 101 CAATTTTGAG CAGCGTCTAC AAGAAAGTAA GATGATTTTA GATGAAGTGA AGATGCACTT
    GCCTGCATTG GAAACAAAGA GTGTGGAACA GGAAGTAGTA 201 CAGTCACAGC TAAATCATTG TGTGgtatgt atttctggtg gcaaatacgc aggtacccct
    tgactttcct catt
```

TABLE 6-continued

Exon 33 (SEQ ID NO: 50)
  1 Aataatttaa ctctactgat tatcatgttt tgttttatgt ttaaacttag AACTTGTATA
    AAAGTCTGAG TGAAGTGAAG TCTGAAGTGG AAATGGTGAT 101 AAAGACTGGA CGTCAGATTG TACAGAAAAA GCAGACGGAA AATCCCAAAG AACTTGATGA
    AAGAGTAACA GCTTTGAAAT TGCATTATAA TGAGCTGGGA 201 GCAAAGgtgt gtgcatgctg agaccacaaa cacttctttc cactttcctt ataaat Exon 34 (SEQ ID NO: 51)
  1 atttgaatta aagagtaaac taaattacat ttcattataa ttcttttcag GTAACAGAAA
    GAAAGCAACA GTTGGAGAAA TGCTTGAAAT TGTCCCGTAA 101 GATGCGAAAG GAAATGAATG TCTTGACAGA ATGGCTGGCA GCTACAGATA TGGAATTGAC
    AAAGAGATCA GCAGTTGAAG GAATGCCTAG TAATTTGGAT 201 TCTGAAGTTG CCTGGGGAAA Ggtaaaacct atatcactga aggttatttt gaacatacgt
    gaaaacacat a Exon 35 (SEQ ID NO: 52)
  1 tcttaagact acaagacatt acttgaaggt caatgctctc cttttcacag GCTACTCAAA
    AAGAGATTGA GAAACAGAAG GTGCACCTGA AGAGTATCAC 101 AGAGGTAGGA GAGGCCTTGA AAACAGTTTT GGGCAAGAAG GAGACGTTGG TGGAAGATAA
    ACTCAGTCTT CTGAATAGTA ACTGGATAGC TGTCACCTCC 201 CGAGCAGAAG AGTGGTTAAA TCTTTTGTTG gtaagagaaa aggctagaag cttttacacc
    cttctctgtc acgagaaaaa Exon 36 (SEQ ID NO: 53)
  1 aagaatattg tctaaccaat aatgccatgg tatgtctctg tacaattaag GAATACCAGA
    AACACATGGA AACTTTTGAC CAGAATGTGG ACCACATCAC 101 AAAGTGGATC ATTCAGGCTG ACACACTTTT GGATGAATCA GAGAAAAAGA AACCCCAGCA
    AAAAGAAGAC GTGCTTAAGg tagcaaataa aatatgaaaa 201 gtaatgtcca aattgtacac cagttactt Exon 37 (SEQ ID NO: 54)
  1 ccttcattaa ttactaactt caagtcctat ctcttgctca tggaatatag CGTTTAAAGG
    CAGAACTGAA TGACATACGC CCAAAGGTGG ACTCTACACG 101 TGACCAAGCA GCAAACTTGA TGGCAAACCG CGGTGACCAC TGCAGGAAAT TAGTAGAGCC
    CCAAATCTCA GAGCTCAACC ATCGATTTGC AGCCATTTCA 201 CACAGAATTA AGACTGGAAA Ggtaggaaga tctactccaa ggtggaaact tgtgctaaat
    ggtctcttgc g Exon 38 (SEQ ID NO: 55)
  1 ttctaataaa aagtaatttt gatttaaagt agcactatct ttttttttag GCCTCCATTC
    CTTTGAAGGA ATTGGAGCAG TTTAACTCAG ATATACAAAA 101 ATTGCTTGAA CCACTGGAGG CTGAAATTCA GCAGGGGGTG AATCTGAAAG AGGAAGACTT
    CAATAAAGAT ATGgtaaatt ggttgtgata aaagtgtgaa 201 tgaactagga gtggaaataa ata Exon 39 (SEQ ID NO: 56)
  1 acagctttt aaaaaccaaa atgaagactg tacttgttgt ttttgatcag AATGAAGACA
    ATGAGGGTAC TGTAAAAGAA TTGTTGCAAA GAGGAGACAA 101 CTTACAACAA AGAATCACAG ATGAGAGAAA GCGAGAGGAA ATAAAGATAA AACAGCAGCT
    GTTACAGACA AAACATAATG CTCTCAAGgt attagagcta 201 aaattataat ataccttgcc tgtggttttt ttttaata Exon 40 (SEQ ID NO: 57)
  1 tgcactatac atatatattg atattttaat aatgtctgca ccatgaacag GATTTGAGGT
    CTCAAAGAAG AAAAAAGGCT CTAGAAATTT CTCATCAGTG 101 GTATCAGTAC AAGAGGCAGG CTGATGATCT CCTGAAATGC TTGGATGACA TTGAAAAAAA
    ATTAGCCAGC CTACCTGAGC CCAGAGATGA AAGGAAAATA 201 AAGgtaatgt tgttttagaa tgtcaatacc agattttatt atacagttta att Exon 41 (SEQ ID NO: 58)
  1 tgatgtggtt agctaactgc cctgggccct gtattggttt tgctcaatag GAAATTGATC
    GGGAATTGCA GAAGAAGAAA GAGGAGCTGA ATGCAGTGCG TABLE 6-continued 101 TAGGCAAGCT GAGGGCTTGT CTGAGGATGG GGCCGCAATG GCAGTGGAGC CAACTCAGAT
    CCAGCTCAGC AAGCGCTGGC GGGAAATTGA GAGCAAATTT 201 GCTCAGTTTC GAAGACTCAA CTTTGCACAA ATTgtgagtt gttactggca aacccacgta
    tgtgtttgca actactactc tat Exon 42 (SEQ ID NO: 59)
  1 ttcactgtta ggaagctaaa aaaaattgtt cttttgtata tctataccag CACACTGTCC
    GTGAAGAAAC GATGATGGTG ATGACTGAAG ACATGCCTTT 101 GGAAATTTCT TATGTGCCTT CTACTTATTT GACTGAAATC ACTCATGTCT CACAAGCCCT
    ATTAGAAGTG GAACAACTTC TCAATGCTCC TGACCTCTGT 201 GCTAAGGACT TTGAAGATCT CTTTAAGCAA GAGGAGTCTC TGAAGgtaaa accaaagcac
    tttcattcgt attttacaag gtgatcatac tgatc Exon 43 (SEQ ID NO: 60)
  1 tatagacagc taattcattt ttttactgtt ttaaaattt tatattacag AATATAAAAG
    ATAGTCTACA ACAAAGCTCA GGTCGGATTG ACATTATTCA 101 TAGCAAGAAG ACAGCAGCAT TGCAAAGTGC AACGCCTGTG GAAAGGGTGA AGCTACAGGA
    AGCTCTCTCC CAGCTTGATT TCCAATGGGA AAAAGTTAAC 201 AAAATGTACA AGGACCGACA AGGgtaggta acacatatat ttttcttgat acttgcagaa
    atgatttgtt ttc Exon 44 (SEQ ID NO: 61)
  1 gttttacata atccatctat ttttcttgat ccatatgctt ttacctgcag GCGATTTGAC
    AGATCTGTTG AGAAATGGCG GCGTTTTCAT TATGATATAA 101 AGATATTTAA TCAGTGGCTA ACAGAAGCTG AACAGTTTCT CAGAAAGACA CAAATTCCTG
    AGAATTGGGA ACATGCTAAA TACAAATGGT ATCTTAAGgt 201 aagtctttga tttgtttttt cgaaattgta tttatcttca gcacatct Exon 45 (SEQ ID NO: 62)
  1 taaaaagaca tggggcttca ttttgttttt gccttttgg tatcttacag GAACTCCAGG
    ATGGCATTGG GCAGCGGCAA ACTGTTGTCA GAACATTGAA 101 TGCAACTGGG AAGAAATAA TTCAGCAATC CTCAAAAACA GATGCCAGTA TTCTACAGGA
    AAAATTGGGA AGCCTGAATC TGCGGTGGCA GGAGGTCTGC 201 AAACAGCTGT CAGACAGAAA AAAGAGgtag ggcgacagat ctaataggaa tgaaaacatt
    ttagcagact ttttaa Exon 46 (SEQ ID NO: 63)
  1 tgagaactat gttggaaaaa aaaataacaa ttttattctt cttctccag GCTAGAAGAA
    CAAAAGAATA TCTTGTCAGA ATTTCAAAGA GATTTAAATG 101 AATTTGTTTT ATGGTTGGAG GAAGCAGATA ACATTGCTAG TATCCCACTT GAACCTGGAA
    AAGAGCAGCA ACTAAAAGAA AAGCTTGAGC AAGTCAAGgt 201 aattttattt tctcaaatcc cccagggcct gcttgcataa agaagtat Exon 47 (SEQ ID NO: 64)
  1 ggaattgtgc tgtaattcat tttaaacgtt gttgcatttg tctgtttcag TTACTGGTGG
    AAGAGTTGCC CCTGCGCCAG GAATTCTCA AACAATTAAA 101 TGAAACTGGA GGACCCGTGC TTGTAAGTGC TCCCATAAGC CCAGAAGAGC AAGATAAACT
    TGAAAATAAG CTCAAGCAGA CAAATCTCCA GTGGATAAAG 201 gttagacatt aaccatctct tccgtcacat gtgttaaatg ttgcaagtat Exon 48 (SEQ ID NO: 65)
  1 gcttatgcct tgagaattat ttaccttttt aaaatgtatt tcctttcag GTTTCCAGAG
    CTTTACCTGA GAACAAGGA GAAATTGAAG CTCAAATAAA 101 AGACCTTGGG CAGCTTGAAA AAAAGCTTGA AGACCTTGAA GAGCAGTTAA ATCATCTGCT
    GCTGTGGTTA TCTCCTATTA GGAATCAGTT GGAAATTTAT 201 AACCAACCAA ACCAAGAAGG ACCATTTGAC GTTAAGgtag ggaactttt gctttaaata
    tttttgtctt ttttaagaaa aatggc Exon 49 (SEQ ID NO: 66)
  1 ttattgctaa ctgtgaagtt aatctgcact atatgggttc ttttcccag GAAACTGAAA
    TAGCAGTTCA AGCTAAACAA CCGGATGTGG AAGAGATTTT 101 GTCTAAAGGG CAGCATTTGT ACAAGGAAAA ACCAGCCACT CAGCCAGTGA AGgtaatgaa
    gcaacctcta gcaatatcca ttacctcata atgggttatg TABLE 6-continued 201 Ct Exon 50 (SEQ ID NO: 67)
  1 atcttcaaag tgttaatcga ataagtaatg tgtatgcttt tctgttaaag AGGAAGTTAG
    AAGATCTGAG CTCTGAGTGG AAGGCGGTAA ACCGTTTACT 101 TCAAGAGCTG AGGGCAAAGC AGCCTGACCT AGCTCCTGGA CTGACCACTA TTGGAGCCTg
    taagtatact ggatcccatt ctctttggct ctagctattt 201 Gttcaaaag Exon 51 (SEQ ID NO: 68)
  1 tttttctttt tcttcttttt tccttttgc aaaaacccaa aatatttag CTCCTACTCA
    GACTGTTACT CTGGTGACAC AACCTGTGGT TACTAAGGAA 101 ACTGCCATCT CCAAACTAGA AATGCCATCT TCCTTGATGT TGGAGGTACC TGCTCTGGCA
    GATTTCAACC GGGCTTGGAC AGAACTTACC GACTGGCTTT 201 CTCTGCTTGA TCAAGTTATA AAATCACAGA GGGTGATGGT GGGTGACCTT GAGGATATCA
    ACGAGATGAT CATCAAGCAG AAGgtatgag aaaaaatgat 301 aaaagttggc agaagttttt ctttaaaatg aag Exon 52 (SEQ ID NO: 69)
  1 aatacacaac gctgaagaac cctgatacta agggatattt gttcttacag GCAACAATGC
    AGGATTTGGA ACAGAGGCGT CCCCAGTTGG AAGAACTCAT 101 TACCGCTGCC CAAAATTTGA AAAACAAGAC CAGCAATCAA GAGGCTAGAA CAATCATTAC
    GGATCGAAgt aagttttta acaagcatgg gacacacaaa 201 gcaagatgca tgacaagt Exon 53 (SEQ ID NO: 70)
  1 cctccagact agcatttact actatatatt tattttcct tttattctag TTGAAAGAAT
    TCAGAATCAG TGGGATGAAG TACAAGAACA CCTTCAGAAC 101 CGGAGGCAAC AGTTGAATGA AATGTTAAAG GATTCAACAC AATGGCTGGA AGCTAAGGAA
    GAAGCTGAGC AGGTCTTAGG ACAGGCCAGA GCCAAGCTTG 201 AGTCATGGAA GGAGGGTCCC TATACAGTAG ATGCAATCCA AAAGAAAATC ACAGAAACCA
    AGgttagtat caaagatacc tttttaaaat aaaatactgg 301 ttacatttga ta Exon 54 (SEQ ID NO: 71)
  1 atttcataaa aaaaactgac attcattctc tttctcataa aaatctatag CAGTTGGCCA
    AAGACCTCCG CCAGTGGCAG ACAAATGTAG ATGTGGCAAA 101 TGACTTGGCC CTGAAACTTC TCCGGGATTA TTCTGCAGAT GATACCAGAA AAGTCCACAT
    GATAACAGAG AATATCAATG CCTCTTGGAG AAGCATTCAT 201 AAAAGgtatg aattacatta tttctaaaac tactgttggc tgtaataatg gggtg Exon 55 (SEQ ID NO: 72)
  1 gcaccattct gatatttaat aattgcatct gaacatttgg tcctttgcag GGTGAGTGAG
    CGAGAGGCTG CTTTGGAAGA AACTCATAGA TTACTGCAAC 101 AGTTCCCCCT GGACCTGGAA AAGTTTCTTG CCTGGCTTAC AGAAGCTGAA ACAACTGCCA
    ATGTCCTACA GGATGCTACC CGTAAGGAAA GGCTCCTAGA 201 AGACTCCAAG GGAGTAAAAG AGCTGATGAA ACAATGGCAA gtaagtcagg catttccgct
    ttagcactct tgtggatcca attgaacaat Exon 56 (SEQ ID NO: 73)
  1 ttcttttgtt tggtaattct gcacatattc ttcttcctgc tgtcctgtag GACCTCCAAG
    GTGAAATTGA AGCTCACACA GATGTTTATC ACAACCTGGA 101 TGAAAACAGC CAAAAAATCC TGAGATCCCT GGAAGGTTCC GATGATGCAG TCCTGTTACA
    AAGACGTTTG GATAACATGA ACTTCAAGTG GAGTGAACTT 201 CGGAAAAAGT CTCTCAACAT TAGgtaggaa aagatgtgga gcaaaaaggc cacaaatgaa
    ttaaaatggc caa Exon 57 (SEQ ID NO: 74)
  1 caattacact tctagatatt ctgacatggt acgctgctgt tctttttcag GTCCCATTTG
    GAAGCCAGTT CTGACCAGTG GAAGCGTCTG CACCTTTCTC 101 TGCAGGAACT TCTGGTGTGG CTACAGCTGA AGATGATGA ATTAAGCCGG CAGGCACCTA
    TTGGAGGCGA CTTTCCAGCA GTTCAGAAGC AGAACGATGT TABLE 6-continued

```
201 ACATAGGgta ggacattttt aagcctcgtg ccttgcacat gttaagcaca tagtaat

Exon 58 (SEQ ID NO: 75)
  1 agaagaatgc cacaagccaa ataagcactt cttttcatct catttcacag GCCTTCAAGA
    GGGAATTGAA AACTAAAGAA CCTGTAATCA TGAGTACTCT 101 TGAGACTGTA CGAATATTTC TGACAGAGCA GCCTTTGGAA GGACTAGAGA AACTCTACCA
    GGAGCCCAGA Ggtaattgaa tgtggaacta taataacata 201 ttgatagaag gatcagtggt g Exon 59 (SEQ ID NO: 76)
  1 gtttaaaaaa aaagaatgtg gcctaaaacc ttgtcatatt gccaatttag AGCTGCCTCC
    TGAGGAGAGA GCCCAGAATG TCACTCGGCT TCTACGAAAG 101 CAGGCTGAGG AGGTCAATAC TGAGTGGGAA AAATTGAACC TGCACTCCGC TGACTGGCAG
    AGAAAAATAG ATGAGACCCT TGAAAGACTC CGGGAACTTC 201 AAGAGGCCAC GGATGAGCTG GACCTCAAGC TGCGCCAAGC TGAGGTGATC AAGGGATCCT
    GGCAGCCCGT GGGCGATCTC CTCATTGACT CTCTCCAAGA 301 TCACCTCGAG AAAGTCAAGg taccgtctac ttctttgctt cagggccctt tgagagactc
    aaaagagct Exon 60 (SEQ ID NO: 77)
  1 ttgttttaaa tattctcatc ttccaatttg cttttgacta ttgcacacag GCACTTCGAG
    GAGAAATTGC GCCTCTGAAA GAGAACGTGA GCCACGTCAA 101 TGACCTTGCT CGCCAGCTTA CCACTTTGGG CATTCAGCTC TCACCGTATA ACCTCAGCAC
    TCTGGAAGAC CTGAACACCA GATGGAAGCT TCTGCAGgta 201 agcacattgt aaacattgtt gtcctttgtt acagtaaaat aatatac Exon 61 (SEQ ID NO: 78)
  1 tcctcattat atagaatgag agaacatcat ttctctcctt ttcctcccag GTGGCCGTCG
    AGGACCGAGT CAGGCAGCTG CATGAAGCCC ACAGGGACTT 101 TGGTCCAGCA TCTCAGCACT TTCTTTCCAg taagtcattt tcagctttta tcacttaact
    ttattgcatc ttgattaat Exon 62 (SEQ ID NO: 79)
  1 gcgatgaatt tgacctcctt gcctttcttt ttttcctccc ttcttttcag CGTCTGTCCA
    GGGTCCCTGG GAGAGAGCCA TCTCGCCAAA CAAAGTGCCC 101 TACTATATCA Agtaagttgg aagtatcaca ttttttaaaag agcatttatt gtgactaacc
    t Exon 63 (SEQ ID NO: 80)
  1 tgactactca ttgtaaatgc taaagtctttt ctttatgttt tgtgttttag CCACGAGACT
    CAAACAACTT GCTGGGACCA TCCCAAAATG ACAGAGCTCT 101 ACCAGTCTTT AGgtaaggac atggccatgt ttcctccaag ttaaatgaca ggtgacctttt
    ag Exon 64 (SEQ ID NO: 81)
  1 ctgttatttc tgatggaata acaaatgctc tttgttttcc ctcttttcag CTGACCTGAA
    TAATGTCAGA TTCTCAGCTT ATAGGACTGC CATGAAACTC 101 CGAAGACTGC AGAAGGCCCT TTGCTgtaag tattggccag tatttgaaga tcttgatact
    atgtctttgc ttaga Exon 65 (SEQ ID NO: 82)
  1 aggaaggttt tactctttga gtcatttgtg attttatttg ttttttgcag TGGATCTCTT
    GAGCCTGTCA GCTGCATGTG ATGCCTTGGA CCAGCACAAC 101 CTCAAGCAAA ATGACCAGCC CATGGATATC CTGCAGATTA TTAATTGTTT GACCACTATT
    TATGACCGCC TGGAGCAAGA GCACAACAAT TTGGTCAACG 201 TCCCTCTCTG CGTGGATATG TGTCTGAACT GGCTGCTGAA TGTTTATGAT ACgtacgtat
    ggcatgtttt tatttcccgg gctctgtcac aggaggctta 301 Gc Exon 66 (SEQ ID NO: 83)
  1 cctctaggaa agggtcagta attgtttttct gctttgattc ttcataatag GGGACGAACA
    GGGAGGATCC GTGTCCTGTC TTTTAAAACT GGCATCATTT 101 CCCTGTGTAA AGCACATTTG GAAGACAAGT ACAGATgtaa gtcgtgtata ttaatgctgt
    attctttat taatgttggc taatta
```

TABLE 6-continued

Exon 67 (SEQ ID NO: 84)
  1 atccatgggt gctgtgtttt gactgttgca attttcttct tcctttgtag ACCTTTTCAA
    GCAAGTGGCA AGTTCAACAG GATTTTGTGA CCAGCGCAGG 101 CTGGGCCTCC TTCTGCATGA TTCTATCCAA ATTCCAAGAC AGTTGGGTGA AGTTGCATCC
    TTTGGGGGCA GTAACATTGA GCCAAGTGTC CGGAGCTGCT 201 TCCAATTTGt aagttattca ccttctaggt aacatattta ttctttcata ttttagaa Exon 68 (SEQ ID NO: 85)
  1 ctttcctttc atccttttgc cctccttctc tctccctcct gtctttgcag GCTAATAATA
    AGCCAGAGAT CGAAGCGGCC CTCTTCCTAG ACTGGATGAG 101 ACTGGAACCC CAGTCCATGG TGTGGCTGCC CGTCCTGCAC AGAGTGGCTG CTGCAGAAAC
    TGCCAAGCAT CAGGCCAAAT GTAACATCTG CAAAGAGTGT 201 CCAATCATTG GATTCAGgta ttaggaacca aaaaaaaaat gtcattttt tctcatcatt
    tttcacc Exon 69 (SEQ ID NO: 86)
  1 ggaatttgat tcgaagaaat acatacgtgt ttgttttttgc tctttatcag GTACAGGAGT
    CTAAAGCACT TTAATTATGA CATCTGCCAA AGCTGCTTTT 101 TTTCTGGTCG AGTTGCAAAA GGCCATAAAA TGCACTATCC CATGGTGGAA TATTGCACTC
    CGgtaagttt gacgccagcc tgacgtgaga gttagttcac 201 ctgggataaa tt Exon 70 (SEQ ID NO: 87)
  1 tttgaaatca tcctgtccta aatctgatct caccatgatc tcccttttag ACTACATCAG
    GAGAAGATGT TCGAGACTTT GCCAAGGTAC TAAAAAACAA 101 ATTTCGAACC AAAAGGTATT TTGCGAAGCA TCCCCGAATG GGCTACCTGC CAGTGCAGAC
    TGTCTTAGAG GGGGACAACA TGGAAACgtg agtagtagca 201 aaagcagaac acactcttgt ttgatgtata tttgaac Exon 71 (SEQ ID NO: 88)
  1 cggctgagtt tgcgtgtgtc tccttcacca cctcattttt tgttttgcag TCCCGTTACT
    CTGATCAACT TCTGGCCAGT AGATTCTGCg tgagtacttt 101 ttttgctgaa gggtgctgct accaccaaca cattcgctc Exon 72 (SEQ ID NO: 89)
  1 tctccattaa tggatggtat ctgtgactaa tcacattttc tgccttatag GCCTGCCTCG
    TCCCCTCAGC TTTCACACGA TGATACTCAT TCACGCATTG 101 AACATTATGC TAGCAGgtat gagactagtt gtatgccagg caaatattga ttgaaataac
    taacca Exon 73 (SEQ ID NO: 90)
  1 gattctaaga cgtcacataa gttttaatga gcttttacgt ttttatcag GCTAGCAGAA
    ATGGAAAACA GCAATGGATC TTATCTAAAT GATAGCATCT 101 CTCCTAATGA GAGCATgtaa gtatcccatc tctttttaca aatgttcct gacaatgaaa
    ttgctt Exon 74 (SEQ ID NO: 91)
  1 aagcaaaata aggggggggaa aaaccaaaaa cctttgattt tattttccag AGATGATGAA
    CATTTGTTAA TCCAGCATTA CTGCCAAAGT TTGAACCAGG 101 ACTCCCCCCT GAGCCAGCCT CGTAGTCCTG CCCAGATCTT GATTTCCTTA GAGAGTGAGG
    AAAGAGGGGA GCTAGAGAGA ATCCTAGCAG ATCTTGAGGA 201 AGAAACAGg tgagttttct ttctagcttt gtcattggta tgcagagtgc atacacttg Exon 75 (SEQ ID NO: 92)
  1 ttttcttttt cttctttttt ttttcttttt tactttttg atgccaatag GAATCTGCAA
    GCAGAATATG ACCGTCTAAA GCAGCAGCAC GAACATAAAG 101 GCCTGTCCCC ACTGCCGTCC CCTCCTGAAA TGATGCCCAC CTCTCCCCAG AGTCCCCGGG
    ATGCTGAGCT CATTGCTGAG GCCAAGCTAC TGCGTCAACA 201 CAAAGGCCGC CTGGAAGCCA GGATGCAAAT CCTGGAAGAC CACAATAAAC AGCTGGAGTC
    ACAGTTACAC AGGCTAAGGC AGCTGCTGGA GCAAgtgagg 301 agagagatgg gattttaca aacattcatt tttccctctt aaac TABLE 6-continued

```
Exon 76 (SEQ ID NO: 93)
  1 tttgtatgtt tattatgaaa agtaattctgttttcttttg gatgacttag CCCCAGGCAG
    AGGCCAAAGT GAATGGCACA ACGGTGTCCT CTCCTTCTAC 101 CTCTCTACAG AGGTCCGACA GCAGTCAGCCTATGCTGCTC CGAGTGGTTG GCAGTCAAAC
    TTCGGACTCC ATGGgtaagt gtcctagcta ctctcagatt 201 ttgttgtctg aagaaaggta gagt Exon 77 (SEQ ID NO: 94)
  1 ctgttttcta taaatgtaat tttccattatttgtttttgc ttttattaag GTGAGGAAGA
    TCTTCTCAGT CCTCCCCAGG ACACAAGCAC AGGGTTAGAG 101 GAGGTGATGG AGCAACTCAA CAACTCCTTCCCTAGTTCAA GAGgtaagct ccaataccta
    gaagggactc agatttgctg ggatcaggcc act Exon 78 (SEQ ID NO: 95)
  1 ttttttttccc tttctgatat ctctgcctcttcctctctct attattaaag GAAGAAATAC
    CCCTGGAAAG CCAATGAGAG AGgttagtga gattcaggct 101 cacggccatg gcttctgtct gtctcatcctgc Exon 79 (SEQ ID NO: 96)
  1 tctatctgca cctttgtaa agtctgtctt tctttctctt tgttttccag GACACAATGT
    AG
```

Exons for which exon skipping can be therapeutic, for the treatment of muscular dystrophy and other conditions, will be evident to a skilled worker. There is a substantial literature on the design of specific exons in DMD and many thousands of other exons in the human genome potentially amenable to exon skipping. For instance, a nonsense mutation within an exon which if deleted would not alter the reading frame, may be able to be removed from the mature RNA by targeted removal by exon skipping. The possible exons in the human genome are too numerous to list. In the DMD gene alone, there are 79 exons and many sequences that can be used to partially block inclusion of a given exon (from exon 2-exon 78) that are therapeutically relevant. For example, in 2007, Wilton et at described a series of oligos that can skip single exons across the DMD gene. (Wilton et at (2007) Mol Ther. 15, 1288-1296). Other work by Pramono et at demonstrates oligo design principles (Pramono et al. (2012) Hum Gene Ther 23(7), 781-90). Malueka et at describe a decision metric for oligo targeting in DMD (Malueka et at (2012) BMC Genet. 13, 23). Popplewell, et at also describe design principles for the oligo component of the combined therapeutic described in the present invention (Popplewell, et at (2012) Methods Mol Biol. 867, 143-67). Further, recently published work by Aoki, et at describe the skipping of multiple exons from exon 45-55 in mouse (Aoki, et at (2012) Proc Natl Acad Sci USA. 109 (34), 13763-8). This is therapeutically relevant for human Duchenne therapy as well as up to 65% of all DMD affected individuals could be treated by this cocktail. Since the described invention works on multiple independent exons, it is expected that the chemical entities described herein will improve the removal of specific individual and sets of exons from the mature transcript in vivo and in vitro. The general field of AO design for DMD is described in Aarstma-Rus, 2012 and Lu, 2011. Further, the removal of exonic duplications (see Aartsma-Rus (2007), BMC Med Genet. 5, 8:43) commonly observed in DMD may also be improved by combination use with the compounds described herein.

For reviews of conditions or diseases that can be treated by a method of the invention, see, e.g., Bauman et al. (2011) Bioeng. Bugs. 2, 125-8, Hammond et al. (2011) Trends Genet. 27, 196-205, Wood et al. (2010) Brain 133, 957-72 or Sazani et al., "Splice-switching oligonucleotides as potential therapeutics" (2007) in Antisense Drug Technology: Principles, Strategies, and Applications, Second Edition (Ed. S. T. Crooke) 89-114 (CRC Press, Boca Raton). Among the diseases treatable by modulation of exon skipping are, e.g., spinal muscle atrophy (SMA), Hutchinson-Gilford progeria syndrome (HGPS), beta-thalassemia, Ataxia telangiectasia (ATM), dysferlinopathies, frontotemporal dementia and cystic fibrosis.

In embodiments of the invention, a compound of the invention is administered to a subject, e.g. as part of an adjuvant treatment, or is contacted (e.g., in vitro) with a pre-mRNA target of interest, in conjunction with a suitable AO that is designed to specifically block a splicing event of interest. "In conjunction with" means that the AO can be administered before, or at the same time as, or after, the compound, and that the two components can be administered in separate delivery vehicles or in the same delivery vehicle. The two agents can be administered with the same, or different, dosage regimens. As used herein, the singular forms "a," "an," and "the" include plural referents unless the context clearly dictates otherwise. For example, "an" AO, as used above, means one or more AO molecules, which can be the same or different.

A number of considerations are generally taken into account in designing delivery systems, routes of administration, and formulations for compounds or combinations of compounds and an AO of the invention. The appropriate delivery system for an agent of the invention will depend upon its particular nature, the particular clinical application, and the site of drug action. One skilled in the art can easily determine the appropriate dose, schedule, and method of administration for the exact formulation of the composition being used, in order to achieve the desired response in the individual patient.

Any of a variety of conventional methods can be used to introduce AOs and/or small molecules of the invention into cells, in vitro or in vivo. These methods include, for example, transfection, electroporation, hydrodynamic "high pressure" delivery, nanoparticle delivery, liposomes, colloidal dispersal systems, or other methods known in the art.

Intracellular AO delivery can be enhanced by conjugating cell penetrating peptides to the AO using methods and compounds known in the art. See, e.g., U.S. Pat. No. 7,468,418 and PCT publications WO2009/005793 and WO2009/147368.

Compounds and AO's can be administered (delivered) to a subject by the same or by different modes of administration. Suitable modes of administration include, e.g., subcutaneous, intramuscular, intravenous, oral, intranasal, cutaneous, or suppository routes, depending on the formulation, the compound, and the condition to be treated. Compounds and AO's of the invention may be delivered via a variety of routes including all of the above routes, in dosing patterns that can be optimized with routine, conventional methods. In one embodiment, the compounds are administered chronically to subjects (patients) in conjunction with therapeutic antisense oligonucleodies. In some embodiments, a compound of the invention is administered frequently (e.g., daily or more frequently) to augment less frequent (e.g., monthly or weekly) administration, such as by intravenous or subcutaneous injection, of AO.

Formulations for delivery by a particular method (e.g., solutions, buffers, and preservatives) can be optimized by routine, conventional methods that are well-known in the art. See, e.g., Remington's Pharmaceutical Sciences, 18$^{th}$ edition (1990, Mack Publishing Co., Easton, Pa.). for guidance in suitable formulations.

An "effective" dose of an agent of the invention (either a compound, or a compound in conjunction with an AO, or the AO), or composition thereof, is a dose that, when administered to an animal, particularly a human, in the context of the present invention, is sufficient to effect at least a detectable amount of a therapeutic response in the individual over a reasonable time frame.

The exact amount of the dose (of a small molecule of the invention, used alone or in conjunction with an AO, or of the AO), will vary from subject to subject, depending on the species, age, weight and general condition of the subject, the severity or mechanism of any disorder being treated, the particular agent or vehicle used, its mode of administration and the like. The dose will also be a function of the exon that is being skipped/removed from the mature RNA and the sequence of the AO. The dose used to achieve a desired effect in vivo will be determined by the potency of the particular agent employed, the pharmacodynamics associated with the agent in the host, the severity of the disease state of infected individuals, as well as, in the case of systemic administration, the body weight and age of the individual. The size of the dose also will be determined by the existence of any adverse side effects that may accompany the particular inhibitory agent, or composition thereof, employed. It is generally desirable, whenever possible, to keep adverse side effects to a minimum.

For example, a dose of a small molecule of the invention can range from about 4-10 mg/kg/day, or can be higher or lower. In general, the dose of a small molecule of the invention is one, or close to one, which has been shown to be safe for subjects, such as human patients. Dantrolene, for example, has been shown to be safe when administered to humans up to 8 mg/kg/day during long term administration. Suitable oral doses of Dantrolene include doses of about 4-10, e.g. about 6-8, mg/kg/day. An example herein shows a functional benefit (wire hang test in mdx mice) using 10 mg/kg/week of the oligo AON23 and dantrolene at 10 mg/kg/day compared to 10 mg/kg/week of the AON23 alone (p=0.022).

Dosages for administration of a therapeutic agent of the invention can be in unit dosage form, such as a tablet or capsule. The term "unit dosage form" as used herein refers to physically discrete units suitable as unitary dosages for human and animal subjects, each unit containing a predetermined quantity of an inhibitor of the invention, alone or in combination with other therapeutic agents, calculated in an amount sufficient to produce the desired effect in association with a pharmaceutically acceptable diluent, carrier, or vehicle.

One embodiment of the invention is a method for identifying a small molecule compound that enhances exon skipping in an mRNA of interest, comprising testing candidate small molecules, such as variants of a compound in Table 1, for their ability to enhance exon skipping in the mRNA, and selecting compounds which exhibit greater enhancement activity than the compound from Table 1. The screening method can be carried out in the absence of, or in conjunction with, an AO specific for a splicing sequence of the exon that is to be skipped.

In one embodiment, the method comprises contacting a suitable cell (in vitro or in vivo) with a putative small molecule compound, such as a variant of one of the compounds of Table 1, and measuring the amount of splicing or, in one embodiment, of exon skipping, of interest. Any of the assays discussed herein can be adapted to such a screen. The amount of splicing or exon skipping can be compared to a control value. For example, for an assay which is conducted in the absence of an AO, the control can be a cell that has not been contacted with the compound. For an assay which is conducted in the presence of a suitable AO, the control can be a cell that is contacted with the AO but not the putative compound. A statistically significant decrease in the amount of splicing or increase in the amount of exon skipping in the test cells compared to the control is indicative that the putative compound is superior to the compound from which it has been derived, or to a suitable arbitrarily selected control compound.

As Dantrolene has a known molecular target, the ryanodine receptor which it binds directly, other agents that modify the activity of the ryanodine receptor are likely to have the same effect. For instance, a class of agents called 'RyCals' or 'calcium channel stabilizers' which stabilize the interaction of calstabin with ryanodine receptor and effectively block ryanodine receptor calcium leak are expected to have a similar effect as Dantrolene. See, e.g., Andersson et al. (2010) *Drug Discov Today Dis Mech* 7, 3151-e157 or Wehrens et al. (20050 *Proc Natl Acad Sci USA* 102, 9607-12.

Suitable variant compounds that can be tested will be evident to a skilled worker. For example, a substituent on, e.g., an aromatic or non-aromatic carbon can be substituted with H, alkyl, alkoxy, hydroxyalkyl, thioalkyl, haloalkyl, aminoalkyl, alkoxyalkyl, alkylaminoalkyl, etc. Some suitable variants are discussed below. Others will be evident to a skilled worker. Suitable (e.g., improved) variant compounds that are identified by such a screen are also included in the invention, and are sometimes referred to herein as "active variants" of the compounds. An "active variant," as used herein, refers to a compound which retains at least one activity of the compound of which it is a variant, e.g. the ability to block splicing of an exon of interest.

The terms "alkyl" used alone or as part of a larger moiety (i.e. "alkoxy," "hydroxyalkyl," "alkoxyalkyl," and "alkoxycarbonyl") include both straight and branched chains containing one to ten carbon atoms (i.e. 1, 2, 3, 4, 5, 6, 7, 8, 9, or 10 carbon atoms), as well as cyclic structures such as cyclopropyl and cyclobutyl. Examples of alkyl groups include methyl (Me), ethyl (Et), propyl (Pr) (including n-propyl ($^n$Pr or n-Pr), isopropyl ($^i$Pr or i-Pr) and cyclopropyl ($^c$Pr or c-Pr)), butyl (Bu) (including n-butyl ($^n$Bu or n-Bu), isobutyl ($^i$Bu or i-Bu), tert-butyl ($^t$Bu or t-Bu) and cyclobutyl ($^c$Bu or c-Bu)), pentyl (Pe) (including n-pentyl) and so forth. Alkyl groups also include mixed cyclic and linear alkyl groups, such as cyclopentylmethyl, cyclopentylethyl, cyclohexylmethyl, etc., so long as the total number of carbon atoms is not exceeded. The term "alkoxy" refers to an —O-alkyl radical, such as, for example —O-Me, —O-Et, —O—Pr, and so on. The term "hydroxyalkyl" refers to an alkyl group substituted with one or more hydroxyl, such as, for example, hydroxymethyl, 1-hydroxyethyl, 2-hydroxyethyl, 1,2-dihydroxyethyl, and so forth. The term "thioalkyl" refers to an —S-alkyl group, such as, for example, example —S-Me, —S-Et, —S—Pr. The term "haloalkyl" means alkyl, substituted with one or more halogen atoms, such as trifluoromethyl, chloromethyl, 2,2,2-trifluoroethyl, 1,1,2,2,2,-petanfluoroethyl, and so on. The term "aminoalkyl" means alkyl, substituted with an amine group ($NH_2$), such as, for example, aminomethyl, 1-aminoethyl, 2-aminoethyl, 3-aminopropyl and so forth. The term "alkoxyalkyl" refers to an alkyl group, substituted with an alkoxy group, such as, for example, methoxymethyl, ethoxymethyl, methoxyethyl, and so forth. As used herein, the term "alkylaminoalkyl" refers to an alkyl group substituted with an alkylamine group, such as, for example, N-methylaminomethyl, N,N-dimethylaminomethyl, N,N-methylpentylaminomethyl, 2-(N-methylamino)ethyl, 2-(N,N-dimethylamino)ethyl, and so forth.

The term "halogen" or "halo" means F, Cl, Br, or I.

The term "nitro" means (—$NO_2$).

The term "amine" or "amino" used alone or as part of a larger moiety refers to unsubstituted (—$NH_2$). The term "alkylamine" refers to mono- (—NRH) or di-substituted (—$NR_2$) amine where at least one R group is an alkyl substituent, as defined above. Examples include methylamino (—$NHCH_3$), dimethylamino (—$N(CH_3)_2$). The term "arylamine" refers to a mono (—NRH) or di-substituted (—$NR_2$) amine, where at least one R group is an aryl group as defined below, including, for example, phenylamino, diphenylamino, and so forth. The term "heteroarylamine" refers to a mono (—NRH) or di-substituted (—$NR_2$) amine, where at least one R group is a heteroaryl group as defined below, including, for example, 2-pyridylamino, 3-pyridylamino and so forth. The term "aralkylamine" refers to a mono (—NRH) or di-substituted (—$NR_2$) amine, where at least one R group is an aralkyl group, including, for example, benzylamino, phenethylamino, and so forth. The term "heteroaralkylamine" refers to a mono (—NRH) or di-substituted (—$NR_2$) amine, where at least one R group is a heteroaralkyl group. As used herein, the term "alkylaminoalkyl" refers to an alkyl group substituted with an alkylamine group. Analogously, "arylaminoalkyl" refers to an alkyl group substituted with an arylamine, and so forth, for any substituted amine described herein.

The term "alkenyl" used alone or as part of a larger moiety include both straight and branched chains containing at least one double bond and two to ten carbon atoms (i.e. 2, 3, 4, 5, 6, 7, 8, 9, or 10 carbon atoms), as well as cyclic, non-aromatic alkenyl groups such as cyclopropenyl, cyclobutenyl, cyclopentenyl, cyclopentadienyl, cyclohexenyl, cyclohexadienyl, etc. As used herein, alkenyl groups also include mixed cyclic and linear alkyl groups, such as cyclopentenylmethyl, cyclopentenylethyl, cyclohexenylmethyl, etc., so long as the total number of carbon atoms is not exceeded. When the total number of carbons allows (i.e. more than 4 carbons), an alkenyl group may have multiple double bonds, whether conjugated or non-conjugated, but do not include aromatic structures. Examples of alkenyl groups include ethenyl, propenyl, butenyl, butadienyl, isoprenyl, dimethylallyl, geranyl and so forth.

The term "aryl" used alone or as part of a larger moiety, refers to mono-, bi-, or tricyclic aromatic hydrocarbon ring systems having five to fourteen members, such as phenyl, 1-naphthyl, 2-naphthyl, 1-anthracyl and 2-anthracyl. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl or tetrahydronaphthyl, where the radical or point of attachment is on the aromatic ring. The term "aralkyl" refers to an alkyl substituent substituted by an aryl group. The term "aryloxy" refers to an —O-aryl group, such as, for example phenoxy, 4-chlorophenoxy and so forth. The term "arylthio" refers to an —S-aryl group such as, for example phenylthio, 4-chlorophenylthio, and so forth. The term "aryl" used alone or as part of a larger moiety also refers to aryl rings that are substituted such as, for example, 4-chlorophenyl, 3,4-dibromophenyl and so forth. An aryl group may have more than one substituent, up to the total number of free substitution positions. For example, an aryl group may have 1, 2, 3, 4, or 5 substituents. The substituents may the same or different. Substituents on an aryl group include hydrogen, halogen, alkyl, alkenyl, nitro, hydroxyl, amino, alkylamino, alkoxy, and alkylthio, O-acyl, N-acyl, S-acyl as defined herein.

The term "heteroaryl", used alone or as part of a larger moiety, refers to heteroaromatic ring groups having five to fourteen members, preferably five to ten, in which one or more ring carbons, preferably one to four, are each replaced by a heteroatom such as N, O, or S. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" may be used interchangeably with the term "heteroaryl ring" or the term "heteroaromatic." The term "heteroaralkyl" refers to an alkyl group substituted by a heteroaryl, such as, for example, 2-pyridylmethyl, 3-pyridylmethyl, 1-imidazolomethyl, 2-imidazolomethyl and so forth. The term "heteroaryloxy" refers to an —O-heteroaryl group. The term "heteroarylthio" refers to an —S-aryl group. A heteroaryl group may have more than one substituent, up to the total number of free substitution positions. For example, a heteroaryl group may have 1, 2, 3, 4, or 5 substituents. The substituents may be the same or different. Substituents on a heteroaryl group include hydrogen, halogen, alkyl, alkenyl, nitro, hydroxyl, amino, alkylamino, alkoxy, and alkylthio, O-acyl, N-acyl, S-acyl as defined herein.

The term "O-acyl" refers to an "—O—C(O)-alkyl," "—O—C(O)-aryl," or "—O—C(O)— heteroaryl" group. The term "N-acyl" refers to an "—NR—C(O)-alkyl," "—NR—C(O)-aryl," or "—NR—C(O)-heteroaryl" where R is an alkyl, hydroxyl, or alkoxy group. The term "S-acyl" refers to "—S—C(O)-alkyl," "—S—C(O)-aryl," or "—S—C(O)-heteroaryl." The term "N—O-acyl" refers to an "N—O—C(O)-alkyl," "N—O—C(O)-aryl," or "N—O—C(O)-heteroaryl" group.

As used herein, a "substituted" structure refers to a chemical structure where a hydrogen atom has been replaced by a substituent. A "substituent" is a chemical structure that replaces a hydrogen atom on the substituted structure. The term "substituent" does not imply that the substituent is smaller than the substituted structure.

Another embodiment of the invention is a combination for enhancing exon skipping in an mRNA of interest, comprising a compound from Table 1 and an AO that is specific for an exon that is to be skipped, and, optionally, a pharmaceutically acceptable carrier. In one embodiment, the combination comprises a dosage form of a compound of Table 1 and a dosage form of an AO that is specific for the exon which is to be skipped.

Suitable pharmaceutically acceptable carriers will be evident to a skilled worker. For guidance, see, e.g., Remington's Pharmaceutical Sciences (supra).

Another embodiment of the invention is a kit for carrying out one of the methods of the invention. For example, a kit for enhancing exon skipping in a pre-mRNA of interest can comprise a compound from Table 1 and an AO that is specific for an exon splicing sequence in the mRNA of interest. A kit for enhancing exon skipping in a muscle dystrophin mRNA in a subject that has Duchenne Muscular Dystrophy (DMD), in an animal model of DMD, or in an animal that is not necessarily an animal model for DMD, such as a monkey, can comprise a dosage form of a compound of Table 1 and a dosage form of an AO that is specific for the exon which is to be skipped.

A kit of the invention can comprise a device, composition, or other means for administering the agents of the invention to a subject. A kit suitable for a therapeutic treatment in a subject may further comprise a pharmaceutically acceptable carrier and, optionally, a container or packaging material.

Optionally, the kits comprise instructions for performing the method, and/or a notice in the form prescribed by a governmental agency regulating the manufacture, use or sale of pharmaceuticals or biological products (such as the FDA), which notice reflects approval by the agency of manufacture, use or sale for human administration. In addition, agents in a kit of the invention may comprise other therapeutic compounds, for combination therapy. Other optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form for use as therapeutics, or in single reaction form for diagnostic use.

Methods for making and using antisense and/or small molecule reagents, and for testing them for desirable properties, are conventional and well-known in the art. Guidance in performing some of the methods of the invention is provided, for example, in Sambrook et al., Molecular Cloning, A Laboratory Manual (volumes Cold Spring Harbor Laboratory Press, USA or Harlowe and Lane, Antibodies a Laboratory Manual 1988 and 1998, Cold Spring Harbor Laboratory Press, USA. These and other references cited herein which provide guidance for performing methods related to the present invention are incorporated by reference herein in their entirety.

In the foregoing and in the following examples, all temperatures are set forth in uncorrected degrees Celsius; and, unless otherwise indicated, all parts and percentages are by weight.

EXAMPLES

Example I. Identification of Small Molecule Enhancers of Antisense Mediated Exon Skipping In this Example, we describe the implementation of a strategy to identify compounds that synergize with AO to promote exon skipping and the follow-up of a lead hit, dantrolene, in mutation repair of specific mouse and human models of Duchenne muscular dystrophy in vitro and in vivo. In contrast to prior screens aimed at identifying small molecules which impact exon skipping, our screen is unique at least because it relies on robust quantitation of a skipping reporter in the context of a muscle lineage cell in the presence and absence of suboptimal AO. These screens were performed using a mouse muscle cell line (C2C12) expressing a human DMD exon 50 GFP based reporter [18] selected to minimize experimental variation and sensitivity in the context of an automated and quantitative fluorescent scanning system.

Figure 1:
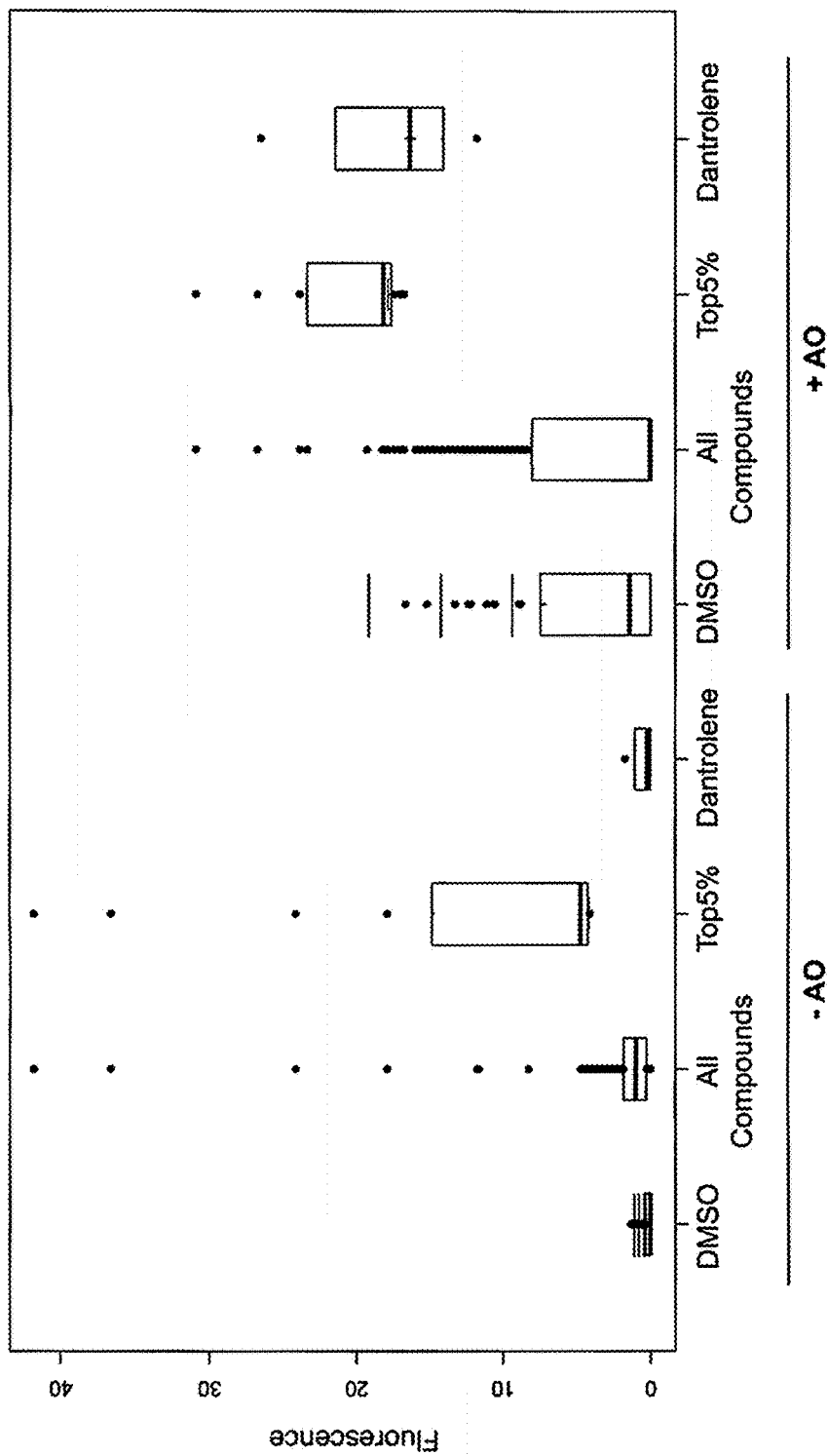
FIG. 1 shows that high throughput screening identifies dantrolene as a modulator of antisense oligo (AO) mediated human DMD exon 50 skipping. Small molecule libraries were screened for exon skipping promoting activity in C2C12 myoblasts expressing a human DMD exon 50 GFP based reporter [18]. Using an automated and quantifiable system the BioMol chemical library (n=503) was screened at 10 uM concentration both in the presence and absence of 2'-O-methyl 27-mer AO [5' AACUUCCUCUUUAACA-GAAAAGCAUAC 3', (SEQ ID NO:1)] targeting the splice donor site of human DMD exon 50. In the reporter cells, successful skipping of DMD exon 50 creates in-frame GFP expression. Number of cells that were fluorescing was quantified using a high content cell imager in 384 well plate format. Fluorescence was normalized by subtracting the average fluorescence value of the carrier (DMSO) controls. Fluorescence readouts are plotted for the BioMol library screen both with (+AO) and without (−AO) from Source Plate 1 (containing the Orphan Ligand, Ion Channel, Enzyme Inhibitor, and Endocannabanoid libraries, n=300). Each point for the DMSO controls, all compounds, and the Top 5% from Source Plate 1 (n=15) represents the average normalized fluorescence of 6 replicates in the −AO screen and 3 replicates in the +AO screen. In the with AO screen, dantrolene had three fluorescence measurements that were averaged, and this average compared to the average fluorescence of the other compounds in the top 15 (top 5%) of the screen. Dantrolene was identified to have enhanced exon skipping activity in the screen+AO, while its activity was indistinguishable from the DMSO controls in the −AO screen. Individual points for dantrolene are plotted with the bold horizontal line indicating the median. The short horizontal lines interspersed among the data points indicate 1, 2, and 3 standard deviations away from the DMSO treatment mean fluorescence.

The BioMol small molecule library (n=503) was screened at an effective concentration of 10 uM (dissolved in DMSO) for all compounds both in the presence and absence of 2'-O-methyl AO (AON6) targeting the splice donor site of human DMD exon 50. AO was added prior to small molecule incubation in an effort to identify molecules that facilitate AO skipping rather than AO delivery. The fluorescence induced by each compound was normalized to a vehicle controls per plate to correct for plate to plate variability. Fluorescence was averaged across replicate plates (n=6 without AO screen, n=3 with AO screen). Compounds were rank ordered based on average intensity of fluorescence and difference between the without AO and with AO screen (FIG. 1 and Table 2).

The lipid library component of the BioMol library had high variability and these compounds were not analyzed. Within the top 5% of compounds from the remaining BioMol library screened in the context of AO, there was a significant over-representation of compounds modulating intracellular calcium, including dantrolene and ryanodine, both known to target the ryanodine receptor. (Z=5.49; Table 3). We found this intriguing given that calcium signaling has been previously identified as a modulator of mRNA splicing machinery in other settings [19].

TABLE 2

Top 5% of compounds from the BioMol high throughput screen either with or without AON6. Compounds were rank ordered based on the average normalized fluorescence and the top 5% (n = 15) from source plate 1 are given for the with and without AO high throughput screen.

| BioMol Screen Results: Top 5% of Compounds in the With AON6 Screen | | | | | | | |
|---|---|---|---|---|---|---|---|
| Compound | Fluorescence Plate 1 | Fluorescence Plate 2 | Fluorescence Plate 3 | Average Fluorescence (n = 3) | Standard Deviation | Library | Target |
| 6-FORMYLINDOLO [3,2-b] CARBAZOLE | 30.05 | 30.08 | 32.59 | 30.90 | 1.46 | Orphan Ligand | Endogenous |
| CYCLOPIAZONIC ACID | 29.57 | 33.40 | 17.24 | 26.74 | 8.44 | Ion Channel | Intracellular Calcium |
| H-7 | 29.03 | 30.45 | 12.11 | 23.87 | 10.20 | Enzyme Inhibitor | Inhibits PKA, PKG, MLCK, and PKC. |
| U-0126 | 17.87 | 35.65 | 16.65 | 23.39 | 10.63 | Enzyme Inhibitor | MEK inhibitor. |
| AG-494 | 19.38 | 25.36 | 25.25 | 23.33 | 3.42 | Enzyme Inhibitor | Tyrosine kinase inhibitor. |
| HARMALINE HCl | 15.00 | 42.55 | 0.22 | 19.26 | 21.48 | Orphan Ligand | Possible endogenous beta-carboline derivative |
| DANTROLENE | 16.32 | 11.76 | 26.51 | 18.20 | 7.55 | Ion Channel | Intracellular Calcium |
| PINACIDIL | 15.64 | 27.20 | 11.56 | 18.13 | 8.11 | Ion Channel | Potassium Channels |
| PROCAINAMIDE | 13.80 | 19.66 | 20.81 | 18.09 | 3.76 | Ion Channel | Sodium Channels |
| 1,1'-ETHYLIDENE-bis-L-TRYPTOPHAN | 20.72 | 11.15 | 22.18 | 18.02 | 5.99 | Orphan Ligand | Bioactive tryptophan derivative |
| TYRPHOSTIN 46 | 8.61 | 30.70 | 14.09 | 17.80 | 11.50 | Enzyme Inhibitor | EGF receptor kinase, p56, and PDGF receptor kinase inhibitor. |
| AG-825 | 17.24 | 23.38 | 11.53 | 17.38 | 5.93 | Enzyme Inhibitor | HER1-2 tyrosine kinase inhibitor. |
| AG-490 | 7.17 | 30.27 | 13.54 | 16.99 | 11.93 | Enzyme Inhibitor | JAK-2 tyrosine kinase inhibitor. |
| H-9 | 18.09 | 19.17 | 13.25 | 16.84 | 3.16 | Enzyme Inhibitor | Protein kinase inhibitor |
| RYANODINE | 7.93 | 28.86 | 13.31 | 16.70 | 10.87 | Ion Channel | Intracellular Calcium |

| BioMol Screen Results: Top 5% of Compounds in the Without AON6 Screen | | | | | | | | |
|---|---|---|---|---|---|---|---|---|
| Compound | Fluorescence Plate 1 | Fluorescence Plate 2 | Fluorescence Plate 3 | Fluorescence Plate 4 | Fluorescence Plate 5 | Fluorescence Plate 6 | Average Fluorescence (n = 6) | Standard Deviation |
| GF 109203X | 22.19 | 15.01 | 13.67 | 66.78 | 64.46 | 66.48 | 41.76 | 27.36 |
| Ro 31-8220 | 17.56 | 50.61 | 46.79 | 38.49 | 31.21 | 34.94 | 36.60 | 11.81 |
| HARMALINE HCl | 31.97 | 27.56 | 27.06 | 22.50 | 16.09 | 19.75 | 24.15 | 5.80 |
| INDIRUBIN | 4.64 | −0.42 | 6.43 | 89.35 | 3.42 | 3.88 | 17.88 | 35.08 |
| 5-IODOTUBERCIDIN | −0.41 | 6.65 | 9.13 | 18.27 | 30.70 | 6.10 | 11.74 | 11.08 |
| DICHLOROBENZAMIL | 22.19 | 15.01 | 13.67 | 4.78 | 7.44 | 6.66 | 11.63 | 6.58 |
| INDIRUBIN | 24.66 | 2.02 | 6.44 | 8.35 | 6.60 | 1.51 | 8.26 | 8.48 |
| WORTMANNIN | 4.99 | 3.07 | 4.23 | 5.92 | 6.44 | 3.78 | 4.74 | 1.29 |
| Docosatetra-7Z,10Z,13Z,16Z-enoyl dopamine | −1.65 | 5.21 | 7.47 | 2.30 | 9.50 | 5.44 | 4.71 | 3.94 |
| TETRANDRINE | 3.15 | 2.41 | 5.39 | 4.64 | 5.03 | 6.64 | 4.54 | 1.54 |
| AG-879 | 1.23 | 3.24 | 3.46 | 6.94 | 8.93 | 2.06 | 4.31 | 2.99 |
| CANTHARIDIN | 11.40 | −1.04 | 0.63 | 5.55 | 4.34 | 4.45 | 4.22 | 4.33 |
| AG-494 | 5.92 | 1.23 | 1.65 | 7.58 | 3.54 | 5.26 | 4.20 | 2.50 |
| NIGULDIPINE | 5.07 | 1.34 | 3.34 | 8.06 | 6.06 | 0.84 | 4.12 | 2.80 |
| Oleoyl dopamine | 2.78 | 1.51 | 12.34 | 3.21 | 3.30 | 1.32 | 4.08 | 4.14 |

TABLE 2-continued

Top 5% of compounds from the BioMol high throughput screen either with or without AON6. Compounds were rank ordered based on the average normalized fluorescence and the top 5% (n = 15) from source plate 1 are given for the with and without AO high throughput screen.

BioMol Screen Results:
Top 5% of Compounds in the Without AON6 Screen

| Compound | Library | Target |
|---|---|---|
| GF 109203X | Enzyme Inhibitor | Protein kinase C inhibitor. |
| Ro 31-8220 | Enzyme Inhibitor | Protein kinase C inhibitor. |
| HARMALINE HCl | Orphan Ligand | Possible endogenous beta-carboline derivative |
| INDIRUBIN | Enzyme Inhibitor | GSK-3beta and CDK5 inhibitor. |
| 5-IODOTUBERCIDIN | Enzyme Inhibitor | Inhibits ERK2, adenosine kinese, CK1, CK2, and insulin receptor kinase. |
| DICHLOROBENZAMIL | Ion Channel | Calcium Channels |
| INDIRUBIN | Orphan Ligand | Endogenous |
| WORTMANNIN | Enzyme Inhibitor | Phosphatidylinositol 3-kinase inhibitor. |
| Docosatetra-7Z,10Z,13Z,16Z-enoyl dopamine | Endocannabinoid | — |
| TETRANDRINE | Ion Channel | Calcium Channels |
| AG-879 | Enzyme Inhibitor | Tyrosine kinase inhibitor. |
| CANTHARIDIN | Enzyme Inhibitor | PP1 and PP2A inhibitor. |
| AG-494 | Enzyme Inhibitor | Tyrosine kinase inhibitor. |
| NIGULDIPINE | Ion Channel | Calcium Channels |
| Oleoyl dopamine | Endocannabinoid | — |

TABLE 3

Compounds that affect intracellular calcium levels are overrepresented in the top 5% in the BioMol with AON6 high throughput screen. Library subsets are overrepresented in the Top 5% of the BioMol screen both with and without AO as determined by analyzing the rate of appearance in randomly selected subsets (N = 20; 15 elements per subset). Biomol with AO screen has an enrichment of intracellular calcium channels (5 standard deviations above what is expected given random sampling) whereas BioMol without AO screen has a slight over-representation of the enzyme inhibitor library (2 standard deviations above what is expected given random sampling).

| BioMol IntraLibrary Composition | Rate of Appearance in Randomly Selected Subsets (N = 20); 15 elements per sunset) Average | Standard Deviation | BioMol Screen Results for Top 5% (N = 15 compounds) +AO Distritribution | −AO Distribution | Z-Score $[(N_o - \bar{A}_c \gamma \sigma_e)]$ +AO Z-Score | −AO z-Score |
|---|---|---|---|---|---|---|
| Orphan Ligand Library | 84 | 4.19 | 1.72 | 3 | 2 | −0.69 | −1.27 |
| Intracellular Calcium Channels | 7 | 0.19 | 0.51 | 3 | 0 | 5.49** | −0.37 |
| Calcium Channels | 25 | 1.05 | 1.07 | 0 | 3 | −0.98 | 1.82 |
| Potassium Channels | 23 | 1.29 | 0.96 | 1 | 0 | −0.30 | −1.34 |
| Sodium Channels | 11 | 0.90 | 1.14 | 1 | 0 | 0.08 | −0.80 |
| Misc. Channels | 6 | 0.62 | 1.36 | 0 | 0 | −0.46 | −0.46 |
| Enzyme Inhibitor Library | 84 | 4.29 | 1.62 | 7 | 8 | 1.68 | 2.30* |
| Endocannabinoid Library | 60 | 3.48 | 1.97 | 0 | 2 | −1.77 | −0.75 |
| Total # of Compounds | 300 | — | — | 15 | −15 | | |

Figure 5:
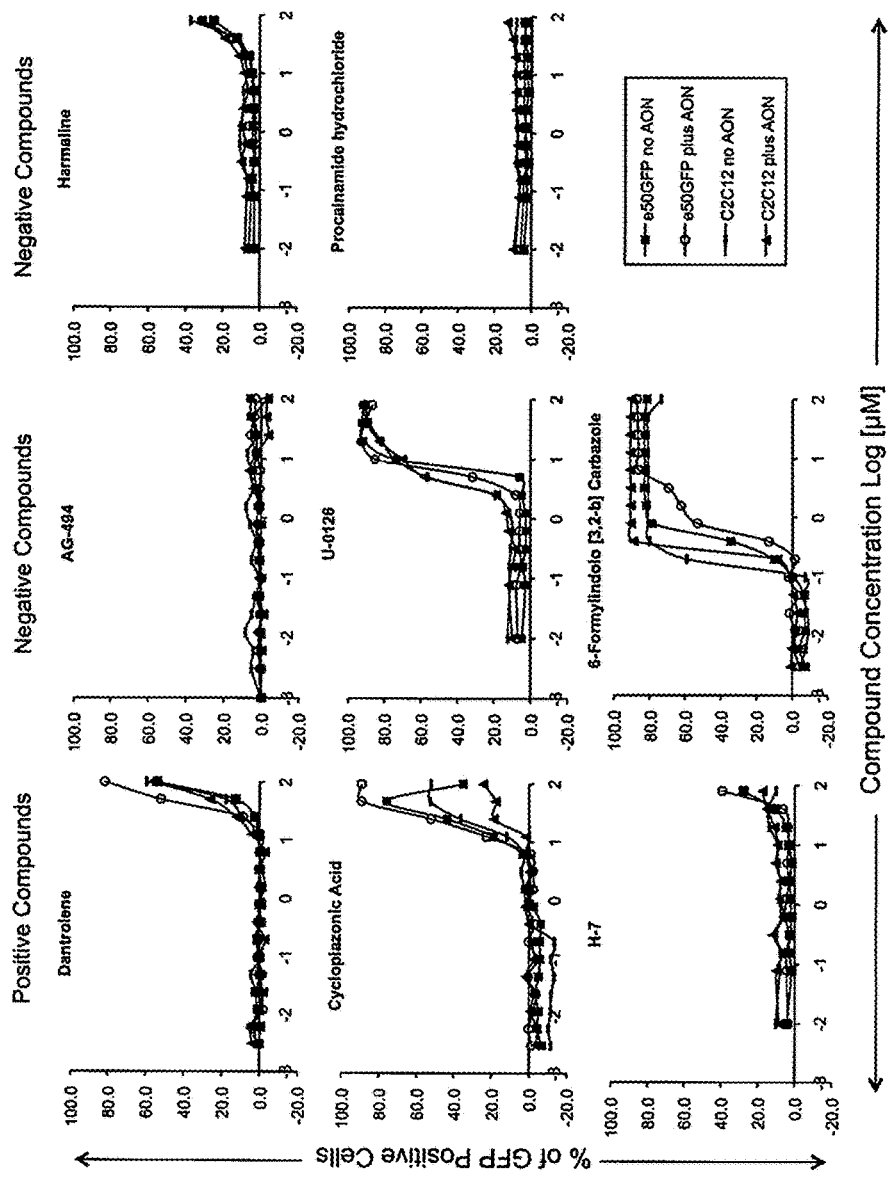
FIG. 5 shows the identification of positive compounds after 12 or 16 point titrations on the DMD exon 50 reporter cell line. Secondary screening was performed on 8/15 compounds to evaluate synergy with AON6 to enhance human exon 50 skipping. 12 or 16 point titrations of compounds were added to the Ex50-GFP and C2C12 myoblasts either with or without AON6. To be considered positive compounds must exhibit a dose response and >10% increased fluorescence in the Ex50-GFP reporter line with AO as compared to the without AO condition.

$N_o$ # of observed compounds in each group for BioMol Top 5% (either with or without AO)
$\bar{A}_c$ Average # of compounds expected per group over 20 randomly selected subsets
$\sigma_e$ Standard deviation of # compounds expected in each group over 20 randomly selected subsets Eight of the top nine top hits from the screen with AO were screened in a secondary assay with 12 or 16 point titrations using the Ex50-GFP reporter C2C12 cells in the presence or absence of AON6. Of the 8 compounds that were selected for secondary screening only 3 exhibited: 1) 10% increase in fluorescence in the Ex50-GFP+AO compared to the reporter line without AO and 2) evidence of a dose response. These three compounds were cyclopiazonic acid, dantrolene, and H-7 (FIG. 5). Dantrolene was of high interest given that it is the only FDA approved drug of the 3 and is still currently being used as a chronic treatment for malignant hyperthermia and muscle spasticity [20, 21]. Additionally, a previous study investigated oral dantrolene as a potential therapy for DMD patients, based on its potential to rectify calcium signaling defects in DMD muscle, and found that after 2 years of daily treatment creatine kinase levels slightly reduced, and there was a modest improvement on the manual muscle test without substantial harmful side effects [22]. Dantrolene treatment of mdx mice has similarly been reported to lower CK values [23]. Therefore, dantrolene was an attractive first candidate to evaluate the effects on exon skipping in vivo in mdx mouse and in the context of human DMD mutations. Variants or alternative formulations of dantrolene are also shown herein to be effective, or would be expected by skilled workers to be effective. These include, e.g., Revonto, azumolene (which is more water soluble than dantrolene), and others.

Figure 2:
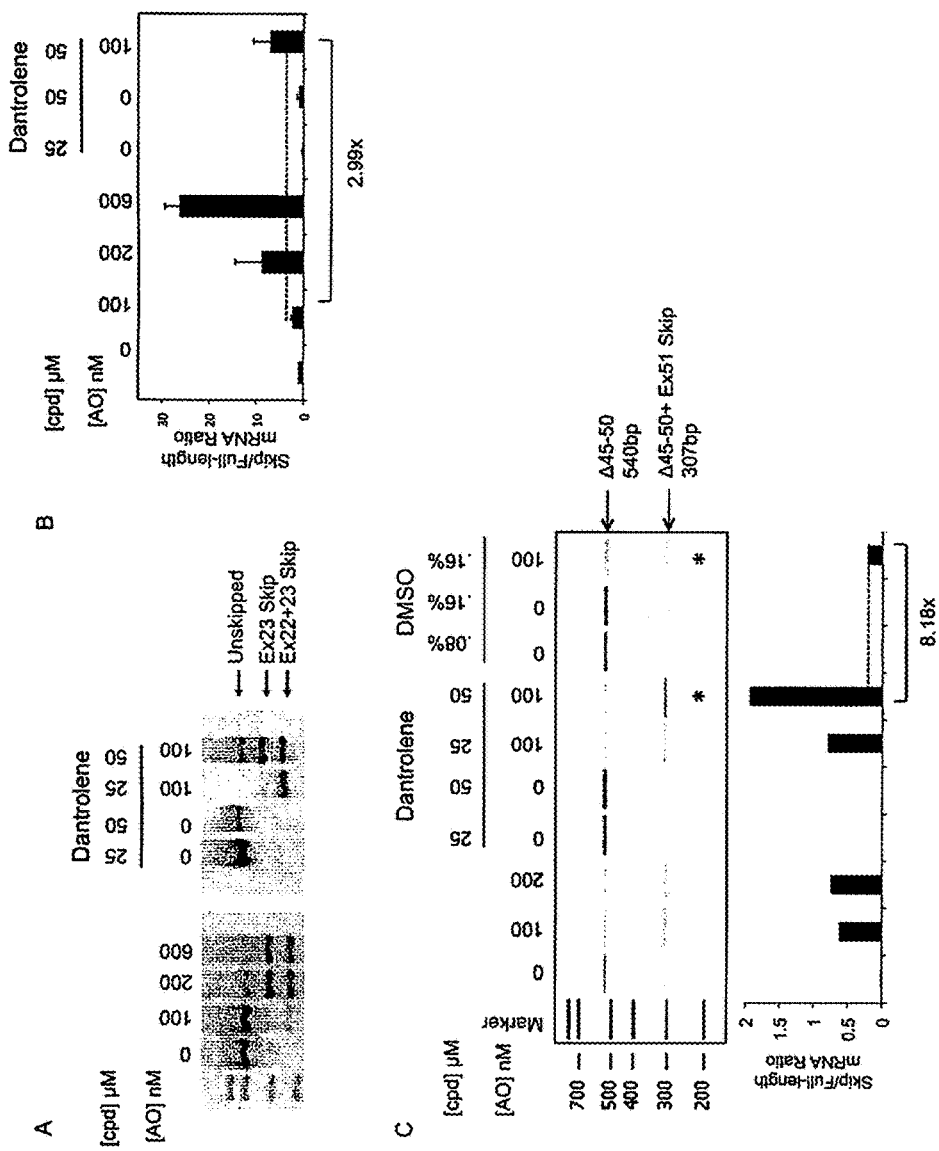
FIG. 2 shows that Dantrolene synergizes with AO to increase DMD exon skipping in mouse and human DMD mutant cells. (A) Differentiated primary mouse myotubes were transfected either with 100 nM 2'-O-methyl M23D, which targets exon 23 splice donor region or mock transfected for 24 hours after which the transfection reagent was removed, and myotubes were treated with different concentrations of Dantrolene for 48 hours. Nested RT-PCR was performed on cDNA between exons 20-26, as previously described [6]. The 901 bp band is the full-length mRNA product, the 688 bp mRNA product is a single skip of exon 23, and the 550 bp mRNA product is a double skip of exons 22 and 23. (B) Mouse Dmd exon 23-skipped transcript levels were quantified using a taqman assay with primer-probe sets spanning the splice junction created by an exon 23 skip (22-24 join) relative to primers amplifying the splice junction of exons 22 and 23 (representing the full length mRNA), as previously described [25]. Data from each primer-probe set was normalized to the ribosomal gene 36B4, and the ratios are displayed as the fold change of the skip/full length mRNA levels relative to the mock treated controls. Error bars represent standard deviation of qRT-PCR triplicates. (C) Patient derived fibroblasts with exon 45-50 deletion (confirmed by microarray, see FIG. 6) were immortalized with lentiviral hTERT and transduced with inducible lentiviral MyoD [26]. Cells were grown to confluence, induced for MyoD activity, and fused for 10 days in low serum differentiation media. On Day 7, h51AON [5' UCAAGGAAGAUGGCAUUUCU 3'] (SEQ ID NO:2) (same sequence as Pro051) within human exon 51 was added at concentrations indicated. Twenty-four hours later Dantrolene or vehicle was added. Cells were harvested 2 days later and total RNA isolated. RT-PCR amplified a fragment of cDNA from exons 42-53 which was followed by a nested PCR to generate a fragment spanning exons 43-52. The 540 bp product is the full length DMD mRNA species and the 307 bp product indicates the exon 51 skip isoform. Quantitation was performed using the Agilent Bioanalyzer and represented as the skip/full-length mRNA ratio.

Dantrolene enhancement of AO directed DMD exon skipping was assessed in both mouse and human primary muscle cell systems in vitro. In primary fused mouse myotubes dantrolene synergized with a 2'-O-methyl AO M23D (overlapping splice donor site from +02-18) to enhance Dmd exon 23 skipping. Increasing concentrations of M23D shifted the Dmd mRNA species from an unskipped form to either exon 23 skipped or dual 22 and 23 skipped forms, both of which are in frame and lack exon 23 which contains the mdx premature stop mutation. A sub-optimal dose of M23D AO was established as 100 nM in order to approximate a dose that generates 20% of optimal skipping in fused myotubes, and used to measure potentiation of exon 23 skipping. Optimal skipping was typically achieved in a dose range of 200-600 nM M23D. After incubation with subop-timal M23D, the complex was removed, and 25-50 uM dantrolene was added for a sufficient time to allow for the complete transcription of new Dmd mRNA species [24]. RNA was extracted and the mRNA from exons 20-26 was assessed for exon 23 skipping by RT-PCR. Dantrolene increased the amount of exon 23 skipped product at both 25 and 50 uM concentrations (FIG. 2a). Dmd exon 23 skipping was quantitated in these same RNA samples in a taqman based assay with primer-probe sets spanning the Dmd splice junctions of exons 22-24 (exon skip specific junction) and exons 22-23 (full length specific junction). Data from each primer-probe set were normalized to the ribosomal gene 36B4, and the ratios are displayed as the fold change of the skip/full length mRNA levels relative to the mock treated controls [25]. Dantrolene increased Dmd exon 23 skipping 3 fold in combination with the suboptimal dose of 100 nM AO M23D as compared to mouse myotubes treated with AO alone (FIG. 2b). Addition of dantrolene in the absence of AO failed to cause exon 23 skipping, consistent with it acting synergistically with AO to promote exon 23 skipping.

Figure 6:
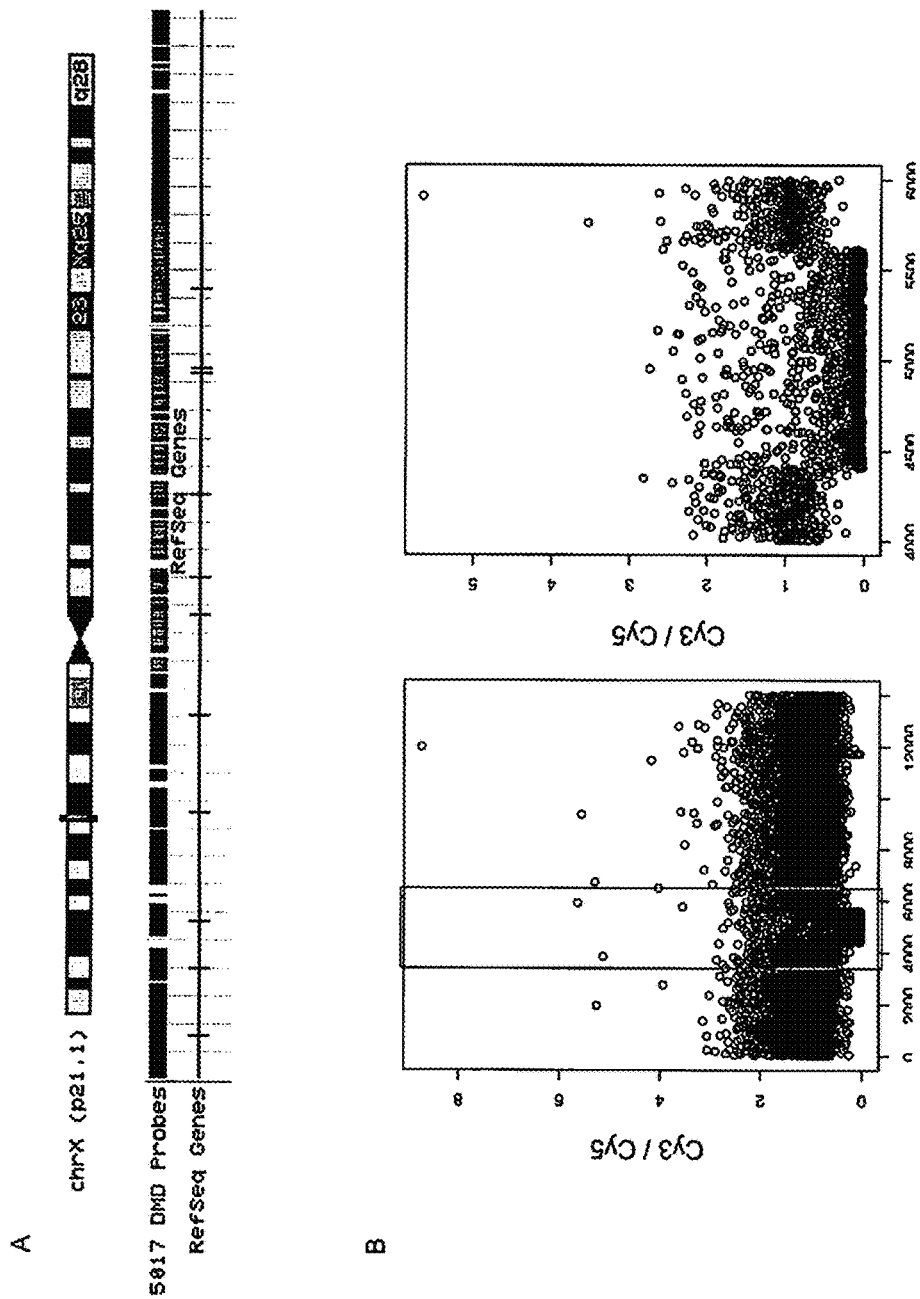
FIG. 6 shows that a custom CGH array confirms deletion breakpoints in GM05017. A custom CGH array was designed with 14022 probes tiling the DMD gene with a resolution of approximately 1 probe every 160 bp. Probe number one maps to genomic position chrX:31047266 and probe 14022 maps to genomic position chrX:33267570. Genomic DNA from the GM05017 was labeled with Cy3, and non-mutated human genomic DNA was labeled with Cy5 and were co-hybridized to the custom designed array.

Dantrolene treatment also increased DMD exon skipping in a disease relevant human mutational context using reprogrammed primary DMD patient fibroblasts fused to differentiated myotubes. The patient DMD mutation was confirmed as an exon 45-50 deletion predicted to be rendered in frame by skipping DMD exon 51, using a custom 15,000 probe CGH array (FIG. 6). Patient fibroblasts were transduced with HTERT and an inducible MyoD vector [26]. Following tamoxifen induction of MyoD activity and subsequent fusion, the DMD patient derived cells became multi-nucleated and expressed multiple muscle differentiation markers including MHC, myogenin, RyR1 and (mutant) dystrophin at the RNA and/or protein level within six days (FIG. 7), further validating this human DMD culture model. Exon 51 skipping activity was assessed in the context of transfecting an exon 51 2'-O-methyl AO with equivalent sequence to Pro051 seven days after fusion. This AO is directed at an exonic splicing enhancer (ESE) sequence within exon 51. The AO was removed prior to addition of dantrolene and cultures were harvested two days later. A nested RT-PCR was performed between DMD exons 43-52 and levels of exon 51 skipping were determined by quantitating capillary electrophoresis separated fragments representing skipped and unskipped DMD mRNA. We found that dantrolene enhanced exon 51 skipping in the presence of the suboptimal dose of AO by up to 8 fold as compared to the vehicle control (FIG. 2c). Therefore, dantrolene exhibits synergy with two different AOs, targeting differing regions of the DMD mRNA transcript consisting of a splice donor site or potential ESE sequence, in both human and mouse myotube cell culture. Dantrolene's effectiveness regardless of sequence specificity of the AO could be potentially useful given the wide spectrum of treatable mutations that require various AO sequences. Thus, the versatility of dantrolene gives it a wide range of applicability in a clinical setting.

To assess the efficacy of dantrolene as a potentiator of AO mediated exon skipping in an art-recognized in vivo mouse model of DMD, we utilized two separate experimental protocols in which dantrolene was administered systemically in the context of either a single intramuscular or single intravenous injection of AO in mdx mice. See FIG. 15 for a schematic representation of one such protocol. Initially drug synergy was assessed with local intramuscular injections of morpholino AO PMOE23 (overlapping with exon 23 splice donor site +07-18) into the tibialis anterior muscle (TA) of mdv mice. Previous studies indicate that 10 ug of PMOE23 rescues up to 70% of dystrophin positive fibers as assessed by dystrophin immunostain [7]. Therefore, 10 ug PMOE23 was used as a positive control and 2 ug selected as a sub-optimal dose of AO. To evaluate if dantrolene could facilitate exon 23 skipping and restore dystrophin protein expression by synergizing with PMOE23, dantrolene was administered at doses of 10 mg/kg/day or 20 mg/kg/day by intraperotineal injection for nine days following a single intramuscular PMOE23 injection (n=3 mice per group (Table 4).

TABLE 4

Treatment groups for the local administration of PMOE23 in combination with systemic dantrolene.

| Group # | IM PMOE23 (ug) in saline | IP Dantrolene (mg/kg) in 20% DMSO/saline | IP 20% DMSO in saline | # Mice | Sex | Age |
|---|---|---|---|---|---|---|
| 1 | Saline | 10 | – | 3 | F | 15 weeks |
| 2 | Saline | 20 | – | 3 | F | 15 weeks |
| 3 | 10 ug | — | + | 3 | M | 15 weeks |
| 4 | 2 ug | — | + | 3 | F | 15 weeks |
| 5 | 2 ug | 10 | – | 3 | M | 15 weeks |
| 6 | 2 ug | 20 | – | 3 | F | 15 weeks |

The entire TA was harvested on the tenth day and divided for analysis into 6-7 intervals, each of 800 µm length. One half of each of the middle four intervals were pooled to prepare sufficient protein for Western blot analysis (total of 1600 um length). Four central sections from the other half were use for immunofluorescence staining. Western blotting demonstrated that treatment with dantrolene at either dose in combination with 2 ug of PMOE23 increased expression of dystrophin protein to levels observed with the higher 10 ug dose of PMOE23. The induced levels of dystrophin observed represent about 20% of C57 dystrophin levels. Western blots from representative mice are shown in FIG. 3a, whereas average densitometry measurements obtained by quantitating western blots from of all of the mice in each experimental group is shown in FIG. 3b.

Figure 3:
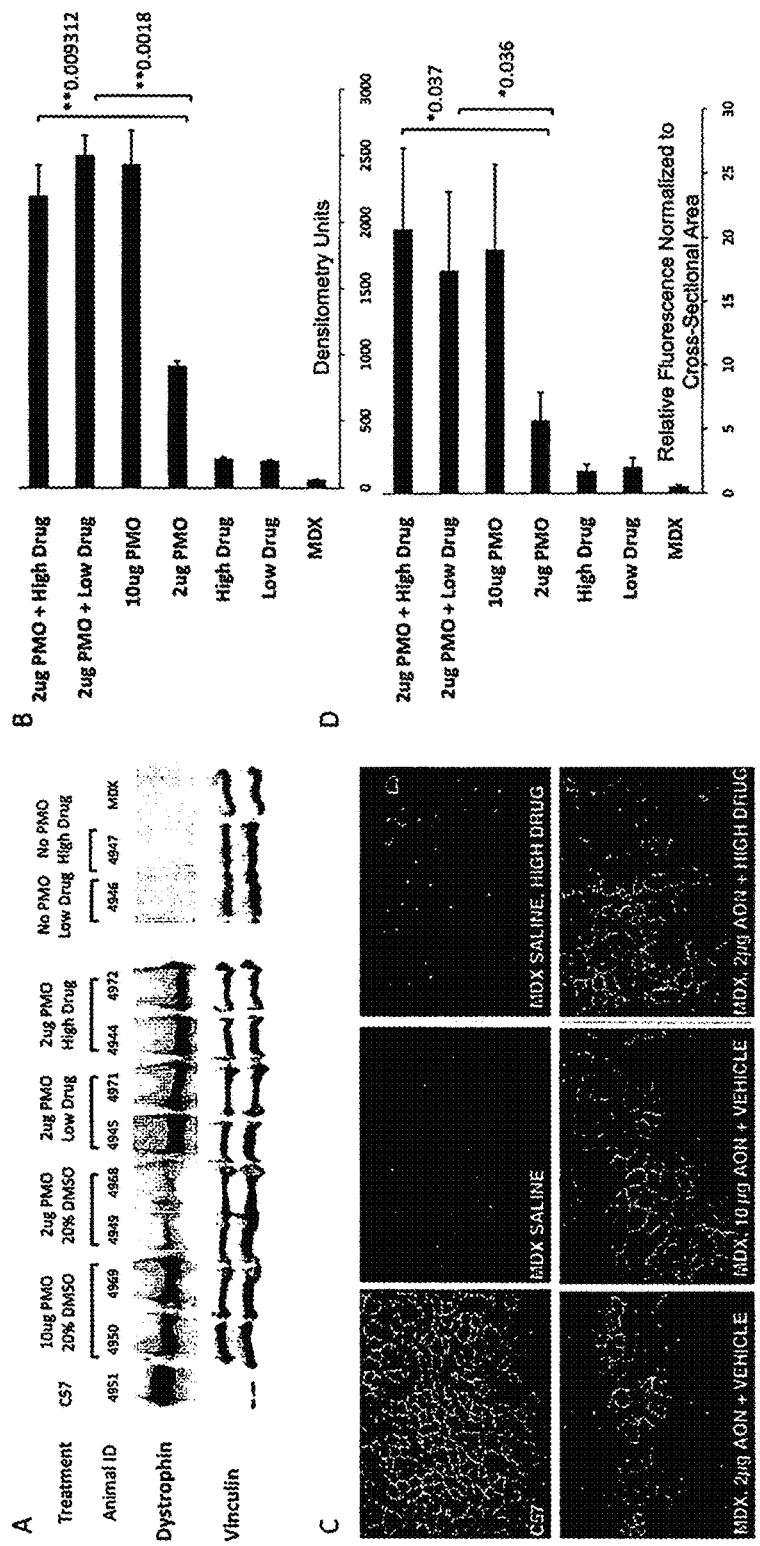
FIG. 3 shows that Dantrolene enhances intramuscularly injected AO DMD mRNA skipping and dystrophin protein expression in mdx mice. One dose of either 10 ug or 2 ug of morpholino M23D in 25 ul PBS was injected into the tibialis anterior (TA) of 6 week old mdx mice on day 1 (n=3 per group). Dantrolene was administered by intraperitoneal injection at either 10 or 20 mg/kg/day for 9 days in a volume of 200 ul every 12 hours. Dantrolene was solubilized in 20% DMSO in normal saline. TA muscle was harvested on Day 11 and immediately frozen in Optimal Cutting Temperature compound (O.C.T.) embedding medium. Serial sections along the TA with intervals 800 microns apart were processed to perform assessments within the TA region with maximal AO delivery. There were 6-7 intervals per TA, and the middle 4 intervals demonstrated exon skipping in treated TA. (A) For Western blot analysis, half of each of the 4 middle intervals were pooled. Dystrophin protein was detected using MANDYS8 (exons 31 and 32) antibody. Control C57 was loaded at 5 ug/well, and 50 ug/well was loaded for other mdx samples. (B) Western blot was quantified by densitometry and plotted as arbitrary densitometry units normalized to vinculin loading control. (C) Immunostaining for dystrophin localization was performed using MANDYS8 of 10 um sections from representative middle sections of the TA, and is consistent with sarcolemmal staining. (D) Data from whole muscle cross sections from C were quantified as total fluorescence, without inclusion of edges with artifactual staining, normalized to surface area scanned. Data are plotted as percent of C57 as control (set at 100). Images were analyzed using Ariol SL-50 (Applied Imaging Corp., San Jose, Calif.). Error bars in B and D represent the standard deviation of 3 mice per group.

Representative immunoflourescence images of TA cross sections stained with anti-dystrophin antibody are shown in FIG. 3c and demonstrate proper localization of dystrophin protein at the sarcolemma in treated samples. Total fluorescence was quantitated from TA sections by scanning four entire cross sections from each of the mice for each experimental group. Quantitation of dystrophin immunofluorescence was highly concordant with western blot quantification. Again, equivalency between the 10 ug dose of PMOE23 and the 2 ug dose of PMOE23 in combination with dantrolene dose was observed. Dantrolene only rescued protein expression in the presence of PMOE23 reflecting synergistic activity of dantrolene with exon skipping PMOE23 in vivo. Quantitation of skipped/unskipped Dmd mRNA using taqman PCR assay in an independent experiment similarly demonstrated that dantrolene synergizes with IM injection of PMOE23 to facilitate exon skipping (FIGS. 8 and 9).

Results from local PMOE23 administration prompted further exploration of dantrolene's efficacy in the context of systemic PMOE23 delivery to mdx mice. This enabled us to assess whether dantrolene in combination with systemic morpholino PMOE23 could enhance Dmd exon 23 skipping and induce dystrophin protein expression in multiple skeletal muscles. A single intravenous dose of 100 mg/kg PMOE23 was used as a positive control. A single intravenous dose of 10 mg/kg AO was used as a sub-optimal dose alone or in combination with twice daily dosing of 10 mg/kg/day of dantrolene intraperitoneally for the subsequent 6 days [7, 27] (n=3 in control groups and n=4 in experimental groups; Table 5).

TABLE 5

Treatment groups for the systemic administration of PMOE23 in combination with systemic dantrolene.

| Group # | Systemic PMOE23 (ug) in saline | IP Dantrolene (mg/kg) in 20% DMSO/saline | IP 20% DMSO in saline | # Mice | Sex | Age |
|---|---|---|---|---|---|---|
| 1 | Saline | 10 | – | 3 | F | 6 weeks |
| 2 | 100 mg/kg (2 mg) | — | + | 3 | M | 6 weeks |
| 3 | 10 mg/kg (.2 mg) | — | + | 3 | M | 6 weeks |
| 4 | 10 mg/kg (.2 mg) | 10 | – | 3 | F | 6 weeks |

Figure 4:
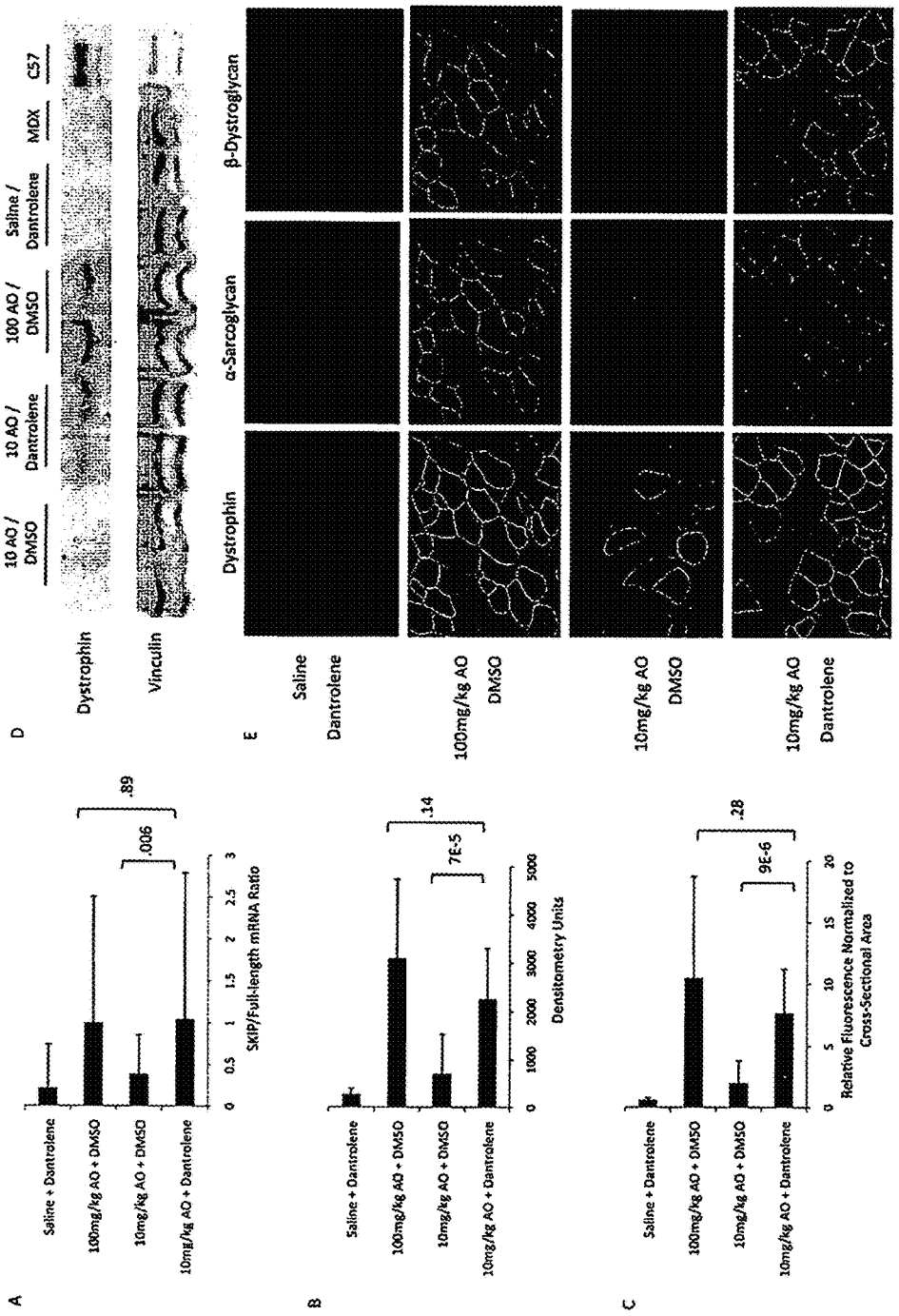
FIG. 4 shows that Dantrolene enhances intravascularly delivered exon 23 AO to promote exon 23 skipping of Dmd mRNA in mdx mice and rescues dystrophin protein and other DGC components. A systemic dose of 100 mg/kg or sub-optimal 10 mg/kg of morpholino M23D (+07-18) was administered by tail vein injection on Day 1. From Day 2-7 Dantrolene was administered intraperitoneally at a dose of 10 mg/kg/day in two divided doses. On Day 8 multiple muscles were harvested for analysis. (A) DMD exon 23 skipping was assessed as in FIG. 3. Skip/full-length mRNA ratio data were combined for all mice and for all initial muscle groups tested (quadricep, gastrocnemius, tibialis anterior and diaphragm). (B) Dystrophin protein was assessed by Western blot (Mandys8) quantitative densitometry for all muscle groups and individual mice (quadricep, gastrocnemius, tibialis anterior and diaphragm). (C) Quantitative immunohistochemistry is plotted as arbitrary units normalized to surface area for each section for all muscle groups and mice using one whole muscle cross section per animal per muscle. (D) Representative Western blot from the gastrocnemius demonstrating appropriate size of dystrophin. C57 was loaded at one tenth the protein concentration of the other lanes. (E) Immunostaining of serial sections of treated mdx quadricep detects sarcolemmal localization of dystrophin (MANDYS8), alpha-sarcoglycan (NCL-a-sarc) and beta-dystroglycan (NCL-b-DG). Additional immunostain photomicrographs are shown in supplemental FIG. 8 of individual muscle types. Error bars in A-C represent the standard deviation among mice and muscles in each group (n=3 animals or n=12 total observations in saline+dantrolene and 100 mg/kg AO+DMSO; n=4 animals or n=16 observations in 10 mg/kg AO with Dantrolene or DMSO).

Multiple skeletal muscles were harvested for analysis on day 7 including the quadriceps, gastrocnemius, tibialis anterior, diaphragm, triceps and heart. Muscles were assessed for: 1) increased amounts of skipped Dmd exon 23 mRNA species 2) Dystrophin protein rescue by Western blot 3) Dystrophin protein expression by quantitative immunostain, 4) appropriate subcellular localization, and 5) restoration of other components of the dystroglycan complex to the sarcolemmal membrane. To determine if dantrolene enhanced Dmd exon 23 skipping, the quantitative taqman assay was performed on RNA from each skeletal muscle. Dantrolene significantly increased Dmd exon 23 mRNA skipping in an aggregate analysis of all skeletal muscle groups (excluding heart) (FIG. 4A). Analysis of individual muscle groups demonstrated that dantrolene enhanced skipping in the gastrocnemius, TA, diaphragm and quadriceps (FIG. 4a and FIG. 10a). Enhancement was not apparent in the triceps, often targeted less well by AOs. No appreciable skipping was observed in heart muscle under any experimental condition. Western blot analysis for dystrophin protein was concordant with mRNA skipping in all muscle groups analyzed (FIG. 4b and FIGS. 10c,11). Pooled densitometry quantitation of western blots across the quadricep, gastrocnemius, TA and diaphragm for all mice indicates a mean fold increase of 3.1 in dystrophin protein expression when PMOE23 is combined with dantrolene relative to PMOE23 with vehicle (FIG. 4b). Quantitative immunofluorescence supports qRT-PCR and Western blot quantitation (FIG. 4c), and further demonstrates dantrolene enhancement of dystrophin protein expression (FIG. 4d and FIG. 12). Immunostaining with several anti-dystrophin antibodies demonstrate full N and C terminal expression of dystrophin and correct sarcolemmal localization (FIG. 4d and FIG. 13). In addition, sequential serial sections of the quadricep muscle indicate that dystrophin expression reestablishes other components of the DGC: β-dystroglycan and α-sarcoglycan (FIG. 4d, FIG. 10). The levels of α-sarcoglycan and β-dystroglycan expression with 2 ug of PMOE23 and dantrolene are similar to that induced by 10 ug from the higher systemic dose of PMOE23. The ability of rescued dystrophin to recruit other members of the DGC is suggestive of its ultimate functionality in vivo. Taken together these data demonstrate that dantrolene synergizes with suboptimal dosing of systemic PM0E23 to facilitate exon skipping and rescue of dystrophin protein and sarcolemmal DGC expression in multiple muscles.

Our results suggest a model in which dantrolene synergizes with AOs, regardless of sequence specificity and chemistry, to enhance targeted DMD exon skipping. This has been demonstrated both in vitro in mouse and human cell systems, as well as in multiple skeletal muscles with intramuscular and intravenous delivery of PMOE in the mdx mouse. Given the timing of addition of AO and drug, it is unlikely that dantrolene is enhancing uptake of AO. Without wishing to be bound by any particular mechanism, we suggest that it is enhancing exon skipping through interaction with a specific molecular target that is modulating DMD splicing activity. The concept of utilizing small molecules to increase exon skipping efficiency has been demonstrated in a patient with a rare point mutation in DMD exon 31 that disrupts an ESE binding site for the SRp30c splicing factor. The addition of TG003, a specific inhibitor for Clks known to phosphorylate SR proteins increased mutant exon 31 skipping and facilitated dystrophin protein rescue [28]. However this therapeutic strategy is unlikely to be generalizable to broad treatment of DMD patients.

Without wishing to be bound by any particular mechanism, we propose that the mechanism by which dantrolene facilitates exon skipping may be that it functions by targeting the ryanodine receptor, its known molecular target. Ryanodine receptor regulates calcium release from the sarcoplasmic reticulum during excitation-contraction coupling in skeletal muscle. Because calcium signaling is a known regulator of splicing activity, dantrolene modulation of RyR1 mediated calcium flux in muscle is a plausible mechanism of its activity, which we are currently investigating. Further RyR expression on the nucleoplasmic reticulum has been implicated in regulating calcium signaling in the nucleus [29]. Hypernitrosylation of RyR in DMD has been attributed to calcium leak and downstream DMD pathology, possibly from calium regulated protein degradation [30]. A more recently developed class of drugs, called 'rycals' stabilize the cardiac RyR2/calstabin interactions, and are under active development for heart failure treatment to prevent a chronic leak of calcium through RyR2 [31]. Thus, dantrolene and rycals which prevent chronic calcium leak have been proposed as potential therapeutics for DMD. While it is possible that the synergistic action of dantrolene in mdx muscle is secondary to stabilization of proteins necessary for regulating the splicing machinery that were previously being degraded, this is unlikely, as we have observed effects of dantrolene on exon 23 skipping in cultured myotubes from C57BL6 as well as mdx mice. Nonetheless, potential activity of dantrolene resulting from non-splicing related effects of calcium modulation may provide another level of synergy in protecting DMD muscle function.

Studies of long-term dantrolene efficacy in the context of multiple AP injections and functional redouts, in the models presented herein as well as in humans, will confirm the results presented herein, demonstrating that the optimized administration of the agents of the invention improves DMD disease progression.

Example II. Supplementary Studies

A. Materials and Methods
High-Throughput Screen and Secondary Screening in the Reporter Cell Line A stable clone was generated from C2C12 cells transfected with a human exon 50 DMD GFP reporter (ex50GFP) that has been previously described [18]. Ex50GFP reporter myoblasts were seeded into uncoated 384 well plates and were incubated for 4 hours either with or without 300 nM of 2'-O-methyl phosphorothioate AON6 [5'AACUUCCUCUUUAACAGAAAAGCAUAC 3' (SEQ ID NO:1)] targeting the human exon 50 splice donor site. Cells were transfected with AON6 using the FUGENE (Roche) transfection reagent per manufacturer's instructions. Following AON6 incubation, each component of the BioMol library (n=503) was screened at 10 uM concentration with a final concentration of the DMSO carrier being 1%. Forty-eight hours later fluorescence was measured using the MicroXpress high content imager and analyzed using MetaXpress. Immediately preceding imaging, DNA was stained with Hoescht for 30 min. The BioMol screen without AO (−AO) was performed in 6 replicates, and the with AO (+AO) screen was performed in 3 replicates. For the screen analysis raw fluorescence values were normalized to carrier controls present on each plate by subtracting the values. Negative fluorescence values were set to 0. The data from each compound were averaged from all replicates. For secondary screening by 12 or 16 point dose response, Ex50GFP myoblasts or C2C12 cells without the reporter were seeded on uncoated 384 well plates. A sub-optimal dose of AON6 targeting DMD exon 50 was added for 4 hours. Following the 4 hour incubation, a compound dilution was added (beginning at 100 uM with 1:1 dilutions) for either 12 or 16 points. After a 48 hour incubation with compounds, DNA was stained with Hoescht, and fluorescence determined using the high content imager and analyzed with MetaXpress.

Primary Cell Culture and Antisense Oligonucleotide Transfection

Primary mouse myoblasts were isolated from the quadriceps of a C57/B16 mouse and were carried in culture with 20% FBS in DMEM and 2 ng/uL FGF. For Dmd exon 23 skipping assays cells were seeded onto extracellular matrix (ECM) (Sigma) coated plates in growth media. On day 2 growth media was removed and fusion media (2% horse serum in phenol red free DMEM) was added. On day 3 a 2-O'-methyl phosphorothioate AO M23D(+02-18) [5' GGCCAAACCUCGGCUUACCU 3' (SEQ ID NO:3)] was transfected into cells using FUGENE per manufacturers instructions. M23D concentrations ranged from 100 nM to 600 nM, with 100 nM M23D representing the sub-optimal dose. On day 4 cells were washed in PBS, and dantrolene (dissolved in DMSO) was added in fresh fusion media. After 48 hours cells were harvested for analysis.

Primary human dermal fibroblasts (GM05017) from a DMD patient were obtained from Coriell and were maintained in growth media (DMEM with 15% FBS, 1% nonessential amino acids, 1% pen/strep). Prior to experiments the genomic DMD deletion between exons 45-50 was confirmed using a custom CGH array with 14022 probes tiling the DMD gene (FIG. 6). Fibroblasts were then immortalized with a lentiviral hTERT and subsequently transduced with a previously described tamoxifen inducible lentiviral MyoD [26] (Kind gift from J. Chamberlain). For exon 51 skipping experiments, reprogrammed fibroblasts were seeded onto laminin coated plates in growth media. On Day 2, 5 uM tamoxifen (Sigma) was added in growth media. On day 3 fusion media (2% horse serum, 2% insulin-transferrin-selenium (Sigma), 1:1 serum free DMEM to Ham's F-10) with 1 uM tamoxifen was added to the cells. A DMD exon 51 2'-O-methyl phosphorothioate AO [5' UCAAGGAAGAUGGCAUUUCU 3' (SEQ ID NO:2)] (MWG Operon) at position +68 to +88 was transfected into cells on Day 7 with ExGen500 (Fermentas) per manufacturer's instructions. AO concentrations ranged from 25-200 nM and the sub-optimal dose of AO was 100 nM. On Day 8 the AO complex was removed and titrations of drug or carrier (DMSO) were added to wells for 48 hours. On day 10 cells were harvested for analysis.

RNA Isolation, RT-PCR and qRT-PCR

RNA was isolated from cell culture using TRIZOL (mouse) and the QIAGEN RNAeasy Microkit (human). RNA was isolated from snap frozen skeletal muscle using the QIAGEN RNAeasy Fibrous Tissue Kit. In the mouse cells cDNA was reverse transcribed from total RNA with OligodT20 (Invitrogen). In the non-quantitative RT-PCR assay a nested PCR was performed between Dmd exons 20-26 as has been previously described [12]. The quantitative taqman assay to assess Dmd exon 23 skipping detection was performed as previously described [25]. In human cells dystrophin cDNA was reverse transcribed with a gene specific primer in DMD exon 54. A nested RT-PCR between DMD exons 43-52 was then performed using previously described primers [10]. For identifying muscle markers in reprogrammed fusing myotubes cDNA was reverse transcribed with OligodT20. Primers for muscle markers were as follows: MyoD (Fwd-5' GCAGGTGTAACCGTAACC 3' (SEQ ID NO:4), Rev-5' ACGTACAAATTCCCTGTAGC 3' (SEQ ID NO:5)), Myosin Heavy Chain (Fwd-5' CAGTAGCCCCATCACATTTG 3'(SEQ ID NO:6), Rev-5' ATAACGCAATGGACAAGTG 3' (SEQ ID NO:7)), Desmin (Fwd-5' CCTACTCTGCCCTCAACTTC 3' (SEQ ID NO:8), Rev-5' AGTATCCCAACACCCTGCTC 3' (SEQ ID NO:9)), Myogenin (Fwd-5' GCCACAGATGCCACTACTTC 3'(SEQ ID NO:10) Rev-5' CAACTTCAGCACAGGAGACC 3'(SEQ ID NO:11)). GAPDH primers are as follows: Fwd-5' GAGCCACATCGCTCAGACAC 3' (SEQ ID NO:12), Rev-5' CATGTAGTTGAGGTCAATGAAGG 3'(SEQ ID NO:13). The thermocycler conditions were 94 C for 2 min, followed by 33 cycles of 94 C for 30s, 62 C for 30s, and 72 C for 30s, with a final extension of 72 C for 10 min. Amplification of the ryanodine receptor required a nested PCR. For the initial PCR the primers were Fwd-5'-CATCAACTATGTCACCAGCATCCG-3' (SEQ ID NO:14) and Rev-5'-GGCTGAACCTTAGAAGAGTC-3' (SEQ ID NO:15) and for the nested PCR the primers were Fwd-5' GAGACCTTCTATGATGCAGC 3' (SEQ ID NO:16) and Rev-5' AGAGCTCGTGGATGTTCTC 3'. (SEQ ID NO:17). Conditions for the initial ryanodine receptor PCR were 95 C for 5 min, 20 cycles of 95 C for 30s, 56 C for 2 min, 72 C for 90s and a final extension of 72 C for 10 min. The nested PCR conditions were 95 C for 5 min, 35 cycles of 95 C for 30s, 59 C for 2 min, 72 C for 90s and a final extension of 72 C for 10 min.

Western Blot

Total protein was isolated from flash frozen skeletal muscle from both the membrane and cytoplasmic fractions. Briefly, ½ of each analyzed muscle were homogenized for 1 minute in 1 mL of ice-cold mito-buffer (0.2 mM EDTA, 0.25 mM sucrose, 10 mM TrisHCl, pH 7.4) with protease/phosphatase inhibitors cocktail (Pierce) and DNAse/RNAse and subjected to low-speed (1500 g) centrifugation for 10 min at 4 C. The supernatant was centrifuged at 100000 g (high speed centrifugation) for 1 hr for isolation of membrane fraction. Isolated membranes and pellet after low speed centrifugation were combined and re-suspended in 300 uL of extraction buffer (50 mM Tris-HCl, pH 7.4, 7 M urea, 2 M thiourea, 4% CHAPS, 2% SDS, 50 mM beta-mercaptoethanol). Protein concentration in solubilized pellet and supernatant after high-speed centrifugation (cytoplasmic fraction) was determined by 2-D Quant Kit (GE Healthcare Life Sciences). 50 ug of total protein from dystrophic mice, or 5 ug from wildtype, was run on a 6% polyacrylamide gel and transferred onto a nitrocellulose membrane for 2 hours at 4 C. The membrane was blocked for 1 hr in 5% milk and then incubated with MANDYS8 (Sigma)1:500 against dystrophin or 1:5000 anti-vinculin (Sigma), a skeletal muscle membrane protein not associated with the DGC that was utilized as a loading control. For analysis dystrophin protein levels were normalized to the vinculin loading control and then pooled across treatment groups or muscles to determine average dystrophin rescue. Dystrophin and vinculin were detected in pellet (miofibrillar/membrane fraction) but not in cytoplasmic fraction.

Immunofluorescence

Unfixed frozen tissue sections were air dried and incubated for 1 hr in MOM Mouse IgG blocking reagent. Sections were incubated with MANDYS8 (Sigma) for dystrophin detection in the rod domain, Ab15277 (Abcam) for dystrophin detection at the C terminus, and Manex 1A (Developmental Studies Hybridoma Bank) for dystrophin detection at the N terminus. Staining for other members of the dystrophin-glycoprotein complex was performed with NCL-a-SARC (Novocastra) for alpha-sarcoglycan and NCL-b-DG (Novocastra) for beta-dystroglycan. Nuclear DNA was visualized with a DAPI stain. Secondary labeling was performed with a FITC labeled anti-mouse or anti-rabbit from Vector labs.

For immunofluorescence in human cell culture terminally fused myotubes were fixed in 2% paraformaldehyde for 15 min and then blocked in 20% goat serum for 1 hour. Cells were washed and then incubated with 1:40 MF20 for detection of myosin heavy chain (Developmental Studies Hybridoma Bank). Cells were then incubated in Alexa488 (Invitrogen) at 1:400 and were mounted in ProLong Gold Antifade Mounting Medium with DAPI (Invitrogen).

In Vivo Administration of Antisense Oligonucleotide and Dantrolene

PMOE23 morpholino (GeneTools) was resuspended in 150 mM sterile saline for intramuscular injections in a 25 uL volume into the tibialis anterior muscle. Intravenous administration of PMOE23 was achieved by tail vein injection of morpholino resuspended in 200 uL sterile saline. Dantrolene sodium salt (Sigma) was resusupended in 100% DMSO stock solutions and diluted in sterile saline (final 20% DMSO) immediately prior to the twice daily intraperitoneal injection in a 200 uL volume.

Statistical Analysis

All statistical analysis were a two-tailed student's t test with unequal variance in EXCEL.

Example III. Further Data

The experiments described in the figures as summarized below were carried out using methods described elsewhere herein, and/or by conventional methods that are well-known by those of skill in the art.

These experiments provide data showing, e.g., that 7 additional small molecule compounds can enhance exon skipping of the DMD gene of human myotube which are exon 51 skippable. See FIGS. 16, 17 and 18. It is noted that two of these molecules (Ryanodine and S107 (called a RYCAL) target the ryanodine receptor, which is also targeted by dantrolene. See FIGS. 19 and 20. Without wishing to be bound by any particular mechanism, it is suggested that this observation supports the conclusion that blocking the ryanodine receptor is one of the mechanisms of this effect.

Furthermore, additional confirmatory tests (titrations) are presented and functional testing of dantrolene is shown in a mouse system. FIG. 21 shows that low dose AO (exon 23 in mouse that repairs the mdx mouse gene) with dantrolene improves skeletal muscle function in a three week experiment relative to a higher dose of AO alone.

An alternative formulation of dantrolene—Revonto—is also shown to be effective.

REFERENCES

1. Emery, A. E., *The muscular dystrophies.* Lancet, 2002. 359(9307): p. 687-95.
2. Emery, A. E., *Population frequencies of inherited neuromuscular diseases—a world survey.* Neuromuscul Disord, 1991. 1(1): p. 19-29.
3. Monaco, A. P., et al., *Detection of deletions spanning the Duchenne muscular dystrophy locus using a tightly linked DNA segment.* Nature, 1985. 316(6031): p. 842-5.
4. Monaco, A. P., et al., *An explanation for the phenotypic differences between patients bearing partial deletions of the DMD locus.* Genomics, 1988. 2(1): p. 90-5.
5. Nakamura, A., et al., *Follow-up of three patients with a large in-frame deletion of exons 45-55 in the Duchenne muscular dystrophy (DMD) gene.* J Clin Neurosci, 2008. 15(7): p. 757-63.
6. King, W. M., et al., *Orthopedic outcomes of long-term daily corticosteroid treatment in Duchenne muscular dystrophy.* Neurology, 2007. 68(19): p. 1607-13.
7. Alter, J., et al., *Systemic delivery of morpholino oligonucleotide restores dystrophin expression bodywide and improves dystrophic pathology.* Nat Med, 2006. 12(2): p. 175-7.
8. Goemans, N. M., et al., *Systemic administration of PRO051 in Duchenne's muscular dystrophy.* N Engl J Med, 2011. 364(16): p. 1513-22.
9. Kinali, M., et al., *Local restoration of dystrophin expression with the morpholino oligomer AVI-4658 in Duchenne muscular dystrophy: a single-blind, placebo-controlled, dose-escalation, proof-of-concept study.* Lancet Neurol, 2009. 8(10): p. 918-28.
10. van Deutekom, J. C., et al., *Local dystrophin restoration with antisense oligonucleotide PRO051.* N Engl J Med, 2007. 357(26): p. 2677-86.
11. Yokota, T., et al., *Efficacy of systemic morpholino exon-skipping in Duchenne dystrophy dogs.* Ann Neurol, 2009. 65(6): p. 667-76.
12. Lu, Q. L., et al., *Functional amounts of dystrophin produced by skipping the mutated exon in the mdx dystrophic mouse.* Nat Med, 2003. 9(8): p. 1009-14.
13. Crisp, A., et al., *Diaphragm rescue alone prevents heart dysfunction in dystrophic mice.* Hum Mol Genet, 2011. 20(3): p. 413-21.
14. Aartsma-Rus, A., et al., *Theoretic applicability of antisense-mediated exon skipping for Duchenne muscular dystrophy mutations.* Hum Mutat, 2009. 30(3): p. 293-9.

15. Goemans, N. M., et al., *24 week follow-up data from a phase I/IIa extension study of PRO051/GSK240220968 in subjects with Duchenne muscular dystrophy*, in *15th International Congress of The World Muscle Society*. 2010, Neuromuscular Disorders. p. 639.
16. Shrewsbury, S. B., et al., *Current progress and preliminary results with the systemic administration trial of AVI-4658, a novel phosphorodiamidate morpholino oligomer (PMO) skipping dystrophin exon 51 in Duchenne muscular dystrophy (DMD)*, in *15th International Congress of the World Muscle Society*. 2010, Neuromuscular Disorders. p. 639-640.
17. Neri, M., et al., *Dystrophin levels as low as 30% are sufficient to avoid muscular dystrophy in the human*. Neuromuscul Disord, 2007. 17(11-12): p. 913-8.
18. Hu, Y., et al., *Guanine analogues enhance antisense oligonucleotide-induced exon skipping in dystrophin gene in vitro and in vivo*. Mol Ther, 2010. 18(4): p. 812-8.
19. Krebs, J., *The influence of calcium signaling on the regulation of alternative splicing*. Biochim Biophys Acta, 2009. 1793(6): p. 979-84.
20. Glahn, K. P., et al., *Recognizing and managing a malignant hyperthermia crisis: guidelines from the European Malignant Hyperthermia Group*. Br J Anaesth. 105(4): p. 417-20.
21. Verrotti, A., et al., *Pharmacotherapy of spasticity in children with cerebral palsy*. Pediatr Neurol, 2006. 34(1): p. 1-6.
22. Bertorini, T. E., et al., *Effect of dantrolene in Duchenne muscular dystrophy*. Muscle Nerve, 1991. 14(6): p. 503-7.
23. Quinlan, J. G., S. R. Johnson, and F. J. Samaha, *Dantrolene normalizes serum creatine kinase in MDX mice*. Muscle Nerve, 1990. 13(3): p. 268-9.
24. Tennyson, C. N., H. J. Klamut, and R. G. Worton, *The human dystrophin gene requires 16 hours to be transcribed and is cotranscriptionally spliced*. Nat Genet, 1995. 9(2): p. 184-90.
25. O'Leary, D. A., et al., *Identification of small molecule and genetic modulators of AON-induced dystrophin exon skipping by high-throughput screening*. PLoS One, 2009. 4(12): p. e8348.
26. Kimura, E., et al., *Cell-lineage regulated myogenesis for dystrophin replacement: a novel therapeutic approach for treatment of muscular dystrophy*. Hum Mol Genet, 2008. 17(16): p. 2507-17.
27. Malerba, A., et al., *Dosing regimen has a significant impact on the efficiency of morpholino oligomer-induced exon skipping in mdx mice*. Hum Gene Ther, 2009. 20(9): p. 955-65.
28. Nishida, A., et al., *Chemical treatment enhances skipping of a mutated exon in the dystrophin gene*. Nat Commun, 2011. 2: p. 308.
29. Marius, P., et al., *Calcium release from ryanodine receptors in the nucleoplasmic reticulum*. Cell Calcium, 2006. 39(1): p. 65-73.
30. Bellinger, A. M., et al., *Hypernitrosylated ryanodine receptor calcium release channels are leaky in dystrophic muscle*. Nat Med, 2009. 15(3): p. 325-30.
31. Shan, J., et al., *Role of chronic ryanodine receptor phosphorylation in heart failure and beta-adrenergic receptor blockade in mice*. J Clin Invest. 120(12): p. 4375-87.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional Application No. 61/529,041, filed Aug. 30, 2011, and in the figures are hereby incorporated in their entirety by reference, particularly with regard to the information for which they are cited.

The invention claimed is:

1. A method for enhancing exon skipping in an mRNA of interest, comprising contacting the mRNA with an antisense oligonucleotide that is specific for a splicing sequence in the mRNA and an effective amount of dantrolene, Ryanodine, or RyCal S107, or a pharmaceutically acceptable salt, hydrate, solvate, or isomer thereof.

2. The method of claim 1, wherein the mRNA is from the muscle dystrophin (DMD) gene.

3. The method of claim 2, wherein the exon which is skipped is exon 23, 44, 45, 50, 51, 52 and/or 53 of the DMD gene.

4. The method of claim 1, wherein the method is carried out in vitro.

5. The method of claim 1, wherein the method is carried out in a subject that has Duchenne Muscular Dystrophy (DMD), is an animal model of DMD, or is another animal in which the exon skipping can be assayed.

6. The method of claim 5, wherein the subject is human.

7. The method of claim 1, wherein the compound is dantrolene or an active variant thereof.

8. The method of claim 7, wherein the compound is dantrolene.

9. The method of claim 1, wherein the exon which is skipped is exon 51 of the DMD gene.

10. The method of claim 2, wherein the antisense oligonucleotide has a sequence identical to the sequence of SEQ ID NO. 2.

11. The method of claim 1, wherein a sub-optimal amount of the antisense oligonucleotide contacts the mRNA, wherein the sub-optimal amount is an amount that is less than a clinically effective dose of the antisense oligonucleotide used in in vivo administration for exon skipping without the small molecule.

12. The method of claim 11, wherein the sub-optimal amount of the antisense oligonucleotide is an amount that produces 20% or less exon skipping than is produced by a clinically effective dose of the antisense oligonucleotide used in in vivo administration for exon skipping without the small molecule.

13. The method of claim 1, wherein the method is for enhancing antisense oligonucleotide induced exon skipping caused by the antisense oligonucleotide.

14. The method of claim 1, wherein the compound is Ryanodine or RyCal S107, or an active variant thereof.

15. The method of claim 14, wherein the compound is Ryanodine.

16. The method of claim 14, wherein the compound is RyCal S107.

* * * * *

SEQUENCE LISTING

```
<160> NUMBER OF SEQ ID NOS: 96

<210> SEQ ID NO 1
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aacuuccucu uuaacagaaa agcauac                                              27

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ucaaggaaga uggcauuucu                                                      20

<210> SEQ ID NO 3
<211> LENGTH: 20
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggccaaaccu cggcuuaccu                                               20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcaggtgtaa ccgtaacc                                                 18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgtacaaat tccctgtagc                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagtagcccc atcacatttg                                               20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ataacgcaat ggacaagtg                                                19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cctactctgc cctcaacttc                                               20

<210> SEQ ID NO 9
<211> LENGTH: 20
<212> TYPE: DNA

<213> ORGANISM: Artificial Sequence
<220> FEATURE:
<223> OTHER INFORMATION: Description of Artificial Sequence: Synthetic
     primer

<400> SEQUENCE: 9
agtatcccaa caccctgctc                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 10
gccacagatg ccactacttc                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 11
caacttcagc acaggagacc                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 12
gagccacatc gctcagacac                                                20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 13
catgtagttg aggtcaatga agg                                            23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 14
catcaactat gtcaccagca tccg                                           24

<210> SEQ ID NO 15
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 15
ggctgaacct tagaagagtc                                                     20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gagaccttct atgatgcagc                                                     20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agagctcgtg gatgttctc                                                      19

<210> SEQ ID NO 18
<211> LENGTH: 81
<212> TYPE: DNA
<213> ORGANISM: Homo sapiens

<400> SEQUENCE: 18
atgctttggt gggaagaagt agaggactgt tgtaagtaca aagtaactaa aaatatattt         60
tactgtggca taacgtttag t                                                   81

<210> SEQ ID NO 19
<211> LENGTH: 162
<212> TYPE: DNA
<213> ORGANISM: Homo sapiens

<400> SEQUENCE: 19
ttatatttaa agttgcttcc taacttttat ttttttattt tgcatttttag atgaaagaga        60 agatgttcaa agaaaacat tcacaaaatg ggtaaatgca caattttcta aggtaagaat         120
ggtttgttac tttactttta agatctaagt tgtgaaattt tc                           162

<210> SEQ ID NO 20
<211> LENGTH: 193
<212> TYPE: DNA
<213> ORGANISM: Homo sapiens

<400> SEQUENCE: 20
atcattggaa gtgtgctttg ttaaattgag tgtattttttt ttaatttcag tttgggaagc       60
agcatattga gaacctcttc agtgacctac aggatgggag gcgcctccta gacctcctcg        120
aaggcctgac agggcaaaaa ctggtatgtg acttattttt aagaaagtta actttaaact        180
tagtagaatt tca                                                           193

<210> SEQ ID NO 21
<211> LENGTH: 178
```

<212> TYPE: DNA
<213> ORGANISM: Homo sapiens

<400> SEQUENCE: 21

```
attgtcggtc tctctgctgg tcagtgaaca ctcttttgtt ttgttctcag ccaaaagaaa      60
aaggatccac aagagttcat gccctgaaca atgtcaacaa ggcactgcgg gttttgcaga     120
acaataatgt aagtagtacc ctggacaagg tctggatgct gtgacacagc atgcttca      178
```

<210> SEQ ID NO 22
<211> LENGTH: 193
<212> TYPE: DNA
<213> ORGANISM: Homo sapiens

<400> SEQUENCE: 22

```
ctaggcattt ggtctcttac cttcaaatgt tttaccccctt tctttaacag gttgatttag     60
tgaatattgg aagtactgac atcgtagatg gaaatcataa actgactctt ggtttgattt    120
ggaatataat cctccactgg caggtaagaa tcctgatgaa tggtttcctt ttgggtaaca    180
ttaatcttgt ttt                                                       193
```

<210> SEQ ID NO 23
<211> LENGTH: 273
<212> TYPE: DNA
<213> ORGANISM: Homo sapiens

<400> SEQUENCE: 23

```
ttcttgctca aggaatgcat tttcttatga aaatttattt ccacatgtag gtcaaaaatg      60
taatgaaaaa tatcatggct ggattgcaac aaaccaacag tgaaaagatt ctcctgagct    120
gggtccgaca atcaactcgt aattatccac aggttaatgt aatcaacttc accaccagct    180
ggtctgatgg cctggctttg aatgctctca tccatagtca taggtaagaa gattactgag    240
acattaaata acttgtaaaa gtggtgattt aga                                 273
```

<210> SEQ ID NO 24
<211> LENGTH: 219
<212> TYPE: DNA
<213> ORGANISM: Homo sapiens

<400> SEQUENCE: 24

```
gattgattta tatttgtctt tgtgtatgtg tgtatgtgta tgtgttttag gccagaccta     60
tttgactgga atagtgtggt ttgccagcag tcagccacac aacgactgga acatgcattc   120
aacatcgcca gatatcaatt aggcatagag aaactactcg atcctgaagg ttggtaaatt   180
tctggactac cactgctttt agtatggtag agtttaatg                          219
```

<210> SEQ ID NO 25
<211> LENGTH: 282
<212> TYPE: DNA
<213> ORGANISM: Homo sapiens

<400> SEQUENCE: 25

```
tctcaaatat agaaaccaaa aattgatgtg tagtgttaat gtgcttacag atgttgatac     60
cacctatcca gataagaagt ccatcttaat gtacatcaca tcactcttcc aagttttgcc   120
tcaacaagtg agcattgaag ccatccagga agtggaaatg ttgccaaggc cacctaaagt   180
gactaaagaa gaacattttc agttacatca tcaaatgcac tattctcaac aggtaaagtg   240
tgtaaaggac agctactatt caagatgttt tctgttttat at                      282
```

<210> SEQ ID NO 26
<211> LENGTH: 229
<212> TYPE: DNA
<213> ORGANISM: Homo sapiens

<400> SEQUENCE: 26

```
atggtttttc cccctcctct ctatccactc ccccaaaccc ttctctgcag atcacggtca    60
gtctagcaca gggatatgag agaacttctt cccctaagcc tcgattcaag agctatgcct   120
acacacaggc tgcttatgtc accacctctg accctacacg gagcccattt ccttcacagg   180
tctgtcaaca tttactctct gttgtacaaa ccagagaact gcttccaag               229
```

<210> SEQ ID NO 27
<211> LENGTH: 289
<212> TYPE: DNA
<213> ORGANISM: Homo sapiens

<400> SEQUENCE: 27

```
aatctgcaaa gacattaatt gtgtaacacc caatttattt tattgtgcag catttggaag    60
ctcctgaaga caagtcattt ggcagttcat tgatggagag tgaagtaaac ctggaccgtt   120
atcaaacagc tttagaagaa gtattatcgt ggcttctttc tgctgaggac acattgcaag   180
cacaaggaga gatttctaat gatgtggaag tggtgaaaga ccagtttcat actcatgagg   240
taaactaaaa cgttaattta caaaacaaaa catatgactt gttataatg               289
```

<210> SEQ ID NO 28
<211> LENGTH: 282
<212> TYPE: DNA
<213> ORGANISM: Homo sapiens

<400> SEQUENCE: 28

```
ccgatttacc tagagttcta attacaattg ttaacttcct tctttgtcag gggtacatga    60
tggatttgac agcccatcag ggccgggttg gtaatattct acaattggga agtaagctga   120
ttggaacagg aaaattatca gaagatgaag aaactgaagt acaagagcag atgaatctcc   180
taaattcaag atgggaatgc tcagggtag ctagcatgga aaaacaaagc aagtaagtcc    240
ttatttgttt ttaattaaga agactaacaa gttttggaag ct                     282
```

<210> SEQ ID NO 29
<211> LENGTH: 251
<212> TYPE: DNA
<213> ORGANISM: Homo sapiens

<400> SEQUENCE: 29

```
taataagttg ctttcaaaga ggtcataata ggcttctttc aaattttcag tttacataga    60
gttttaatgg atctccagaa tcagaaactg aaagagttga atgactggct aacaaaaaca   120
gaagaaagaa caaggaaaat ggaggaagag cctcttggac ctgatcttga agacctaaaa   180
cgccaagtac aacaacataa ggtaggtgta tcttatgttg cgtgctttct actagaaagc   240
aaactctgtg t                                                        251
```

<210> SEQ ID NO 30
<211> LENGTH: 220
<212> TYPE: DNA
<213> ORGANISM: Homo sapiens

<400> SEQUENCE: 30

```
cacatgtaag aatatcattt taatttcctt taaaacattt tatctttcag gtgcttcaag    60
```

```
aagatctaga acaagaacaa gtcagggtca attctctcac tcacatggtg gtggtagttg      120
atgaatctag tggagatcac gcaactgctg ctttggaaga acaacttaag gtcagattat      180
tttgcttagt aaactaaata tgtccttttaa aagaactata                            220

<210> SEQ ID NO 31
<211> LENGTH: 202
<212> TYPE: DNA
<213> ORGANISM: Homo sapiens

<400> SEQUENCE: 31
cgtagttacc aattgtttgc tgatgctgtg cttgattgtc tcttctccag gtattgggag       60
atcgatgggc aaacatctgt agatggacag aagaccgctg ggttctttta caagacatcc      120
ttctcaaatg gcaacgtctt actgaagaac aggtgtgtca tgtgtgagaa actagctgta     180
aaagacacgg ggggatatta aa                                                202

<210> SEQ ID NO 32
<211> LENGTH: 208
<212> TYPE: DNA
<213> ORGANISM: Homo sapiens

<400> SEQUENCE: 32
agtaaagatt tatgtttatt tattccttgg aattctttaa tgtcttgcag tgcctttta       60 gtgcatggct ttcagaaaaa gaagatgcag tgaacaagat tcacacaact ggctttaaag     120
atcaaaatga aatgttatca agtcttcaaa aactggccgt atgtactttc tagctttcaa     180
tggtcttata aaacccagt actgtata                                         208

<210> SEQ ID NO 33
<211> LENGTH: 280
<212> TYPE: DNA
<213> ORGANISM: Homo sapiens

<400> SEQUENCE: 33
tgtatggaat gcaacccagg cttattctgt gatctttctt gttttaacag gttttaaaag       60
cggatctaga aaagaaaaag caatccatgg gcaaactgta ttcactcaaa caagatcttc     120
tttcaacact gaagaataag tcagtgaccc agaagacgga agcatggctg ataactttg      180 cccggtgttg ggataattta gtccaaaaac ttgaaagag tacagcacag gttagtgata       240
ccaattatca tgctacagac tatctcagag attttttaaa                            280

<210> SEQ ID NO 34
<211> LENGTH: 276
<212> TYPE: DNA
<213> ORGANISM: Homo sapiens

<400> SEQUENCE: 34
actgaagtct ttctagcaat gtctgacctc tgtttcaata cttctcacag atttcacagg       60
ctgtcaccac cactcagcca tcactaacac agacaactgt aatggaaaca gtaactacgg     120
tgaccacaag ggaacagatc ctggtaaagc atgctcaaga ggaacttcca ccaccacctc    180
cccaaaagaa gaggcagatt actgtggatt ctgaaattag gaaaaggtga gagcatctta      240
agcttttatc tgcaaatgaa gtggagaaaa ctcatt                                276

<210> SEQ ID NO 35
<211> LENGTH: 224
<212> TYPE: DNA
```

<213> ORGANISM: Homo sapiens

<400> SEQUENCE: 35

| gaagaaagag ataatcaaga aataatgact tttatttttt gctgtcttag gttggatgtt | 60 |
| gatataactg aacttcacag ctggattact cgctcagaag ctgtgttgca gagtcctgaa | 120 |
| tttgcaatct ttcggaagga aggcaacttc tcagacttaa agaaaaagt caatgtaggt | 180 |
| tatgcattaa tttttatatc tgtactcatt tgtgctgct tgta | 224 |

<210> SEQ ID NO 36
<211> LENGTH: 188
<212> TYPE: DNA
<213> ORGANISM: Homo sapiens

<400> SEQUENCE: 36

| agattcacag tccttgtatt gaattactca tctttgctct catgctgcag gccatagagc | 60 |
| gagaaaagc tgagaagttc agaaaactgc aagatgccag cagatcagct caggccctgg | 120 |
| tggaacagat ggtgaatggt aattcacga gttgatttag ataatcttct tagggatttg | 180 |
| ataaacac | 188 |

<210> SEQ ID NO 37
<211> LENGTH: 342
<212> TYPE: DNA
<213> ORGANISM: Homo sapiens

<400> SEQUENCE: 37

| tttcagtctg tgggttcagg ggatatattt aattattttt ttctttctag agggtgttaa | 60 |
| tgcagatagc atcaaacaag cctcagaaca actgaacagc cggtggatcg aattctgcca | 120 |
| gttgctaagt gagagactta actggctgga gtatcagaac aacatcatcg cttttctataa | 180 |
| tcagctacaa caattggagc agatgacaac tactgctgaa aactggttga aaatccaacc | 240 |
| caccacccca tcagagccaa cagcaattaa agtcagtta aaaatttgta aggtaagaat | 300 |
| ctcttctcct tccatttgga gcataatcaa taggtatttc tt | 342 |

<210> SEQ ID NO 38
<211> LENGTH: 281
<212> TYPE: DNA
<213> ORGANISM: Homo sapiens

<400> SEQUENCE: 38

| aatgtatgca agtaaacgt gttacttact ttccatactc tatggcacag gatgaagtca | 60 |
| accggctatc agatcttcaa cctcaaattg aacgattaaa aattcaaagc atagccctga | 120 |
| aagagaaagg acaaggaccc atgttcctgg atgcagactt tgtggccttt acaaatcatt | 180 |
| ttaagcaagt ctttctgat gtgcaggcca gagagaaaga gctacagaca agtaagtaaa | 240 |
| aagcctaaaa tggctaactt gacatttcc aaaatggtta t | 281 |

<210> SEQ ID NO 39
<211> LENGTH: 246
<212> TYPE: DNA
<213> ORGANISM: Homo sapiens

<400> SEQUENCE: 39

| aagtgtgaaa caattaagtg attctcattc ttttttccct tttgataaag ttttgacac | 60 |
| tttgccacca atgcgctatc aggagaccat gagtgccatc aggacatggg tccagcagtc | 120 |
| agaaaccaaa ctctccatac ctcaacttag tgtcaccgac tatgaaatca tggagcagag | 180 |

```
actcggggaa ttgcaggtct gtgaatattt gaatgtcaaa acaataaagc acgcttatca      240
agcatt                                                                 246

<210> SEQ ID NO 40
<211> LENGTH: 313
<212> TYPE: DNA
<213> ORGANISM: Homo sapiens

<400> SEQUENCE: 40
aattattatt catcaattag ggtaaatgta tttaaaaaat tgttttttag gctttacaaa      60
gttctctgca agagcaacaa agtggcctat actatctcag caccactgtg aaagagatgt     120
cgaagaaagc gccctctgaa attagccgga aatatcaatc agaatttgaa gaaattgagg     180
gacgctggaa gaagctctcc tcccagctgg ttgagcattg tcaaaagcta gaggagcaaa     240
tgaataaact ccgaaaaatt caggtaattc aagattttac tttctaccct catttttatt     300
tacttgtttt ttc                                                        313

<210> SEQ ID NO 41
<211> LENGTH: 214
<212> TYPE: DNA
<213> ORGANISM: Homo sapiens

<400> SEQUENCE: 41
ttaaaagtaa tcagcacacc agtaatgcct tataacgggt ctcgtttcag aatcacatac      60
aaaccctgaa gaaatggatg gctgaagttg atgttttttct gaaggaggaa tggcctgccc    120 tggggattc agaaattcta aaaaagcagc tgaaacagtg cagagtaaga tttttatatg      180
atgcctttaa tatgaataat tttgtatgaa tatt                                 214

<210> SEQ ID NO 42
<211> LENGTH: 256
<212> TYPE: DNA
<213> ORGANISM: Homo sapiens

<400> SEQUENCE: 42
tatgtggcag taattttttt cagctggctt aaattgattt attttcttag cttttagtca      60
gtgatattca gacaattcag cccagtctaa acagtgtcaa tgaaggtggg cagaagataa     120
agaatgaagc agagccagag tttgcttcga gacttgagac agaactcaaa gaacttaaca    180
ctcagtggga tcacatgtgc caacaggtat agacaatctc tttcactgtg gcttgcctca    240
acgtacttaa ctaaga                                                     256

<210> SEQ ID NO 43
<211> LENGTH: 271
<212> TYPE: DNA
<213> ORGANISM: Homo sapiens

<400> SEQUENCE: 43
atgtttcatc actgtcaata atcgtgtttt gtttgtttgt tttgtggaag gtctatgcca      60
gaaaggaggc cttgaaggga ggtttggaga aaactgtaag cctccagaaa gatctatcag     120
agatgcacga atggatgaca caagctgaag aagagtatct tgagagagat ttgaatata     180 aaactccaga tgaattacag aaagcagttg aagagatgaa ggtaaaaaaa aaaaagaaa     240 aactaagtaa aacaaaggaa ataaatggaa a                                    271

<210> SEQ ID NO 44
```

<211> LENGTH: 283
<212> TYPE: DNA
<213> ORGANISM: Homo sapiens

<400> SEQUENCE: 44

```
ggatgtaaag ttattttcat gctattaaga gagcattctt tattttttcag agagctaaag      60 aagaggccca acaaaaagaa gcgaaagtga aactccttac tgagtctgta aatagtgtca     120
tagctcaagc tccacctgta gcacaagagg ccttaaaaaa ggaacttgaa actctaacca     180
ccaactacca gtggctctgc actaggctga atgggaaatg caagactttg gaagtcagtt     240
gcttttcttg gtctttgtca atgatatgtc aatacatggt cat                      283
```

<210> SEQ ID NO 45
<211> LENGTH: 235
<212> TYPE: DNA
<213> ORGANISM: Homo sapiens

<400> SEQUENCE: 45

```
tttactttc taccataata tttaatctgt gatatatatt tctttcttag gaagtttggg      60
catgttggca tgagttattg tcatacttgg agaaagcaaa caagtggcta atgaagtag     120 aatttaaact taaaaccact gaaaacattc ctggcggagc tgaggaaatc tctgaggtgc     180
tagatgtaag ttgtaaatta agccaaatga tgataattta tatgcagtat taaaa         235
```

<210> SEQ ID NO 46
<211> LENGTH: 250
<212> TYPE: DNA
<213> ORGANISM: Homo sapiens

<400> SEQUENCE: 46

```
tgtatttaga aaaaaagga gaaatagtaa ttattgcaaa tgtgtttcag tcacttgaaa      60
atttgatgcg acattcagag gataacccaa atcagattcg catattggca cagaccctaa     120
cagatggcgg agtcatggat gagctaatca atgaggaact tgagacattt aattctcgtt     180
ggagggaact acatgaagag gtatgaagat aagtgaaaaa tctctttaat ctaatttgca     240
ttaatgtata                                                          250
```

<210> SEQ ID NO 47
<211> LENGTH: 262
<212> TYPE: DNA
<213> ORGANISM: Homo sapiens

<400> SEQUENCE: 47

```
gctatcaaga gtaaacattt aactgataca ctcttattcc ttctttttag gctgtaagga      60
ggcaaaagtt gcttgaacag agcatccagt ctgcccagga gactgaaaaa tccttacact     120
taatccagga gtccctcaca ttcattgaca agcagttggc agcttatatt gcagacaagg     180
tggacgcagc tcaaatgcct caggaagccc aggcaagtac atctgggaat cagcttccat     240
tcttttgttt ttattacttc aa                                             262
```

<210> SEQ ID NO 48
<211> LENGTH: 211
<212> TYPE: DNA
<213> ORGANISM: Homo sapiens

<400> SEQUENCE: 48

```
tagttgttct ttgtagagca tgctgactaa taatgctatc ctcccaacag aaaatccaat      60
ctgatttgac aagtcatgag atcagtttag aagaaatgaa gaaacataat caggggaagg     120
```

```
aggctgccca aagagtcctg tctcagattg atgttgcaca ggtatatgtt atttcagaaa      180
ctaaggaacg tgttttcgtt gggcattata c                                    211

<210> SEQ ID NO 49
<211> LENGTH: 274
<212> TYPE: DNA
<213> ORGANISM: Homo sapiens

<400> SEQUENCE: 49
ttgtttgaaa ggcaaaatta aatcagtgcc ttttacact gtccttacag aaaaaattac       60
aagatgtctc catgaagttt cgattattcc agaaaccagc caattttgag cagcgtctac     120
aagaaagtaa gatgatttta gatgaagtga agatgcactt gcctgcattg gaaacaaaga    180
gtgtggaaca ggaagtagta cagtcacagc taaatcattg tgtggtatgt atttctggtg    240
gcaaatacgc aggtacccct tgactttcct catt                                274

<210> SEQ ID NO 50
<211> LENGTH: 256
<212> TYPE: DNA
<213> ORGANISM: Homo sapiens

<400> SEQUENCE: 50
aataatttaa ctctactgat tatcatgttt tgttttatgt ttaaacttag aacttgtata      60
aaagtctgag tgaagtgaag tctgaagtgg aaatggtgat aaagactgga cgtcagattg    120
tacagaaaaa gcagacggaa aatcccaaag aacttgatga agagtaaca gctttgaaat    180 tgcattataa tgagctggga gcaaaggtgt gtgcatgctg agaccacaaa cacttctttc    240
cactttcctt ataaat                                                    256

<210> SEQ ID NO 51
<211> LENGTH: 271
<212> TYPE: DNA
<213> ORGANISM: Homo sapiens

<400> SEQUENCE: 51
atttgaatta aagagtaaac taaattacat ttcattataa ttcttttcag gtaacagaaa      60
gaaagcaaca gttggagaaa tgcttgaaat tgtcccgtaa gatgcgaaag gaaatgaatg    120
tcttgacaga atggctggca gctacagata tggaattgac aaagagatca gcagttgaag    180
gaatgcctag taatttggat tctgaagttg cctggggaaa ggtaaaacct atatcactga    240
aggttatttt gaacatacgt gaaaacacat a                                   271

<210> SEQ ID NO 52
<211> LENGTH: 280
<212> TYPE: DNA
<213> ORGANISM: Homo sapiens

<400> SEQUENCE: 52
tcttaagact acaagacatt acttgaaggt caatgctctc cttttcacag gctactcaaa      60
aagagattga gaaacagaag gtgcacctga agagtatcac agaggtagga gaggccttga    120 aaacagttttt gggcaagaag gagacgttgg tggaagataa actcagtctt ctgaatagta    180
actggatagc tgtcacctcc cgagcagaag agtggttaaa tcttttgttg gtaagagaaa    240
aggctagaag ctttttacacc cttctctgtc acgagaaaaa                         280

<210> SEQ ID NO 53
```

<211> LENGTH: 229
<212> TYPE: DNA
<213> ORGANISM: Homo sapiens

<400> SEQUENCE: 53

```
aagaatattg tctaaccaat aatgccatgg tatgtctctg tacaattaag gaataccaga      60
aacacatgga aacttttgac cagaatgtgg accacatcac aaagtggatc attcaggctg     120
acacactttt ggatgaatca gagaaaaaga aacccagca aaaagaagac gtgcttaagg      180
tagcaaataa aatatgaaaa gtaatgtcca aattgtacac cagttactt                 229
```

<210> SEQ ID NO 54
<211> LENGTH: 271
<212> TYPE: DNA
<213> ORGANISM: Homo sapiens

<400> SEQUENCE: 54

```
ccttcattaa ttactaactt caagtcctat ctcttgctca tggaatatag cgtttaaagg      60
cagaactgaa tgacatacgc ccaaaggtgg actctacacg tgaccaagca gcaaacttga    120
tggcaaaccg cggtgaccac tgcaggaaat tagtagagcc ccaaatctca gagctcaacc    180
atcgatttgc agccatttca cacagaatta agactggaaa ggtaggaaga tctactccaa    240
ggtggaaact tgtgctaaat ggtctcttgc g                                   271
```

<210> SEQ ID NO 55
<211> LENGTH: 223
<212> TYPE: DNA
<213> ORGANISM: Homo sapiens

<400> SEQUENCE: 55

```
ttctaataaa aagtaatttt gatttaaagt agcactatct ttttttttag gcctccattc      60
ctttgaagga attggagcag tttaactcag atatacaaaa attgcttgaa ccactggagg    120
ctgaaattca gcaggggtg aatctgaaag aggaagactt caataaagat atggtaaatt     180
ggttgtgata aaagtgtgaa tgaactagga gtggaaataa ata                       223
```

<210> SEQ ID NO 56
<211> LENGTH: 238
<212> TYPE: DNA
<213> ORGANISM: Homo sapiens

<400> SEQUENCE: 56

```
acagcttttt aaaaccaaa atgaagactg tacttgttgt ttttgatcag aatgaagaca       60
atgagggtac tgtaaaagaa ttgttgcaaa gaggagacaa cttacaacaa agaatcacag    120
atgagagaaa gcgagaggaa ataaagataa aacagcagct gttacagaca aaacataatg    180
ctctcaaggt attagagcta aaattataat ataccttgcc tgtggttttt ttttaata      238
```

<210> SEQ ID NO 57
<211> LENGTH: 253
<212> TYPE: DNA
<213> ORGANISM: Homo sapiens

<400> SEQUENCE: 57

```
tgcactatac atatatattg atattttaat aatgtctgca ccatgaacag gatttgaggt      60
ctcaaagaag aaaaaaggct ctagaaattt ctcatcagtg gtatcagtac aagaggcagg    120
ctgatgatct cctgaaatgc ttggatgaca ttgaaaaaaa attagccagc ctacctgagc    180
ccagagatga aaggaaaata aaggtaatgt tgttttagaa tgtcaatacc agatttttatt    240
```

-continued

```
atacagttta att                                                         253

<210> SEQ ID NO 58
<211> LENGTH: 283
<212> TYPE: DNA
<213> ORGANISM: Homo sapiens

<400> SEQUENCE: 58
tgatgtggtt agctaactgc cctgggccct gtattggttt tgctcaatag gaaattgatc       60
gggaattgca gaagaagaaa gaggagctga atgcagtgcg taggcaagct gagggcttgt     120
ctgaggatgg ggccgcaatg gcagtggagc caactcagat ccagctcagc aagcgctggc     180
gggaaattga gagcaaattt gctcagtttc gaagactcaa cttttgcacaa attgtgagtt    240 gttactggca aacccacgta tgtgtttgca actactactc tat                       283

<210> SEQ ID NO 59
<211> LENGTH: 295
<212> TYPE: DNA
<213> ORGANISM: Homo sapiens

<400> SEQUENCE: 59
ttcactgtta ggaagctaaa aaaaattgtt cttttgtata tctataccag cacactgtcc      60
gtgaagaaac gatgatggtg atgactgaag acatgccttt ggaaatttct tatgtgcctt     120
ctacttattt gactgaaatc actcatgtct cacaagccct attagaagtg gaacaacttc     180
tcaatgctcc tgacctctgt gctaaggact ttgaagatct cttttaagcaa gaggagtctc   240 tgaaggtaaa accaaagcac tttcattcgt attttacaag gtgatcatac tgatc          295

<210> SEQ ID NO 60
<211> LENGTH: 273
<212> TYPE: DNA
<213> ORGANISM: Homo sapiens

<400> SEQUENCE: 60
tatagacagc taattcattt ttttactgtt ttaaaatttt tatattacag aatataaaag      60
atagtctaca acaaagctca ggtcggattg acattattca tagcaagaag acagcagcat    120
tgcaaagtgc aacgcctgtg gaagggtgaa agctacagga agctctctcc cagcttgatt    180
tccaatggga aaaagttaac aaaatgtaca aggaccgaca agggtaggta acacatatat    240
ttttcttgat acttgcagaa atgatttgtt ttc                                 273

<210> SEQ ID NO 61
<211> LENGTH: 248
<212> TYPE: DNA
<213> ORGANISM: Homo sapiens

<400> SEQUENCE: 61
gttttacata atccatctat ttttcttgat ccatatgctt ttacctgcag gcgatttgac      60
agatctgttg agaaatggcg gcgttttcat tatgatataa agatatttaa tcagtggcta    120
acagaagctg aacagtttct cagaaagaca caaattcctg agaattggga acatgctaaa    180
tacaaatggt atcttaaggt aagtctttga tttgtttttt cgaaattgta tttatcttca    240
gcacatct                                                             248

<210> SEQ ID NO 62
<211> LENGTH: 276
<212> TYPE: DNA
```

<213> ORGANISM: Homo sapiens

<400> SEQUENCE: 62

```
taaaaagaca tggggcttca tttttgtttt gccttttggg tatcttacag gaactccagg      60
atggcattgg gcagcggcaa actgttgtca gaacattgaa tgcaactggg aagaaataa      120
ttcagcaatc ctcaaaaaca gatgccagta ttctacagga aaaattggga agcctgaatc     180
tgcggtggca ggaggtctgc aaacagctgt cagacagaaa aaagaggtag ggcgacagat    240
ctaataggaa tgaaaacatt ttagcagact ttttaa                              276
```

<210> SEQ ID NO 63
<211> LENGTH: 248
<212> TYPE: DNA
<213> ORGANISM: Homo sapiens

<400> SEQUENCE: 63

```
tgagaactat gttggaaaaa aaataacaa ttttattctt ctttctccag gctagaagaa       60
caaaagaata tcttgtcaga atttcaaaga gatttaaatg aatttgtttt atggttggag     120
gaagcagata acattgctag tatcccactt gaacctggaa aagagcagca actaaaagaa    180
aagcttgagc aagtcaaggt aattttattt tctcaaatcc cccagggcct gcttgcataa    240
agaagtat                                                              248
```

<210> SEQ ID NO 64
<211> LENGTH: 250
<212> TYPE: DNA
<213> ORGANISM: Homo sapiens

<400> SEQUENCE: 64

```
ggaattgtgc tgtaattcat tttaaacgtt gttgcatttg tctgtttcag ttactggtgg      60
aagagttgcc cctgcgccag ggaattctca acaattaaa tgaaactgga ggacccgtgc     120
ttgtaagtgc tcccataagc ccagaagagc aagataaact tgaaaataag ctcaagcaga    180
caaatctcca gtggataaag gttagacatt aaccatctct tccgtcacat gtgttaaatg    240
ttgcaagtat                                                            250
```

<210> SEQ ID NO 65
<211> LENGTH: 286
<212> TYPE: DNA
<213> ORGANISM: Homo sapiens

<400> SEQUENCE: 65

```
gcttatgcct tgagaattat ttacctttt aaaatgtatt ttcctttcag gtttccagag       60
ctttacctga gaacaagga gaaattgaag ctcaaataaa agaccttggg cagcttgaaa     120
aaaagcttga agaccttgaa gagcagttaa atcatctgct gctgtggtta tctcctatta    180
ggaatcagtt ggaaatttat aaccaaccaa accaagaagg accatttgac gttaaggtag    240
ggaacttttt gctttaaata tttttgtctt tttaagaaa aatggc                    286
```

<210> SEQ ID NO 66
<211> LENGTH: 202
<212> TYPE: DNA
<213> ORGANISM: Homo sapiens

<400> SEQUENCE: 66

```
ttattgctaa ctgtgaagtt aatctgcact atatgggttc ttttcccag gaaactgaaa       60
tagcagttca agctaaacaa ccggatgtgg aagagatttt gtctaaaggg cagcatttgt    120
```

```
acaaggaaaa accagccact cagccagtga aggtaatgaa gcaacctcta gcaatatcca      180
ttacctcata atgggttatg ct                                               202

<210> SEQ ID NO 67
<211> LENGTH: 209
<212> TYPE: DNA
<213> ORGANISM: Homo sapiens

<400> SEQUENCE: 67
atcttcaaag tgttaatcga ataagtaatg tgtatgcttt tctgttaaag aggaagttag       60
aagatctgag ctctgagtgg aaggcggtaa accgttact tcaagagctg agggcaaagc      120
agcctgacct agctcctgga ctgaccacta ttggagcctg taagtatact ggatcccatt     180
ctctttggct ctagctattt gttcaaaag                                        209

<210> SEQ ID NO 68
<211> LENGTH: 333
<212> TYPE: DNA
<213> ORGANISM: Homo sapiens

<400> SEQUENCE: 68
tttttctttt tcttcttttt tccttttgc aaaaacccaa atatttag ctcctactca          60 gactgttact ctggtgacac aacctgtggt tactaaggaa actgccatct ccaaactaga     120
aatgccatct tccttgatgt tggaggtacc tgctctggca gatttcaacc gggcttggac     180
agaacttacc gactggcttt ctctgcttga tcaagttata aaatcacaga gggtgatggt    240
gggtgacctt gaggatatca acgagatgat catcaagcag aaggtatgag aaaaaatgat    300
aaaagttggc agaagttttt ctttaaaatg aag                                   333

<210> SEQ ID NO 69
<211> LENGTH: 218
<212> TYPE: DNA
<213> ORGANISM: Homo sapiens

<400> SEQUENCE: 69
aatacacaac gctgaagaac cctgatacta agggatattt gttcttacag gcaacaatgc       60
aggatttgga acagaggcgt ccccagttgg aagaactcat taccgctgcc caaaatttga     120
aaaacaagac cagcaatcaa gaggctagaa caatcattac ggatcgaagt aagttttta      180 acaagcatgg gacacacaaa gcaagatgca tgacaagt                              218

<210> SEQ ID NO 70
<211> LENGTH: 312
<212> TYPE: DNA
<213> ORGANISM: Homo sapiens

<400> SEQUENCE: 70
cctccagact agcatttact actatatatt tatttttcct tttattctag ttgaaagaat       60
tcagaatcag tgggatgaag tacaagaaca ccttcagaac cggaggcaac agttgaatga     120
aatgttaaag gattcaacac aatggctgga agctaaggaa gaagctgagc aggtcttagg     180
acaggccaga gccaagcttg agtcatgaa ggagggtccc tatacagtag atgcaatcca     240
aaagaaaatc acagaaacca aggttagtat caaagatacc tttttaaaat aaaatactgg    300
ttacatttga ta                                                          312

<210> SEQ ID NO 71
```

```
<211> LENGTH: 255
<212> TYPE: DNA
<213> ORGANISM: Homo sapiens

<400> SEQUENCE: 71
atttcataaa aaaaactgac attcattctc tttctcataa aaatctatag cagttggcca      60
aagacctccg ccagtggcag acaaatgtag atgtggcaaa tgacttggcc ctgaaacttc     120
tccgggatta ttctgcagat gataccagaa aagtccacat gataacagag aatatcaatg     180
cctcttggag aagcattcat aaaaggtatg aattacatta tttctaaaac tactgttggc     240
tgtaataatg gggtg                                                      255

<210> SEQ ID NO 72
<211> LENGTH: 290
<212> TYPE: DNA
<213> ORGANISM: Homo sapiens

<400> SEQUENCE: 72
gcaccattct gatatttaat aattgcatct gaacatttgg tcctttgcag ggtgagtgag      60
cgagaggctg ctttggaaga aactcataga ttactgcaac agttccccct ggacctggaa     120
aagtttcttg cctggcttac agaagctgaa acaactgcca atgtcctaca ggatgctacc     180
cgtaaggaaa ggctcctaga agactccaag ggagtaaaag agctgatgaa acaatggcaa     240
gtaagtcagg catttccgct ttagcactct tgtggatcca attgaacaat                 290

<210> SEQ ID NO 73
<211> LENGTH: 273
<212> TYPE: DNA
<213> ORGANISM: Homo sapiens

<400> SEQUENCE: 73
ttcttttgtt tggtaattct gcacatattc ttcttcctgc tgtcctgtag gacctccaag      60
gtgaaattga agctcacaca gatgtttatc acaacctgga tgaaaacagc caaaaaatcc     120
tgagatccct ggaaggttcc gatgatgcag tcctgttaca aagacgtttg gataacatga     180
acttcaagtg gagtgaactt cggaaaaagt ctctcaacat taggtaggaa aagatgtgga     240
gcaaaaaggc cacaaatgaa ttaaaatggc caa                                  273

<210> SEQ ID NO 74
<211> LENGTH: 257
<212> TYPE: DNA
<213> ORGANISM: Homo sapiens

<400> SEQUENCE: 74
caattacact tctagatatt ctgacatggt acgctgctgt tcttttcag gtcccatttg       60
gaagccagtt ctgaccagtg gaagcgtctg cacctttctc tgcaggaact tctggtgtgg     120
ctacagctga aagatgatga attaagccgg caggcaccta ttggaggcga ctttccagca     180
gttcagaagc agaacgatgt acatagggta ggacattttt aagcctcgtg ccttgcacat     240
gttaagcaca tagtaat                                                    257

<210> SEQ ID NO 75
<211> LENGTH: 221
<212> TYPE: DNA
<213> ORGANISM: Homo sapiens

<400> SEQUENCE: 75
agaagaatgc cacaagccaa ataagcactt cttttcatct catttcacag gccttcaaga      60
```

```
gggaattgaa aactaaagaa cctgtaatca tgagtactct tgagactgta cgaatatttc    120
tgacagagca gcctttggaa ggactagaga aactctacca ggagcccaga ggtaattgaa    180
tgtggaacta taataacata ttgatagaag gatcagtggt g                         221
```

<210> SEQ ID NO 76
<211> LENGTH: 369
<212> TYPE: DNA
<213> ORGANISM: Homo sapiens

<400> SEQUENCE: 76

```
gtttaaaaaa aaagaatgtg gcctaaaacc ttgtcatatt gccaatttag agctgcctcc     60
tgaggagaga gcccagaatg tcactcggct tctacgaaag caggctgagg aggtcaatac    120
tgagtgggaa aaattgaacc tgcactccgc tgactggcag agaaaaatag atgagaccct    180
tgaaagactc cgggaacttc aagaggccac ggatgagctg gacctcaagc tgcgccaagc    240
tgaggtgatc aagggatcct ggcagcccgt gggcgatctc ctcattgact ctctccaaga    300
tcacctcgag aaagtcaagg taccgtctac ttctttgctt cagggccctt tgagagactc    360
aaaagagct                                                             369
```

<210> SEQ ID NO 77
<211> LENGTH: 247
<212> TYPE: DNA
<213> ORGANISM: Homo sapiens

<400> SEQUENCE: 77

```
ttgttttaaa tattctcatc ttccaatttg cttttgacta ttgcacacag gcacttcgag     60
gagaaattgc gcctctgaaa gagaacgtga gccacgtcaa tgaccttgct cgccagctta    120
ccactttggg cattcagctc tcaccgtata acctcagcac tctggaagac ctgaacacca    180
gatggaagct tctgcaggta agcacattgt aaacattgtt gtcctttgtt acagtaaaat    240
aatatac                                                               247
```

<210> SEQ ID NO 78
<211> LENGTH: 179
<212> TYPE: DNA
<213> ORGANISM: Homo sapiens

<400> SEQUENCE: 78

```
tcctcattat atagaatgag agaacatcat ttctctcctt ttcctcccag gtggccgtcg     60
aggaccgagt caggcagctg catgaagccc acagggactt tggtccagca tctcagcact    120
ttctttccag taagtcattt tcagcttttaa tcacttaact ttattgcatc ttgattaat    179
```

<210> SEQ ID NO 79
<211> LENGTH: 161
<212> TYPE: DNA
<213> ORGANISM: Homo sapiens

<400> SEQUENCE: 79

```
gcgatgaatt tgacctcctt gcctttcttt ttttcctccc ttcttttcag cgtctgtcca     60
gggtccctgg gagagagcca tctcgccaaa caaagtgccc tactatatca gtaagttgg    120 aagtatcaca tttttaaaag agcatttatt gtgactaacc t                         161
```

<210> SEQ ID NO 80
<211> LENGTH: 162
<212> TYPE: DNA

<213> ORGANISM: Homo sapiens

<400> SEQUENCE: 80

```
tgactactca ttgtaaatgc taaagtcttt ctttatgttt tgtgttttag ccacgagact    60
caaacaactt gctgggacca tcccaaaatg acagagctct accagtcttt aggtaaggac   120
atggccatgt ttcctccaag ttaaatgaca ggtgaccttt ag                      162
```

<210> SEQ ID NO 81
<211> LENGTH: 175
<212> TYPE: DNA
<213> ORGANISM: Homo sapiens

<400> SEQUENCE: 81

```
ctgttatttc tgatggaata acaaatgctc tttgttttcc ctcttttcag ctgacctgaa    60
taatgtcaga ttctcagctt ataggactgc catgaaactc cgaagactgc agaaggccct   120
ttgctgtaag tattggccag tatttgaaga tcttgatact atgtctttgc ttaga         175
```

<210> SEQ ID NO 82
<211> LENGTH: 302
<212> TYPE: DNA
<213> ORGANISM: Homo sapiens

<400> SEQUENCE: 82

```
aggaaggttt tactctttga gtcatttgtg attttatttg ttttttgcag tggatctctt    60
gagcctgtca gctgcatgtg atgccttgga ccagcacaac ctcaagcaaa atgaccagcc   120
catggatatc ctgcagatta ttaattgttt gaccactatt tatgaccgcc tggagcaaga   180
gcacaacaat ttggtcaacg tccctctctg cgtggatatg tgtctgaact ggctgctgaa   240
tgtttatgat acgtacgtat ggcatgtttt tatttcccgg gctctgtcac aggaggctta   300
gc                                                                 302
```

<210> SEQ ID NO 83
<211> LENGTH: 186
<212> TYPE: DNA
<213> ORGANISM: Homo sapiens

<400> SEQUENCE: 83

```
cctctaggaa agggtcagta attgttttct gctttgattc ttcataatag gggacgaaca    60
gggaggatcc gtgtcctgtc ttttaaaact ggcatcattt ccctgtgtaa agcacatttg   120
gaagacaagt acagatgtaa gtcgtgtata ttaatgctgt attcttttat taatgttggc   180
taatta                                                             186
```

<210> SEQ ID NO 84
<211> LENGTH: 258
<212> TYPE: DNA
<213> ORGANISM: Homo sapiens

<400> SEQUENCE: 84

```
atccatgggt gctgtgtttt gactgttgca attttcttct tcctttgtag acctttcaa    60
gcaagtggca agttcaacag gattttgtga ccagcgcagg ctgggcctcc ttctgcatga   120
ttctatccaa attccaagac agttgggtga agttgcatcc tttggggca gtaacattga   180
gccaagtgtc cggagctgct tccaatttgt aagttattca ccttctaggt aacatattta   240
ttcttttcata ttttagaa                                               258
```

<210> SEQ ID NO 85
<211> LENGTH: 267
<212> TYPE: DNA
<213> ORGANISM: Homo sapiens

<400> SEQUENCE: 85
ctttcctttc atccttttgc cctccttctc tctccctcct gtctttgcag gctaataata     60
agccagagat cgaagcggcc ctcttcctag actggatgag actggaaccc cagtccatgg    120
tgtggctgcc cgtcctgcac agagtggctg ctgcagaaac tgccaagcat caggccaaat    180
gtaacatctg caaagagtgt ccaatcattg gattcaggta ttaggaacca aaaaaaaaat    240 gtcattttt tctcatcatt tttcacc                                         267

<210> SEQ ID NO 86
<211> LENGTH: 212
<212> TYPE: DNA
<213> ORGANISM: Homo sapiens

<400> SEQUENCE: 86
ggaatttgat tcgaagaaat acatacgtgt ttgttttgc tctttatcag gtacaggagt      60
ctaaagcact ttaattatga catctgccaa agctgctttt tttctggtcg agttgcaaaa    120
ggccataaaa tgcactatcc catggtggaa tattgcactc cggtaagttt gacgccagcc    180
tgacgtgaga gttagttcac ctgggataaa tt                                  212

<210> SEQ ID NO 87
<211> LENGTH: 237
<212> TYPE: DNA
<213> ORGANISM: Homo sapiens

<400> SEQUENCE: 87
tttgaaatca tcctgtccta aatctgatct caccatgatc tcccttttag actacatcag     60
gagaagatgt tcgagacttt gccaaggtac taaaaaacaa atttcgaacc aaaaggtatt    120
ttgcgaagca tccccgaatg ggctacctgc cagtgcagac tgtcttagag ggggacaaca    180
tggaaacgtg agtagtagca aaagcagaac acactcttgt tgatgtata tttgaac        237

<210> SEQ ID NO 88
<211> LENGTH: 139
<212> TYPE: DNA
<213> ORGANISM: Homo sapiens

<400> SEQUENCE: 88
cggctgagtt tgcgtgtgtc tccttcacca cctcattttt tgttttgcag tcccgttact     60
ctgatcaact tctggccagt agattctgcg tgagtacttt ttttgctgaa gggtgctgct    120
accaccaaca cattcgctc                                                 139

<210> SEQ ID NO 89
<211> LENGTH: 166
<212> TYPE: DNA
<213> ORGANISM: Homo sapiens

<400> SEQUENCE: 89
tctccattaa tggatggtat ctgtgactaa tcacattttc tgccttatag gcctgcctcg     60 tccctcagc tttcacacga tgatactcat tcacgcattg aacattatgc tagcaggtat    120
gagactagtt gtatgccagg caaatattga ttgaaataac taacca                   166

<210> SEQ ID NO 90

<211> LENGTH: 166
<212> TYPE: DNA
<213> ORGANISM: Homo sapiens

<400> SEQUENCE: 90

| | | | | | | |
|---|---|---|---|---|---|---|
| gattctaaga | cgtcacataa | gtttaatga | gcttttacgt | ttttatcag | gctagcagaa | 60 |
| atggaaaaca | gcaatggatc | ttatctaaat | gatagcatct | ctcctaatga | gagcatgtaa | 120 |
| gtatcccatc | tcttttaca | aaatgttcct | gacaatgaaa | ttgctt | | 166 |

<210> SEQ ID NO 91
<211> LENGTH: 259
<212> TYPE: DNA
<213> ORGANISM: Homo sapiens

<400> SEQUENCE: 91

| | | | | | | |
|---|---|---|---|---|---|---|
| aagcaaaata | aggggggaa | aaaccaaaa | cctttgattt | tattttccag | agatgatgaa | 60 |
| catttgttaa | tccagcatta | ctgccaaagt | ttgaaccagg | actcccccct | gagccagcct | 120 |
| cgtagtcctg | cccagatctt | gattccttta | gagagtgagg | aaagagggga | gctagagaga | 180 |
| atcctagcag | atcttgagga | agaaaacagg | tgagttttct | ttctagcttt | gtcattggta | 240 |
| tgcagagtgc | atacacttg | | | | | 259 |

<210> SEQ ID NO 92
<211> LENGTH: 344
<212> TYPE: DNA
<213> ORGANISM: Homo sapiens

<400> SEQUENCE: 92

| | | | | | | |
|---|---|---|---|---|---|---|
| ttttcttttt | ctttcttttt | ttttcttttt | tacttttttg | atgccaatag | gaatctgcaa | 60 |
| gcagaatatg | accgtctaaa | gcagcagcac | gaacataaag | gcctgtcccc | actgccgtcc | 120 |
| cctcctgaaa | tgatgcccac | ctctccccag | agtccccggg | atgctgagct | cattgctgag | 180 |
| gccaagctac | tgcgtcaaca | caaaggccgc | ctggaagcca | ggatgcaaat | cctggaagac | 240 |
| cacaataaac | agctggagtc | acagttacac | aggctaaggc | agctgctgga | gcaagtgagg | 300 |
| agagagatgg | gattttaca | aacattcatt | tttccctctt | aaac | | 344 |

<210> SEQ ID NO 93
<211> LENGTH: 224
<212> TYPE: DNA
<213> ORGANISM: Homo sapiens

<400> SEQUENCE: 93

| | | | | | | |
|---|---|---|---|---|---|---|
| tttgtatgtt | tattatgaaa | agtaattctg | ttttcttttg | gatgacttag | ccccaggcag | 60 |
| aggccaaagt | gaatggcaca | acggtgtcct | ctccttctac | ctctctacag | aggtccgaca | 120 |
| gcagtcagcc | tatgctgctc | cgagtggttg | gcagtcaaac | ttcggactcc | atgggtaagt | 180 |
| gtcctagcta | ctctcagatt | tgttgtctg | aagaaaggta | gagt | | 224 |

<210> SEQ ID NO 94
<211> LENGTH: 193
<212> TYPE: DNA
<213> ORGANISM: Homo sapiens

<400> SEQUENCE: 94

| | | | | | | |
|---|---|---|---|---|---|---|
| ctgttttcta | taaatgtaat | tttccattat | ttgttttttgc | ttttattaag | gtgaggaaga | 60 |
| tcttctcagt | cctccccagg | acacaagcac | agggttagag | gaggtgatgg | agcaactcaa | 120 |
| caactccttc | cctagttcaa | gaggtaagct | ccaataccta | gaagggactc | agatttgctg | 180 |

```
ggatcaggcc act                                                             193

<210> SEQ ID NO 95
<211> LENGTH: 132
<212> TYPE: DNA
<213> ORGANISM: Homo sapiens

<400> SEQUENCE: 95
ttttttcccc tttctgatat ctctgcctct tcctctctct attattaaag gaagaaatac          60
ccctggaaag ccaatgagag aggttagtga gattcaggct cacggccatg gcttctgtct         120
gtctcatcct gc                                                             132

<210> SEQ ID NO 96
<211> LENGTH: 62
<212> TYPE: DNA
<213> ORGANISM: Homo sapiens

<400> SEQUENCE: 96
tctatctgca cctttttgtaa agtctgtctt tctttctctt tgttttccag gacacaatgt         60
ag                                                                         62
```